(12) United States Patent
Putnins et al.

(10) Patent No.: US 10,196,345 B2
(45) Date of Patent: Feb. 5, 2019

(54) MAO-B SELECTIVE INHIBITOR COMPOUNDS, PHARMACEUTICAL COMPOSITIONS THEREOF AND USES THEREOF

(71) Applicants: The University of British Columbia, Vancouver (CA); Centre for Drug Research and Development, Vancouver (CA)

(72) Inventors: Edward Ewald Putnins, Richmond (CA); David Scott Grierson, Vancouver (CA); Ronan F.B. Gealageas, Vancouver (CA); Alice Andree Valentine Devineau, Vancouver (CA); Edith Mary Dullaghan, Vancouver (CA)

(73) Assignees: THE UNIVERSITY OF BRITISH COLUMBIA, Vancouver (CA); CENTRE FOR DRUG RESEARCH AND DEVELOPMENT, Vancouver (CA)

( * ) Notice: Subject to any disclaimer, the term of this patent is extended or adjusted under 35 U.S.C. 154(b) by 0 days.

(21) Appl. No.: 14/915,474

(22) PCT Filed: Aug. 29, 2014

(86) PCT No.: PCT/CA2014/000658
§ 371 (c)(1),
(2) Date: Feb. 29, 2016

(87) PCT Pub. No.: WO2015/027324
PCT Pub. Date: Mar. 5, 2015

(65) Prior Publication Data
US 2016/0207878 A1   Jul. 21, 2016

Related U.S. Application Data

(60) Provisional application No. 61/872,552, filed on Aug. 30, 2013.

(51) Int. Cl.
| | |
|---|---|
| C07C 229/36 | (2006.01) |
| C07C 255/54 | (2006.01) |
| C07D 311/16 | (2006.01) |
| C07C 217/60 | (2006.01) |
| C07C 229/14 | (2006.01) |
| C07C 255/42 | (2006.01) |
| C07C 255/43 | (2006.01) |
| C07D 213/30 | (2006.01) |
| C07C 235/74 | (2006.01) |
| C07D 213/74 | (2006.01) |
| C07D 231/12 | (2006.01) |
| C07D 231/14 | (2006.01) |
| C07D 233/64 | (2006.01) |

(Continued)

(52) U.S. Cl.
CPC .......... *C07C 229/36* (2013.01); *C07C 217/60* (2013.01); *C07C 229/14* (2013.01); *C07C 235/74* (2013.01); *C07C 255/42* (2013.01); *C07C 255/43* (2013.01); *C07C 255/54* (2013.01); *C07D 213/30* (2013.01); *C07D 213/74* (2013.01); *C07D 231/12* (2013.01); *C07D 231/14* (2013.01); *C07D 233/64* (2013.01); *C07D 233/90* (2013.01); *C07D 311/12* (2013.01); *C07D 311/16* (2013.01); *C07F 9/3886* (2013.01)

(58) Field of Classification Search
CPC .................................................... C07C 229/36
See application file for complete search history.

(56) References Cited

U.S. PATENT DOCUMENTS

| | | | |
|---|---|---|---|
| 6,632,830 B1 | 10/2003 | Acton et al. | |
| 2004/0082496 A1* | 4/2004 | Acton .................... | A61K 31/00 514/1 |

(Continued)

FOREIGN PATENT DOCUMENTS

| | | |
|---|---|---|
| JP | S58150562 A | 9/1983 |
| JP | H0987272 A | 3/1997 |
| WO | 0066104 A2 | 11/2000 |

OTHER PUBLICATIONS

Cancer and Metastasis Reviews (1998), 17(1), 91-106.*
(Continued)

*Primary Examiner* — Shawquia Jackson
(74) *Attorney, Agent, or Firm* — Saliwanchik, Lloyd & Eisenschenk

(57) ABSTRACT

Described herein are a series of compounds having the structure of Formula I:

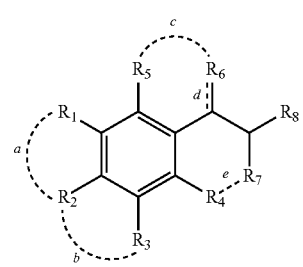

for use in the inhibition of MAO and uses thereof for the treatment of a barrier disease, obesity, solid epithelial cell tumor metastasis, diabetes, an auto-immune and inflammatory disease or a cardiometabolic disorder.

16 Claims, 23 Drawing Sheets

(51) Int. Cl.
  *C07D 233/90* (2006.01)
  *C07D 311/12* (2006.01)
  *C07F 9/38* (2006.01)

(56) References Cited

U.S. PATENT DOCUMENTS

| | | |
|---|---|---|
| 2005/0130225 A1 | 6/2005 | Zheng et al. |
| 2005/0130244 A1 | 6/2005 | Zheng et al. |
| 2007/0004683 A1 | 1/2007 | McElroy et al. |
| 2008/0009544 A1 | 1/2008 | Rao et al. |
| 2012/0015909 A1 | 1/2012 | McElroy et al. |
| 2014/0155355 A1 | 6/2014 | McElroy et al. |

OTHER PUBLICATIONS

Science (1999), vol. 286, 531-537.*
Cancer [online], [retrieved on Jul. 6, 2007]. Retrieved from the internet, URL http://www.nlm.nih.gov/medlineplus/cancer.html>.*
Shreder, K., et al., "Solid Phase Organic Synthesis of Piperazinone Containing Enkephalin Mimetics: A Readily Derivatized, Traceless Scaffold." *J. Comb. Chem.*, Mar. 1999, 1(5): 383-387.

* cited by examiner

FIGURE 10B.
PS-RG0245
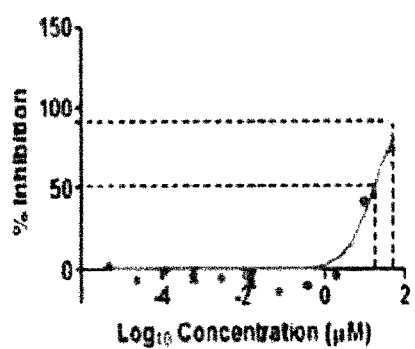
$IC_{50}$ = 17.2μM
$IC_{90}$ = 99.8μM
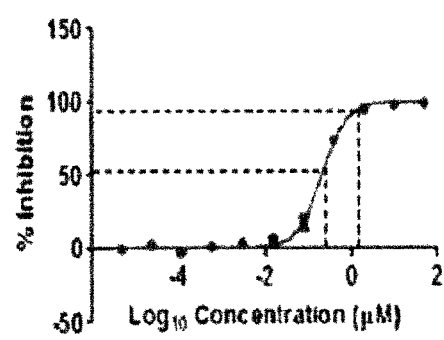
PS-AD0191
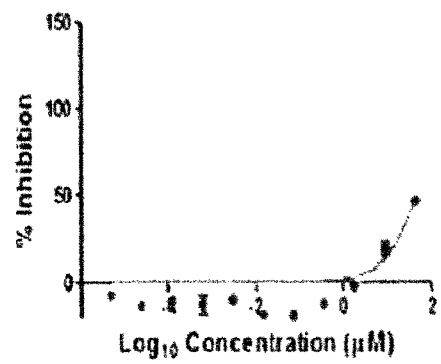
$IC_{50}$ = 54.6μM
$IC_{90}$ = 423.6μM
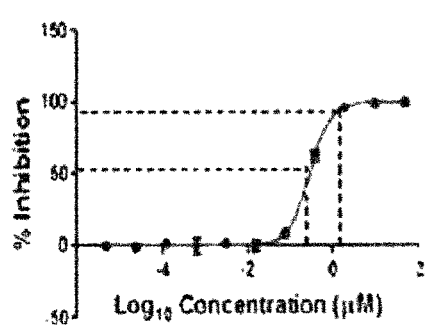

FIGURE 11.
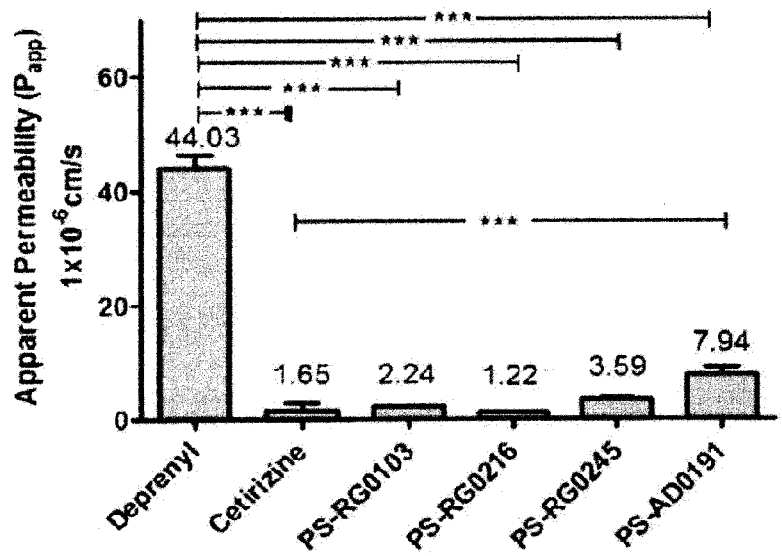
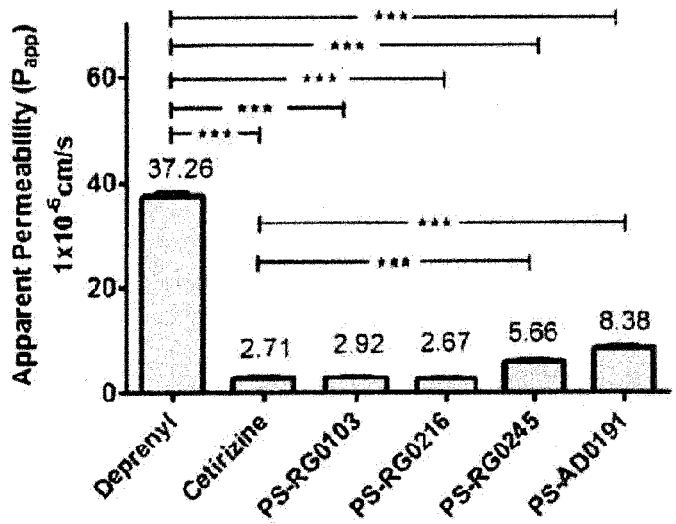
Apparent Permeability ($P_{app}$) Criteria:
Low Permeability = Less than $1 \times 10^{-6}$
Medium Permeability = Between $1 \times 10^{-6}$ and $10 \times 10^{-6}$
High Permeability = Greater than $10 \times 10^{-6}$ FIGURES 12 A and B.
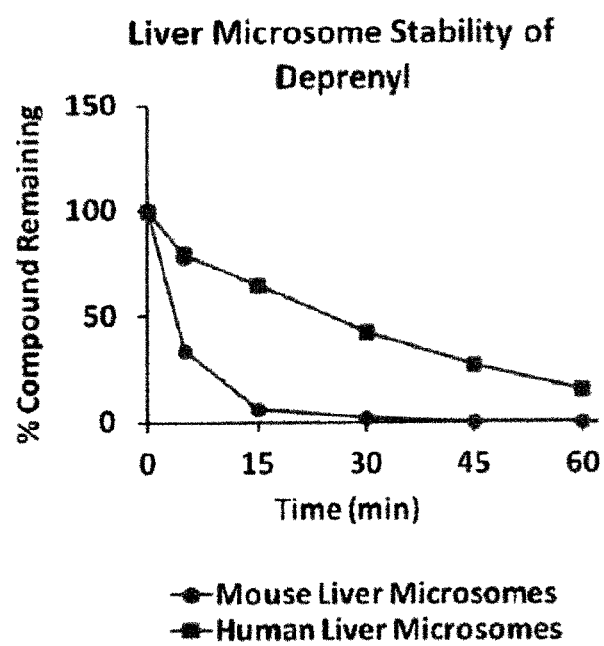
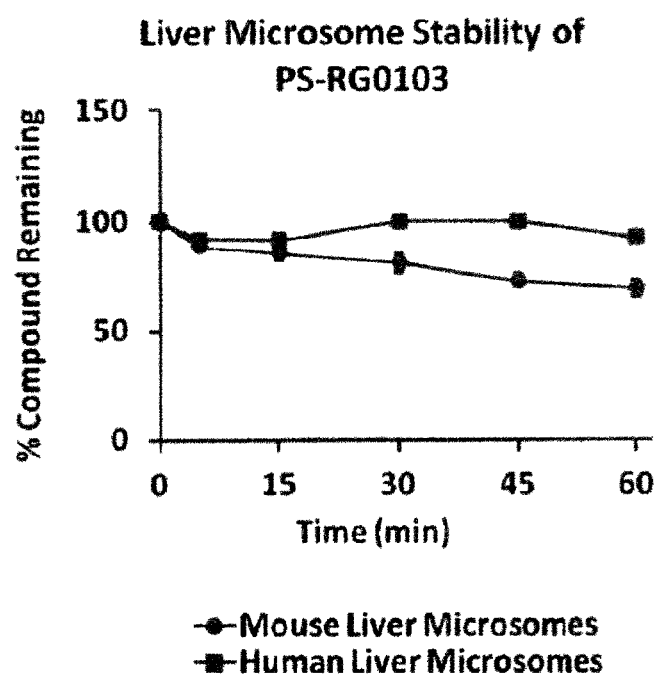

FIGURES 15 A and B
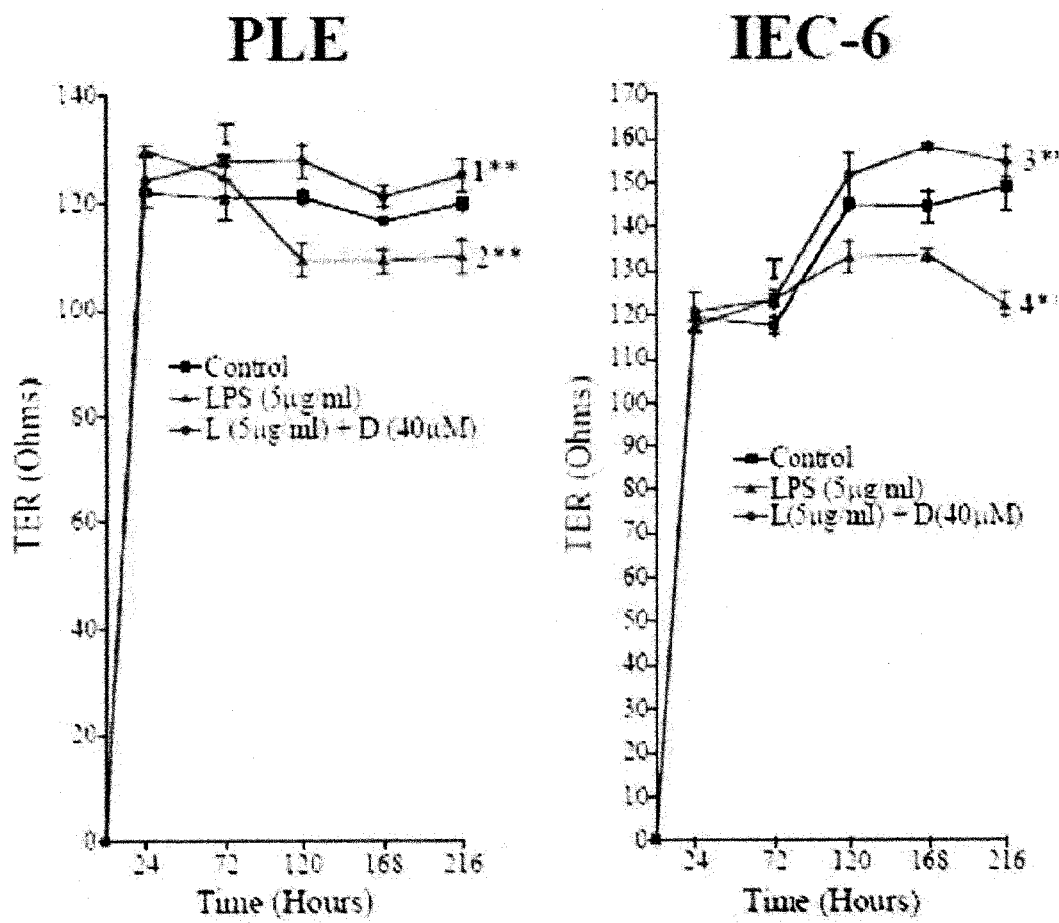

A

B

|  | d2 | d3 | d6 | d7 | d8 | d9 | d10 | d13 |
|---|---|---|---|---|---|---|---|---|
| 10 µM Deprenyl |  |  |  |  |  |  | 0.043 | 0.027 |
| 10 µM RG0103 |  |  | 0.047 | < 0.001 | < 0.001 | < 0.001 | < 0.001 | < 0.001 |
| 10 µM RG0216 |  |  | 0.039 | 0.014 |  | < 0.001 | < 0.001 | < 0.001 |
| 10 µM RG0245 |  |  | < 0.001 | < 0.001 | < 0.001 | < 0.001 | < 0.001 | < 0.001 |

|  | d2 | d5 | d7 | d9 | d11 | d13 | d16 | d19 | d21 | d23 |
|---|---|---|---|---|---|---|---|---|---|---|
| 20 µM Deprenyl |  |  |  |  |  |  |  |  |  |  |
| 20 µM RG0103 |  |  |  |  |  |  |  | < 0.001 | < 0.001 | < 0.001 |
| 20 µM RG0216 |  |  |  |  |  |  |  | < 0.001 | < 0.001 | < 0.001 |
| 20 µM RG0245 |  |  |  |  |  |  |  | < 0.001 | < 0.001 | < 0.001 |
| 20 µM AD0191 |  |  |  |  |  |  | < 0.001 | < 0.001 | < 0.001 | < 0.001 |

FIGURES 20 A-B
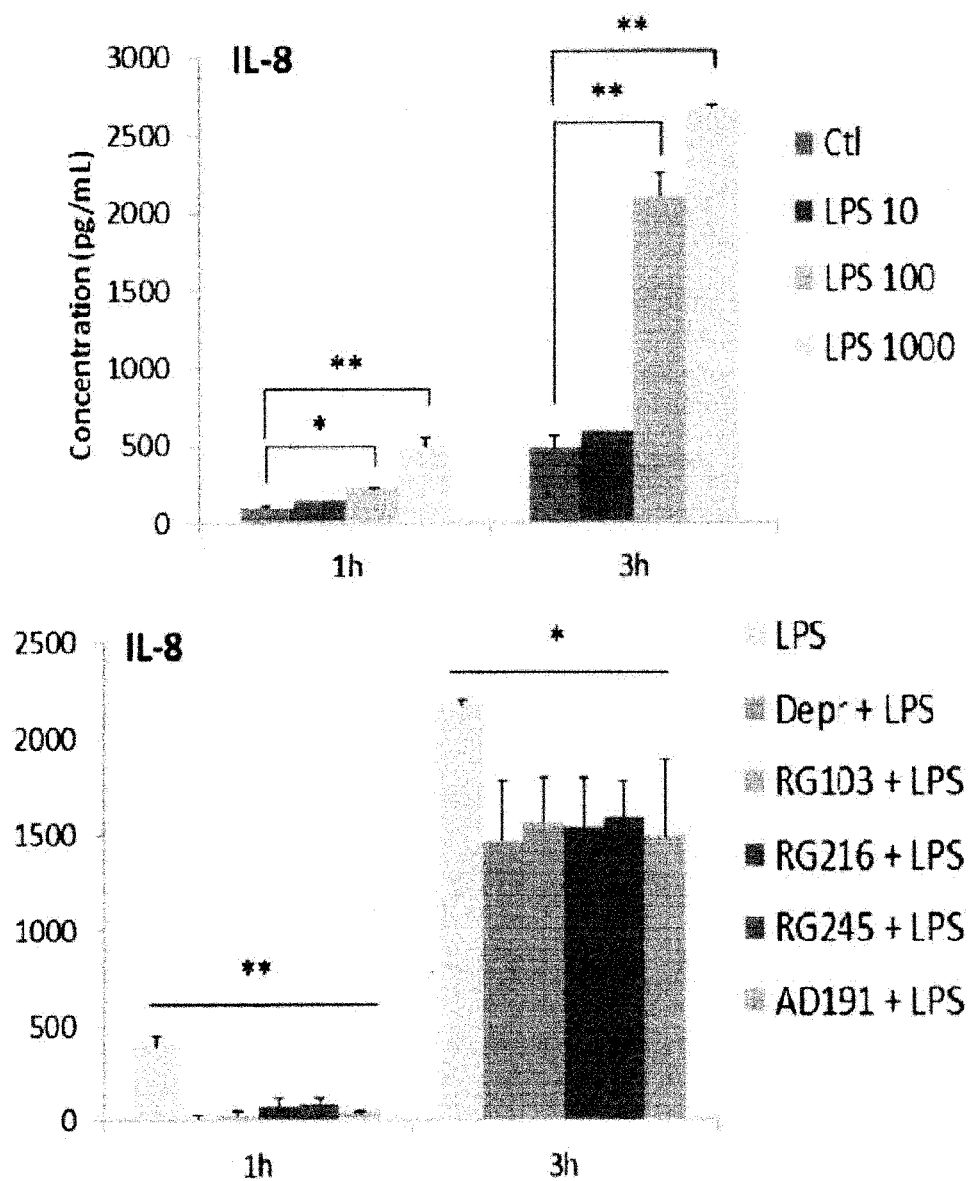

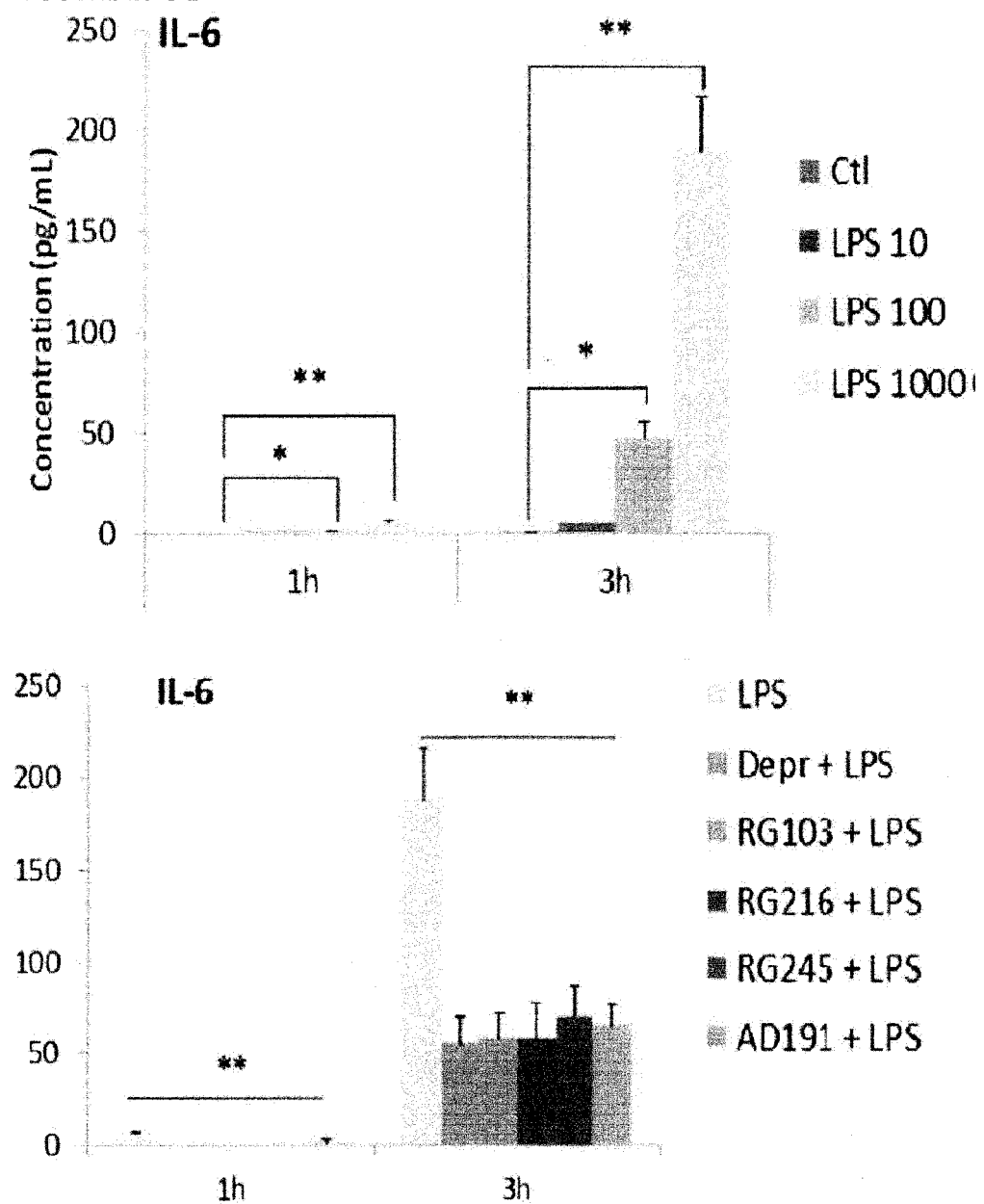

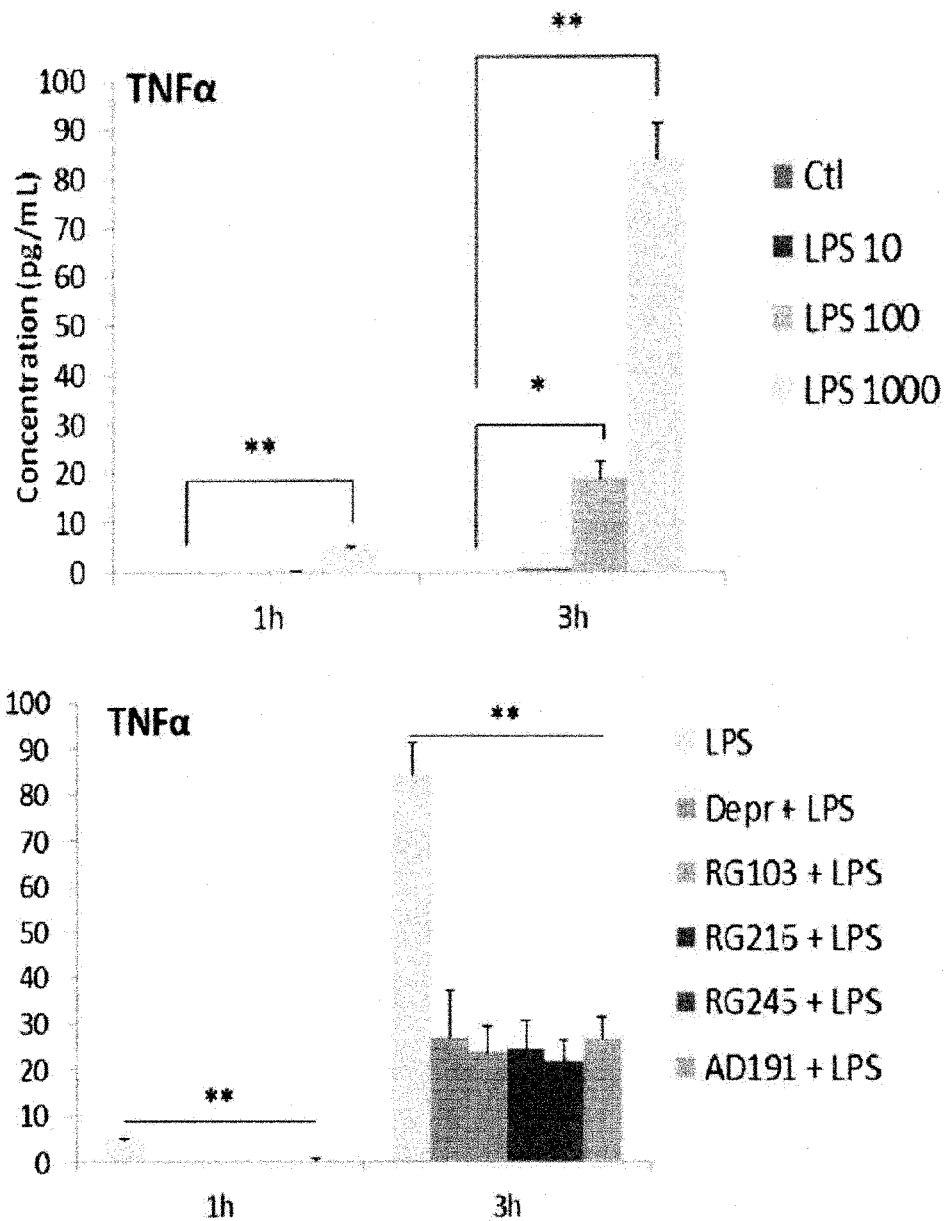
FIGURES 20 E-F

MAO-B SELECTIVE INHIBITOR COMPOUNDS, PHARMACEUTICAL COMPOSITIONS THEREOF AND USES THEREOF

CROSS-REFERENCE TO RELATED APPLICATIONS

This application is the U.S. national stage application of International Patent Application No. PCT/CA2014/000658, filed Aug. 29, 2014, which claims priority to U.S. Provisional Application No. 61/872,552, filed 30 Aug. 2013, the disclosures of which are hereby incorporated by reference in their entireties, including any figures, tables, or drawings.

TECHNICAL FIELD

The invention relates to MAO-B selective inhibitor therapeutics, pharmaceutical compositions thereof and their uses and methods for the treatment of various indications, including epithelial and endothelial diseases. In particular, to therapeutic compositions and methods of treating epithelial and endothelial diseases.

BACKGROUND

Epithelia form barriers that are essential to life. This is particularly true in oral and GI mucosal tissues that are constantly exposed to dietary and environmental antigens and the resident and foreign bacterial flora. For a barrier to exist, the intercellular space need be maintained and this is accomplished by the organization of the tight junction (TJ) complex. The multi-molecular TJ complex forms a belt at the apical portions of cells and is best divided into three groups: (i) integral TJ proteins that form strands which bridge the intercellular space and consist of proteins such as claudins, occludins, and junction adhesion molecules; (ii) cytoplasmic junctional molecules such as TJ proteins with PDZ domains i.e. zonula occludins (ZO-1, ZO-2, ZO-3); and (iii) the actin cytoskeleton. When assembled, TJs show ion and size selectivity for paracellular transport due to the presence of aqueous pores within paired TJ transmembrane proteins. The integrity of the TJ complex is dependent on connections between claudins and the actin cytoskeleton, which is largely mediated by PDZ domain-containing cytoplasmic proteins ZO-1, -2, and -3.

The mechanism by which amphiregulin (AR), an autocrine growth factor, regulates the barrier is not fully understood but the $H_2O_2$/TACE/EGFR ligand/EGFR signaling axis, also described as the "oxidant-induced metalloproteinase-dependent EGFR transactivation" pathway, was recently proposed (Forsyth, C. B., et al. J Pharmacol Exp Ther, 2007. 321(1):84-97). Putnins et al., using a rat periodontal disease model, identified increased EGFR signaling in diseased periodontal tissues (Firth, J. D., et al. J Clin Periodontol. 2013 40(1):8-17). Histological analysis of tissues from patients with inflammatory bowel diseases (IBD) e.g. Crohn's and ulcerative colitis have also shown AR expression primarily in the epithelium, whereas AR is absent in healthy patients (Nishimura, T., et al. Oncol Rep, 2008. 19(1):105-10).

SUMMARY

The present invention is based, in part, on the fortuitous discovery that certain compounds are capable of selectively inhibiting MAO-B, and furthermore that such compounds may have reduced ability to cross the blood brain barrier (BBB). Such compounds may therefore have important utility for treatment of diseases in which inhibition of MAO-B is likely beneficial. Such compounds may have particular utility for non-CNS diseases in which inhibition of MAO-B is likely beneficial as described herein, wherein the limited or reduced BBB permeability of such compounds may be advantageous in reducing or eliminating undesirable side effects that are common among various known MAO-B inhibitors, for instance deprenyl.

In accordance with one embodiment, there is provided a compound, the compound having the structure of Formula I:

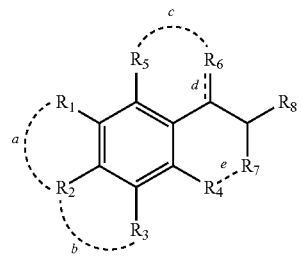

I wherein:

$R_1$ may be selected from the following: H; C1-4 alkyl, wherein a carbon in the C1-4 alkyl may be optionally substituted with an O, or an $NR_{13}$ heteroatom, and where one or more of the C1-4 alkyl hydrogens may be optionally substituted with a C5-7 cycloalkyl, wherein the C5-7 cycloalkyl ring may be optionally substituted with an O or N heteroatom and wherein one or more of the ring hydrogens of the C5-7 cycloalkyl may be optionally independently substituted with $CF_3$; F, Cl, Br, I, CN, $NO_2$, $COR_{14}$, $SO_2N(R_{14})_2$, $CO_2H$, $CON(R_{14})_2$, NHCHO; $OR_{15}$, $N(R_{15})_2$, Ar, and HetAr; $R_2$ may be selected from the following: H; C1-4 alkyl, wherein a carbon in the C1-4 alkyl may be optionally substituted with an O, or an $NR_{13}$ heteroatom, and where one or more of the C1-4 alkyl hydrogens may be optionally substituted with a C5-7 cycloalkyl, wherein the C5-7 cycloalkyl ring is optionally substituted with an O or N heteroatom and wherein one or more of the ring hydrogens of the C5-7 cycloalkyl may be optionally independently substituted with $CF_3$, F, Cl, Br, I, CN, $NO_2$, $COR_{14}$, $SO_2N(R_{14})_2$, $CO_2H$, $CON(R_{14})_2$, NHCHO; $OR_{15}$, $N(R_{15})_2$, Ar, and HetAr; $R_3$ may be selected from the following: H; C1-4 alkyl, wherein a carbon in the C1-4 alkyl may be optionally substituted with an O, or an $NR_{13}$ heteroatom, and where one or more of the C1-4 alkyl hydrogens may be optionally substituted with a C5-7 cycloalkyl, wherein the C5-7 cycloalkyl ring may be optionally substituted with an O or N heteroatom and wherein one or more of the ring hydrogens of the C5-7 cycloalkyl may be optionally independently substituted with $CF_3$, F, Cl, Br, I, CN, $NO_2$, $COR_{14}$, $SO_2N(R_{14})_2$, $CO_2H$, $CON(R_{14})_2$, NHCHO; $OR_{15}$, $N(R_{15})_2$, Ar, and HetAr; $R_{13}$ may be H or Me; $R_{14}$ may be H or Me; $R_{15}$ may be H, Me or $CF_3$; Ar may be

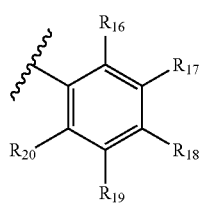

wherein $R_{16}$-$R_{20}$ may optionally and independently be selected from H, C1-4 alkyl, F, Cl, Br, I, $CF_3$, CN, $NO_2$, $OR_{13}$, $N(R_{13})_2$, $COR_{14}$, $CO_2R_{14}$, $CONHR_{14}$, $SO_2N(R_{14})_2$; wherein HetAr may be an unsubstituted, or variously substituted pyrimidine, furan, thiophene, imidazole, pyrrole, oxazole, isoxazole, thiazole, or isothiazole ring; $R_4$ may be optionally selected from H, CN, $NO_2$, $COR_{14}$, NHCHO, $SO_2N(R_{14})_2$, $CONHR_{14}$, $CO_2R_{14}$, pyrrole, tetrazole, oxadiazole, and N-hydroxypyrazole; $R_5$ may be optionally selected from H, CN, $NO_2$, $COR_{14}$, NHCHO, $SO_2N(R_{14})_2$, $CONHR_{14}$, $CO_2R_{14}$, pyrrole, tetrazole, oxadiazole, and N-hydroxypyrazole; $R_6$ may be H or $CH_2N(Me)CH_2CO_2H$; $R_7$ may be optionally selected from H, Me, $CH_2Cl$, $CH_2F$, $CH_2Br$, $CH_2CN$, $CH_2CH_2OH$, $CH_2OCH_2$phenyl, $CH_2OR_{14}$, $CON(R_{14})_2$, $CO_2R_{14}$, pyrrole, tetrazole, oxadiazole, N-hydroxypyrazole;
$R_8$ is

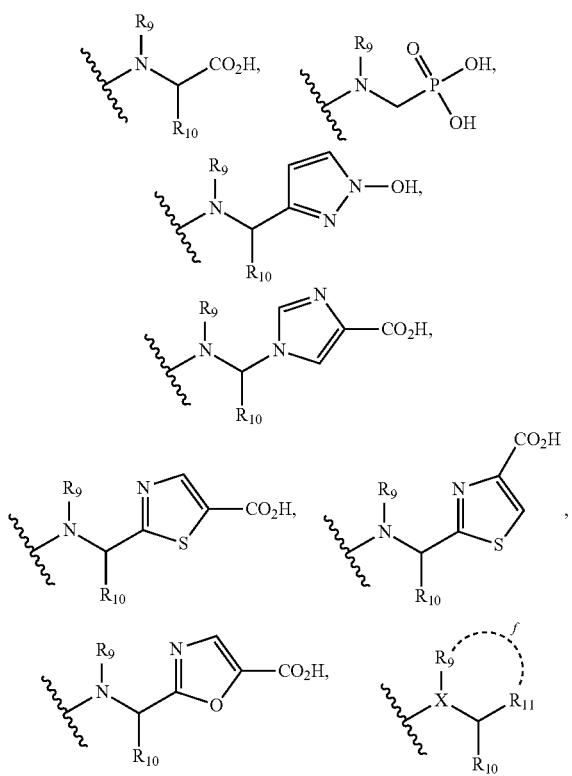

wherein: X may be N or C; $R_9$ may be H, Me, Et, isopropyl; $R_{10}$ may be H, Me, Et, $CH_2OH$, $CH_2SH$, $CH_2CO_2H$, $CH_2CH_2CO_2H$, $CH_2C(O)NH_2$, $CH_2CH_2CONH_2$; $R_{11}$ may be $CO_2H$, phosphate, N-hydroxypyrazole, aryl-$R_{12}$, heteroaryl-$R_{12}$; $R_{12}$ may be $CO_2H$, phosphate, CN; and wherein: $R_1$ and $R_2$ may optionally be covalently linked through a to form a C5-7 ring structure, wherein the ring structure optionally includes a methylenedioxy ($-OCH_2O-$), tetrahydrofuran ($-OCH_2CH_2-$), dioxane ($-OCH_2CH_2O-$), lactone ($-O(C=O)CH_2-$ or $-O(C=O)CH_2CH_2-$), unsaturated lactone ($-O(C=O)CHCH-$), pyrimidine, furan, thiophene, imidazole, pyrrole, oxazole, isoxazole, thiazole, or isothiazole ring structure; $R_2$ and $R_3$ may optionally be covalently linked through b to form a C5-7 ring structure, wherein the ring structure optionally includes a methylenedioxy ($-OCH_2O-$), tetrahydrofuran ($-OCH_2CH_2-$), dioxane ($-OCH_2CH_2O-$), lactone ($-O(C=O)CH_2-$ or $-O(C=O)CH_2CH_2-$), unsaturated lactone ($-O(C=O)CHCH-$), pyrimidine, furan, thiophene, imidazole, pyrrole, oxazole, isoxazole, thiazole, or isothiazole ring structure; $R_5$ and $R_6$ may optionally be covalently linked through c to form a C5-7 ring structure, wherein the bond d may be a single or double bond, and wherein the ring structure may be a pyridine, pyrimidine, isoxazole, isothiazole, furan, pyrazole, pyrrole, thiophene, or unsaturated δ-lactone, having the general structure:

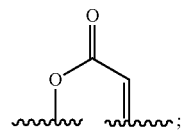 [SMILES: *OC(=O)C=*]

$R_4$ and $R_7$ may optionally be covalently linked through e to form a dual ring structure, selected from:

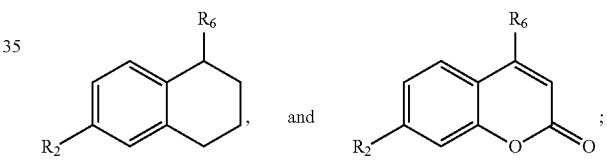

$R_9$ and $R_{11}$ may optionally be covalently linked through f to form a nitrogen heterocycle, wherein the nitrogen heterocycle may include: pyrrole, imidazole, thiazole, oxazole.

In accordance with a further embodiment, there is provided a compound having the structure of Formula II:

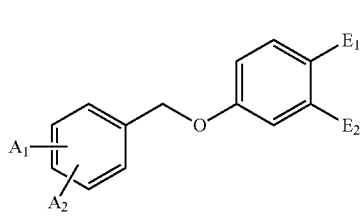

wherein: $A_1$ may be selected from F, Cl, Br, I, CN, OMe, $NO_2$, and $CO_2H$; $A_2$ may be selected from F, Cl, Br, I, CN, OMe, $NO_2$, and $CO_2H$; $E_1$ may be

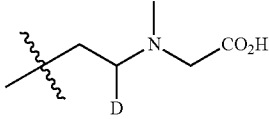 [SMILES: *CC([2H])N(C)CC(=O)O]

and $E_2$ may be H; or $E_1$ and $E_2$ form a ring having the structure

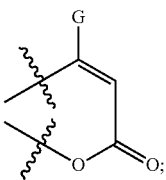

wherein: D may be H, Me, $CH_2Cl$, $CH_2F$, $CH_2Br$, $CH_2I$, $CH_2CN$, $CH_2CH_2OH$, $CH_2OCH_2$ phenyl, $CH_2OH$, or $CO_2Me$; and G may be $CH_2N(Me)CH_2CO_2H$.

In accordance with a further embodiment, there is provided a compound having the structure of Formula III:

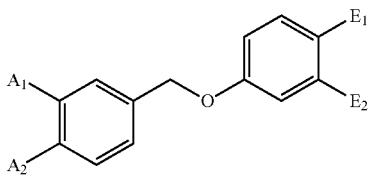

wherein: $A_1$ may be selected from F, Cl, Br, I, CN, OMe, $NO_2$, and $CO_2H$; $A_2$ may be selected from F, Cl, Br, I, CN, OMe, $NO_2$, and $CO_2H$; $E_1$ may be

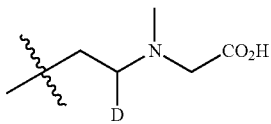 [SMILES: *CC([2H])N(C)CC(=O)O]

and $E_2$ may be H; or $E_1$ and $E_2$ form a ring having the structure

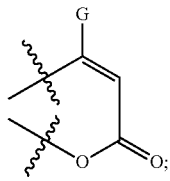

wherein: D may be H, Me, $CH_2Cl$, $CH_2F$, $CH_2Br$, $CH_2I$, $CH_2CN$, $CH_2CH_2OH$, $CH_2OCH_2$ phenyl, $CH_2OH$, or $CO_2Me$; and G may be $CH_2N(Me)CH_2CO_2H$ In accordance with a further embodiment, there is provided a commercial package comprising: (a) a compound as described herein; and (b) instructions for use of the compound in the treatment of a barrier disease, obesity, solid epithelial cell tumor metastasis, diabetes, an auto-immune and inflammatory disease or a cardiometabolic disorder.

In accordance with a further embodiment, there is provided a commercial package comprising: (a) an MAO-B selective inhibitor having a reduced ability to cross the blood brain barrier; and (b) instructions for use of the MAO-B selective inhibitor having a reduced ability to cross the blood brain barrier in the treatment of a barrier disease, the method comprising administering to a subject in need thereof.

In accordance with a further embodiment, there is provided a use of a compound as described herein for the treatment of a barrier disease, obesity, solid epithelial cell tumor metastasis, diabetes, auto-immune and inflammatory disease or cardiometabolic disorders.

In accordance with a further embodiment, there is provided a use of a compound as described herein in the manufacture of a medicament for the treatment of a barrier disease, obesity, solid epithelial cell tumor metastasis, diabetes, auto-immune and inflammatory disease or cardiometabolic disorders.

In accordance with a further embodiment, there is provided an MAO-B selective inhibitor having a reduced ability to cross the blood brain barrier for the treatment of a barrier disease.

In accordance with a further embodiment, there is provided an MAO-B selective inhibitor having a reduced ability to cross the blood brain barrier for the manufacture of a medicament for treatment a of barrier disease.

In accordance with a further embodiment, there is provided a compound as described herein, for use in the treatment of a barrier disease, obesity, solid epithelial cell tumor metastasis, diabetes, auto-immune and inflammatory disease or cardiometabolic disorders.

In accordance with a further embodiment, there is provided a pharmaceutical composition, the composition comprising: a (a) compound as described herein; and (b) a pharmaceutically acceptable carrier.

In accordance with a further embodiment, there is provided a method of treating a barrier disease, obesity, solid epithelial cell tumor metastasis, diabetes, auto-immune and inflammatory disease or cardiometabolic disorders the method including administering an MAO-B selective inhibitor as described herein to a subject in need thereof.

In accordance with a further embodiment, there is provided a method of treating a barrier disease, the method including administering an MAO-B selective inhibitor having a reduced ability to cross the blood brain barrier to a subject in need thereof.

$R_1$ may be selected from the following: H; $CF_3$; F; Cl; Br; I; CN; $NO_2$; $COR_{14}$; $SO_2N(R_{14})_2$; $CO_2H$; $CON(R_{14})_2$; NHCHO; $OR_{15}$; $N(R_{15})_2$; Ar; HetAr; C1-4 alkyl, wherein a carbon in the C1-4 alkyl may be optionally substituted with an O, or an $NR_{13}$ heteroatom, and where one or more of the C1-4 alkyl hydrogens may be optionally substituted with a C5-7 cycloalkyl, wherein the C5-7 cycloalkyl ring may be optionally substituted with an O or N heteroatom and wherein one or more of the ring hydrogens of the C5-7 cycloalkyl may be optionally independently substituted with $CF_3$; F, Cl, Br, I, CN, $NO_2$, $COR_{14}$, $SO_2N(R_{14})_2$, $CO_2H$, $CON(R_{14})_2$, NHCHO; $OR_{15}$, $N(R_{15})_2$, Ar, and HetAr.

$R_2$ may be selected from the following: H; $CF_3$; F; Cl; Br; I; CN; $NO_2$; $COR_{14}$; $SO_2N(R_{14})_2$; $CO_2H$; $CON(R_{14})_2$; NHCHO; $OR_{15}$; $N(R_{15})_2$; Ar; HetAr; C1-4 alkyl, wherein a carbon in the C1-4 alkyl may be optionally substituted with an O, or an $NR_{13}$ heteroatom, and where one or more of the C1-4 alkyl hydrogens may be optionally substituted with a C5-7 cycloalkyl, wherein the C5-7 cycloalkyl ring may be optionally substituted with an O or N heteroatom and wherein one or more of the ring hydrogens of the C5-7 cycloalkyl may be optionally independently substituted with $CF_3$, F, Cl, Br, I, CN, $NO_2$, $COR_{14}$, $SO_2N(R_{14})_2$, $CO_2H$, $CON(R_{14})_2$, NHCHO; $OR_{15}$, $N(R_{15})_2$, Ar, and HetAr.

$R_3$ may be selected from the following: H; $CF_3$; F; Cl; Br; I; CN; $NO_2$; $COR_{14}$; $SO_2N(R_{14})_2$; $CO_2H$; $CON(R_{14})_2$; NHCHO; $OR_{15}$; $N(R_{15})_2$; Ar; HetAr; C1-4 alkyl, wherein a carbon in the C1-4 alkyl may be optionally substituted with an O, or an NR$_{13}$ heteroatom, and where one or more of the C1-4 alkyl hydrogens may be optionally substituted with a C5-7 cycloalkyl, wherein the C5-7 cycloalkyl ring may be optionally substituted with an O or N heteroatom and wherein one or more of the ring hydrogens of the C5-7 cycloalkyl may be optionally independently substituted with CF$_3$, F, Cl, Br, I, CN, NO$_2$, COR$_{14}$, SO$_2$N(R$_{14}$)$_2$, CO$_2$H, CON(R$_{14}$)$_2$, NHCHO; OR$_{15}$, N(R$_{15}$)$_2$, Ar, and HetAr.

R$_1$ may be H. R$_2$ may be a C1-4 alkyl, wherein a carbon in the C1-4 alkyl may be optionally substituted with an O, and where one or more of the C1-4 alkyl hydrogens may optionally be substituted with a C5-7 cycloalkyl, wherein the C5-7 cycloalkyl ring may optionally be substituted with an O or N heteroatom and wherein one or more of the ring hydrogens of the C5-7 cycloalkyl are optionally independently substituted with CF$_3$, F, Cl, Br, I, CN, NO$_2$, OMe, COR$_{14}$, SO$_2$N(R$_{14}$)$_2$, CO$_2$H, CON(R$_{14}$)$_2$, and NHCHO. R$_3$ may be H. R$_4$ may be optionally selected from H, CN, NO$_2$, COR$_{14}$, NHCHO, SO$_2$N(R$_{14}$)$_2$, CONHR$_{14}$, and CO$_2$R$_{14}$. R$_5$ may be optionally selected from H, CN, NO$_2$, COR$_{14}$, NHCHO, SO$_2$N(R$_{14}$)$_2$, CONHR$_{14}$, and CO$_2$R$_{14}$. R$_6$ may be H or CH$_2$N(Me)CH$_2$CO$_2$H. R$_7$ may be optionally selected from H, Me, CH$_2$Cl, CH$_2$F, CH$_2$Br, CH$_2$CN, CH$_2$CH$_2$OH, CH$_2$OCH$_2$.phenyl, CH$_2$OR$_{14}$, and CO$_2$R$_{14}$. R$_8$ may be

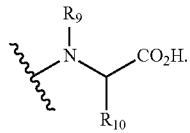

R$_9$ may be H, Me, or Et. R$_{10}$ may be H, Me, Et, CH$_2$OH, CH$_2$SH, CH$_2$CO$_2$H, CH$_2$CH$_2$CO$_2$H, CH$_2$C(O)NH$_2$, or CH$_2$CH$_2$CONH$_2$. R$_{13}$ may be H or Me. R$_{14}$ may be H or Me. R$_{15}$ may be H, Me or CF$_3$. R$_1$ and R$_2$ may be optionally covalently linked through a to form a C5-7 ring structure, wherein the ring structure optionally includes a methylenedioxy (—OCH$_2$O—), tetrahydrofuran (—OCH$_2$CH$_2$—), dioxane (—OCH$_2$CH$_2$O—), lactone (—O(C=O)CH$_2$— or —O(C=O)CH$_2$CH$_2$—), unsaturated lactone (—O(C=O)CHCH—), pyrimidine, furan, thiophene, imidazole, pyrrole, oxazole, isoxazole, thiazole, or isothiazole ring structure. R$_4$ and R$_7$ may be optionally covalently linked through e to form a dual ring structure having the structure:

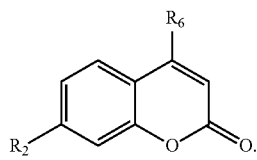

R$_2$ may be a C1-4 alkyl, wherein a carbon in the C1-4 alkyl may be optionally substituted with an O, and where one or more of the C1-4 alkyl hydrogens may be optionally substituted with a C5-7 cycloalkyl, wherein one or more of the ring hydrogens of the C5-7 cycloalkyl may be optionally independently substituted with F, Cl, Br, I, CN, NO$_2$, OMe, and CO$_2$H. R$_4$ may be H. R$_5$ may be H. R$_6$ may be H. R$_7$ may be H, Me, CH$_2$Cl, CH$_2$F, CH$_2$Br, CH$_2$CN, CH$_2$CH$_2$OH, CH$_2$OCH$_2$.phenyl, CH$_2$OH, or CO$_2$Me. R$_8$ may be

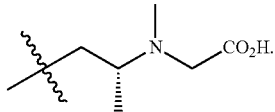

R$_1$ and R$_2$ may be optionally covalently linked through a to form a dual ring structure having the structure:

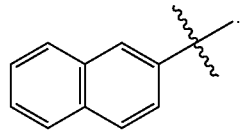 [SMILES: *c1ccc2ccccc2c1]

R$_4$ and R$_7$ may be optionally covalently linked through e to form a dual ring structure having the structure:

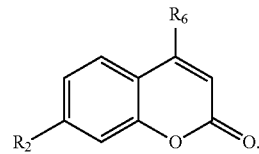

A$_1$ may be selected from F, Cl, Br, CN, OMe, NO$_2$, and CO$_2$H. A$_2$ may be selected from F, Cl, Br, CN, OMe, NO$_2$, and CO$_2$H. D may be H, Me, CH$_2$Cl, CH$_2$CN, CH$_2$CH$_2$OH, CH$_2$OCH$_2$.phenyl, CH$_2$OH, or CO$_2$Me. A$_1$ may be selected from F, Cl, Br, CN, OMe, NO$_2$, and CO$_2$H. A$_2$ may be selected from F, Cl, Br, CN, OMe, NO$_2$, and CO$_2$H. D may be Me, CH$_2$Cl, CH$_2$CN, CH$_2$CH$_2$OH, CH$_2$OCH$_2$.phenyl, CH$_2$OH, or CO$_2$Me.

A$_1$ may be selected from F, Cl, Br, OMe, and NO$_2$. A$_2$ may be selected from F, Cl, Br, OMe, and NO$_2$. D may be Me, CH$_2$Cl, CH$_2$CN, CH$_2$OH, or CO$_2$Me.

A$_1$ may be F, Cl, Br or OMe. A$_2$ may be from F, Cl, Br or OMe. D may be Me, CH$_2$Cl or CH$_2$OH.

The compound may be selected from one of more of:

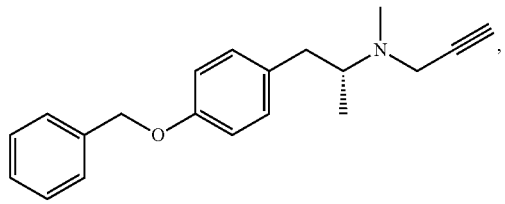

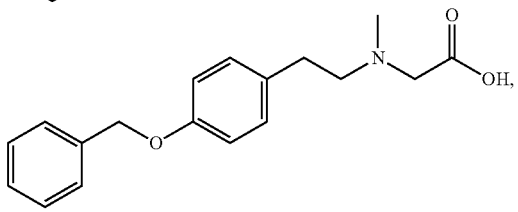

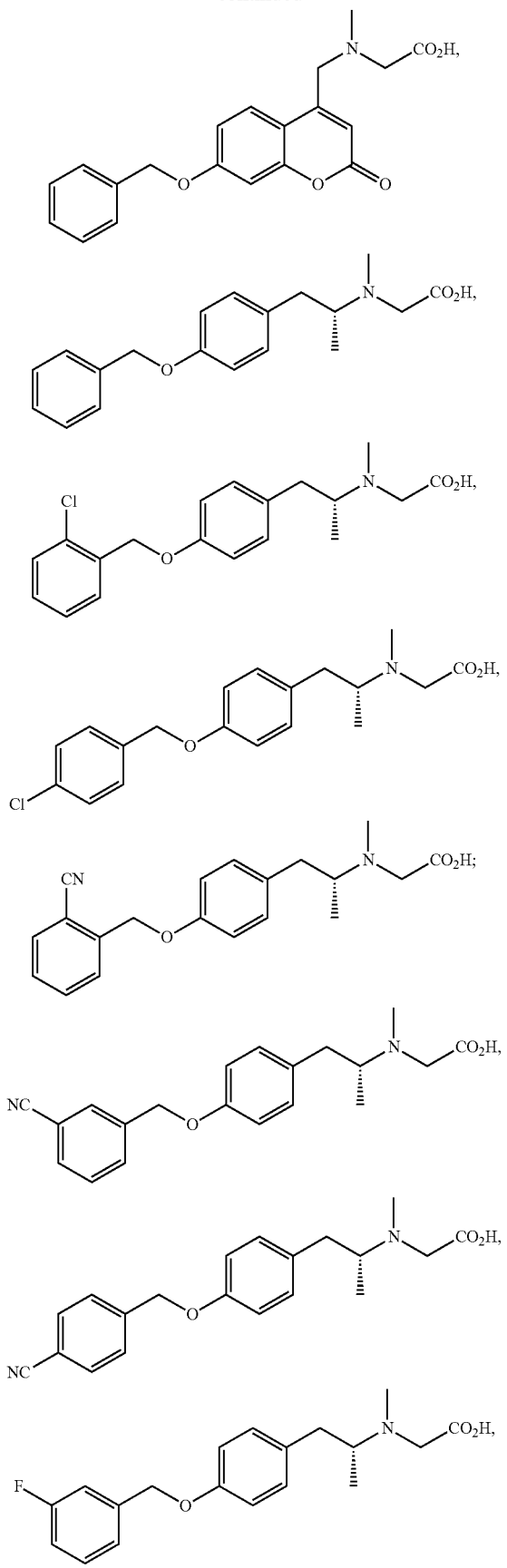
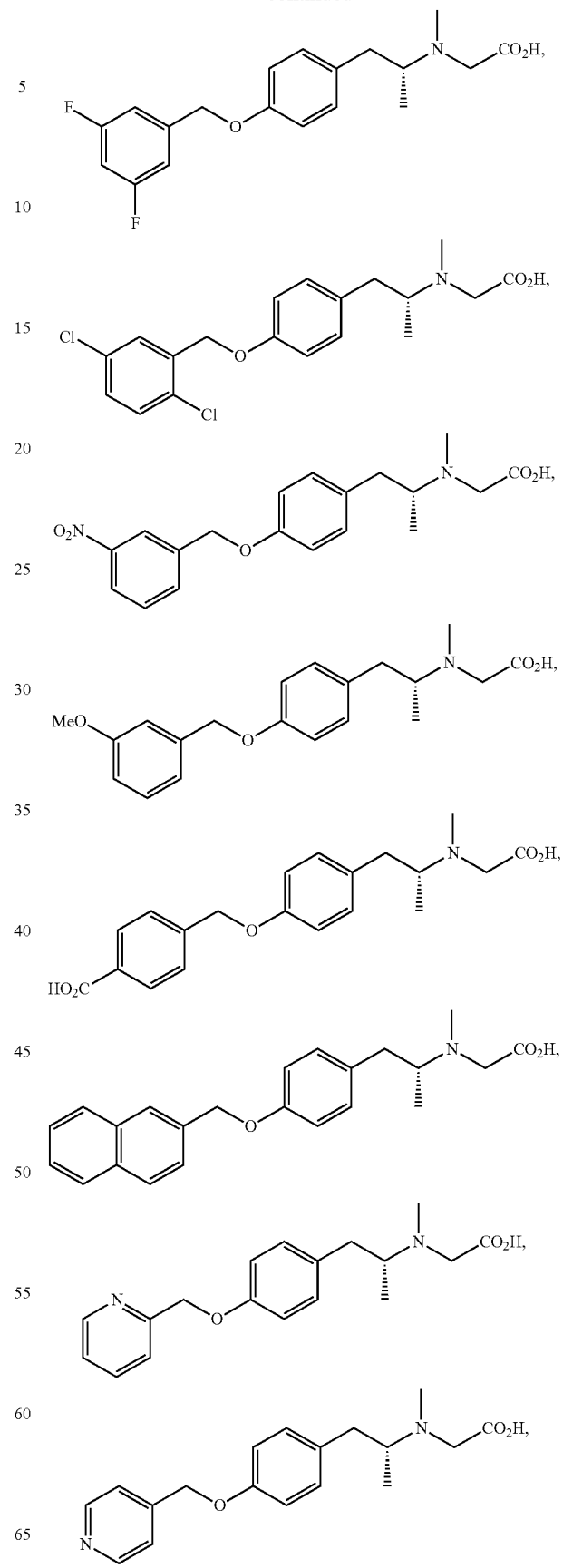

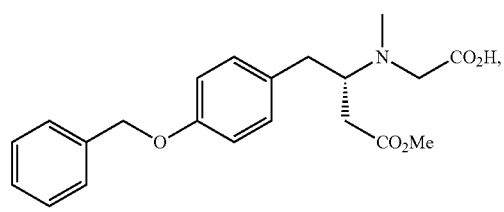
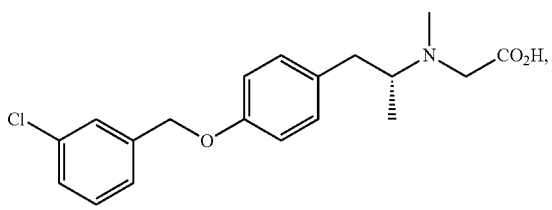
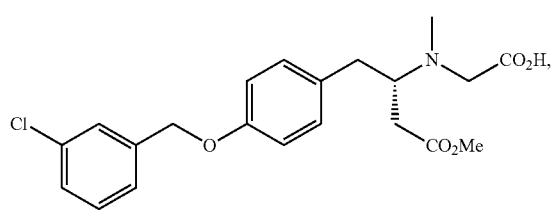
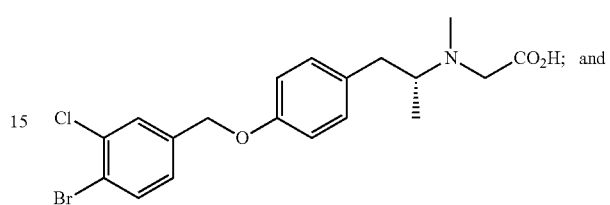
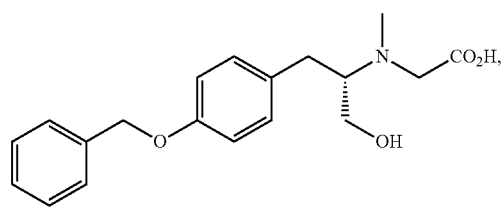
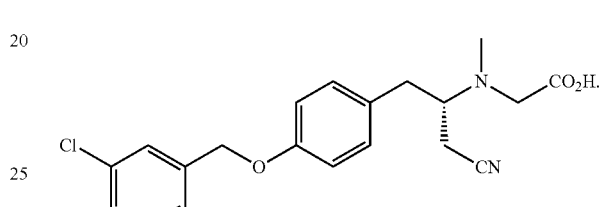
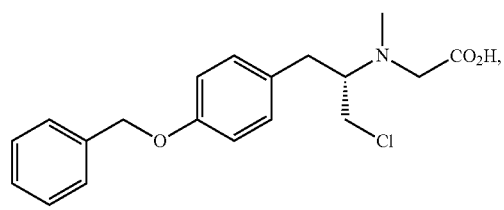
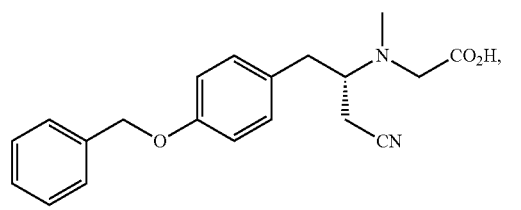
The compound may be selected from one of more of:
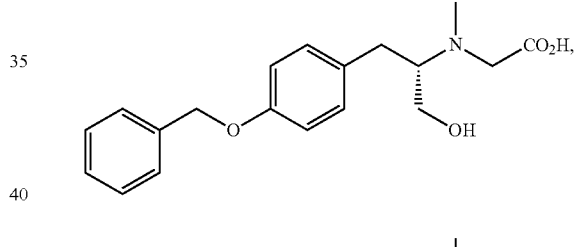
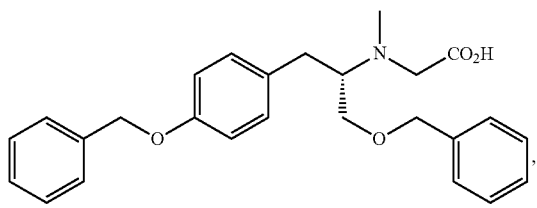
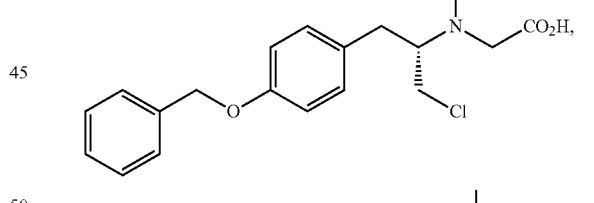
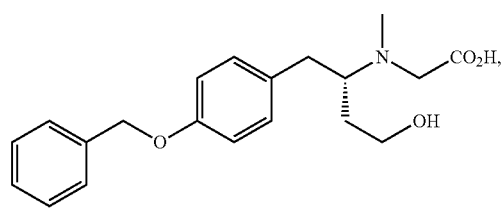
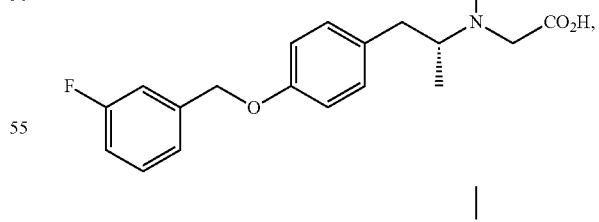
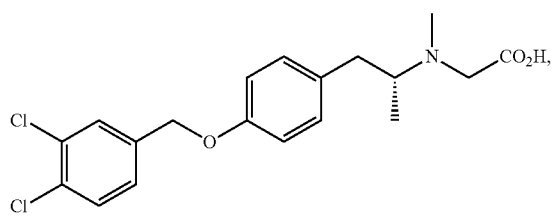
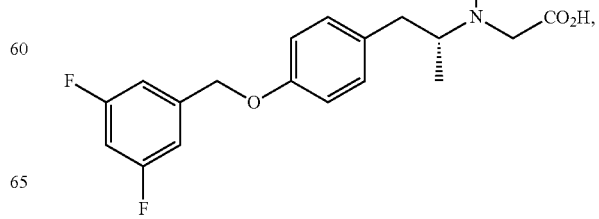

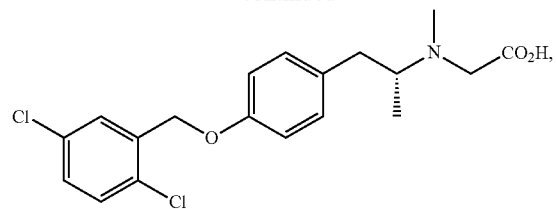

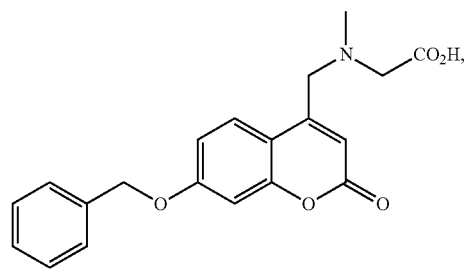

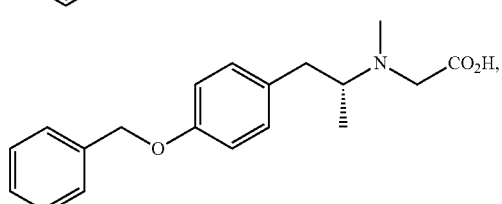

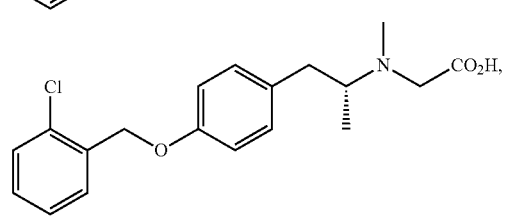

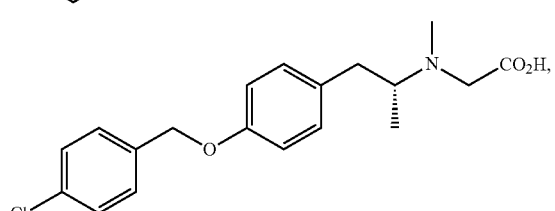

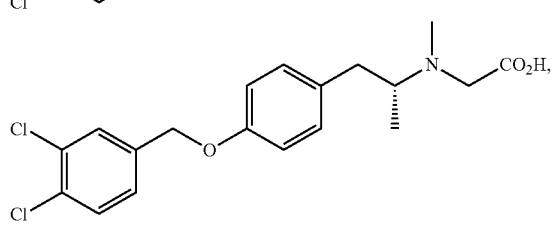

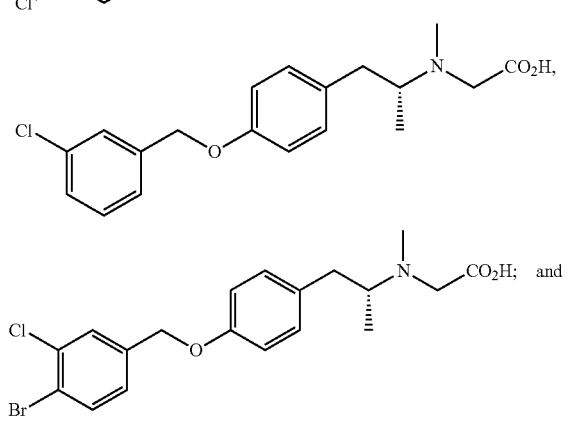

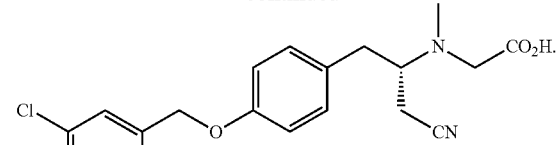

The compound may be selected from one of more of:

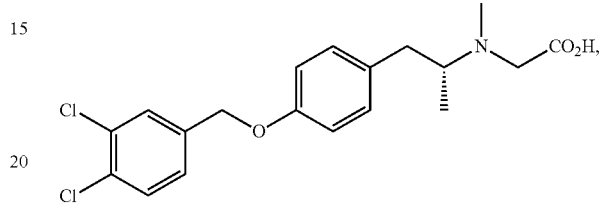

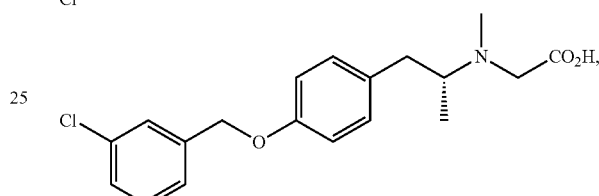

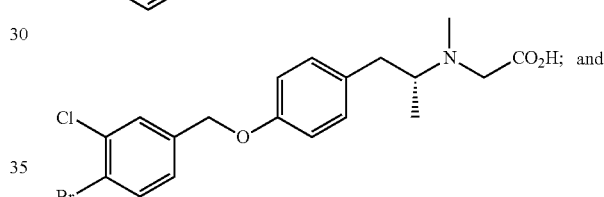

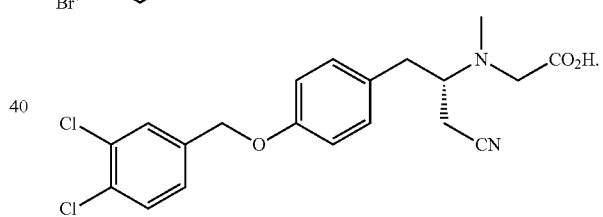

The compound may be

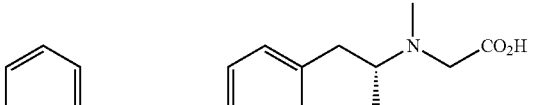

or

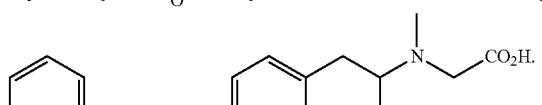

The barrier disease may be septicemia, Crohn's disease, ulcerative colitis, periodontitis, diarrheal disease caused by a pathogenic bacteria or asthma. The cardiometabolic disorders may be hypertension, dyslipidemias, high blood pressure or insulin resistance. The auto-immune and inflammatory disease may be rheumatoid arthritis.

The MAO-B selective inhibitor having a reduced ability to cross the blood brain barrier may be a compound as described herein. The barrier disease may be septicemia, Crohn's disease, ulcerative colitis, periodontitis, diarrheal disease caused by a pathogenic bacteria or asthma. The cardiometabolic disorder may be hypertension, dyslipidemias, high blood pressure or insulin resistance. The autoimmune and inflammatory disease may be rheumatoid arthritis. The MAO-B selective inhibitor having a reduced ability to cross the blood brain barrier may be a compound as described herein. The barrier disease may be septicemia, Crohn's disease, ulcerative colitis, periodontitis, diarrheal disease caused by a pathogenic bacteria or asthma. The cardiometabolic disorder may be hypertension, dyslipidemias, high blood pressure or insulin resistance. The autoimmune and inflammatory disease may be rheumatoid arthritis.

BRIEF DESCRIPTION OF THE DRAWINGS

The invention will now be described in greater detail with reference to the accompanying diagrams.

FIG. 11 shows a comparison of in vitro BBB permeability of deprenyl, cetirizine and de novo synthesized MAO-B inhibitors. Wildtype Madin-Darby canine cells (MDCK-WT) were used to predict CNS permeability of compounds PS-RG0103, PS-RG0216, PS-RG0245 and PS-AD0191. Known CNS permeable and impermeable compounds, deprenyl and cetirizine, respectively, were also tested for comparison. Deprenyl shows high permeability with a calculated apparent permeability ($P_{app}$) of 44.0±2.5 (×10$^{-6}$ cm/s). Cetirizine, an H1-antagonist anti-histamine with low sedative effects due to its diminished potential to cross the blood brain barrier[1], has a low $P_{app}$ value of 1.7±1.3 (×10$^{-6}$ cm/s). For comparison, PS-RG0103, PS-RG0216, PS-RG0245 and PS-AD0191, our de novo synthesized MAO-B inhibitors, also have low $P_{app}$ values of 2.2±0.2, 1.2±0.1, 3.6±0.2 and 7.9±1.4 (×10$^{-6}$ cm/s), respectively. One-way ANOVA analysis with post-hoc Dunnett's multiple comparison test shows that all four de novo synthesized MAO-B inhibitors are significantly less permeable than deprenyl in MDCK-WT cells but PS-RG0103, PS-RG0216 and PS-RG0245 are not different from cetirizine. This experiment was done in triplicates.

[1]Snowman A M and Snyder S H. Cetirizine: actions on neurotransmitter receptors. *J Allergy Clin Immunol.* 1990; 86(6 pt 2): p. 1025-8.

Figure 12C:
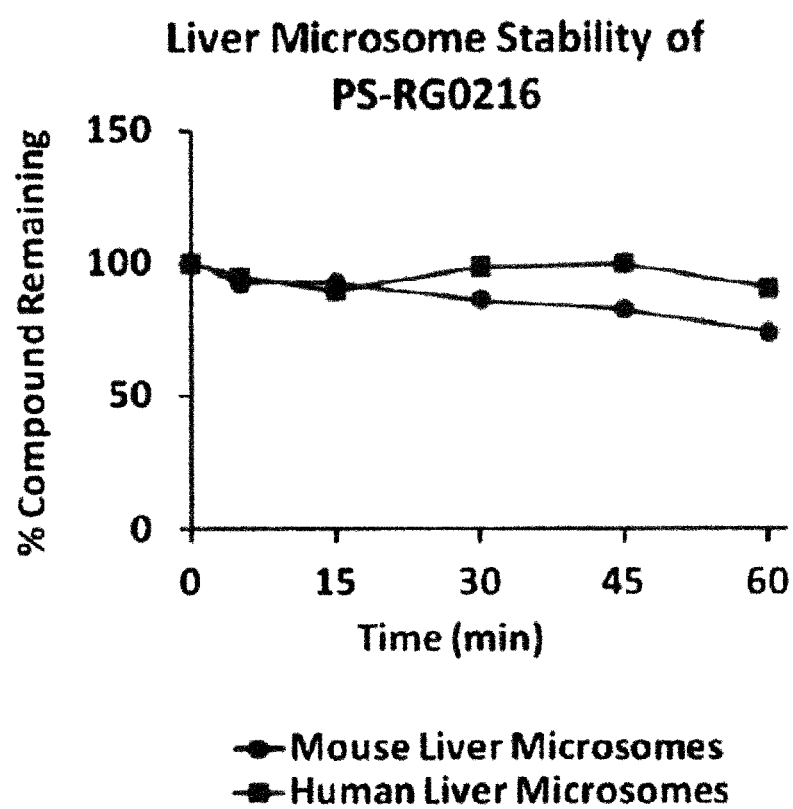

FIGS. 12A-C show stability assay in mouse and human liver microsomes was run on compounds deprenyl, PS-RG0103 and PS-RG0216. (A) Deprenyl, a known selective irreversible MAO-B inhibitor, showed less than 2.5% and 15% in mouse and human microsomes remaining after 60 minutes at room temperature, respectively. Compounds (B) PS-RG0103 and (C) PS-RG0216 showed stability for 60 minutes, resulting in 69% and 74% compound remaining in mouse microsome, respectively and 93% and 91% remaining human microsome, respectively.

Figure 13:
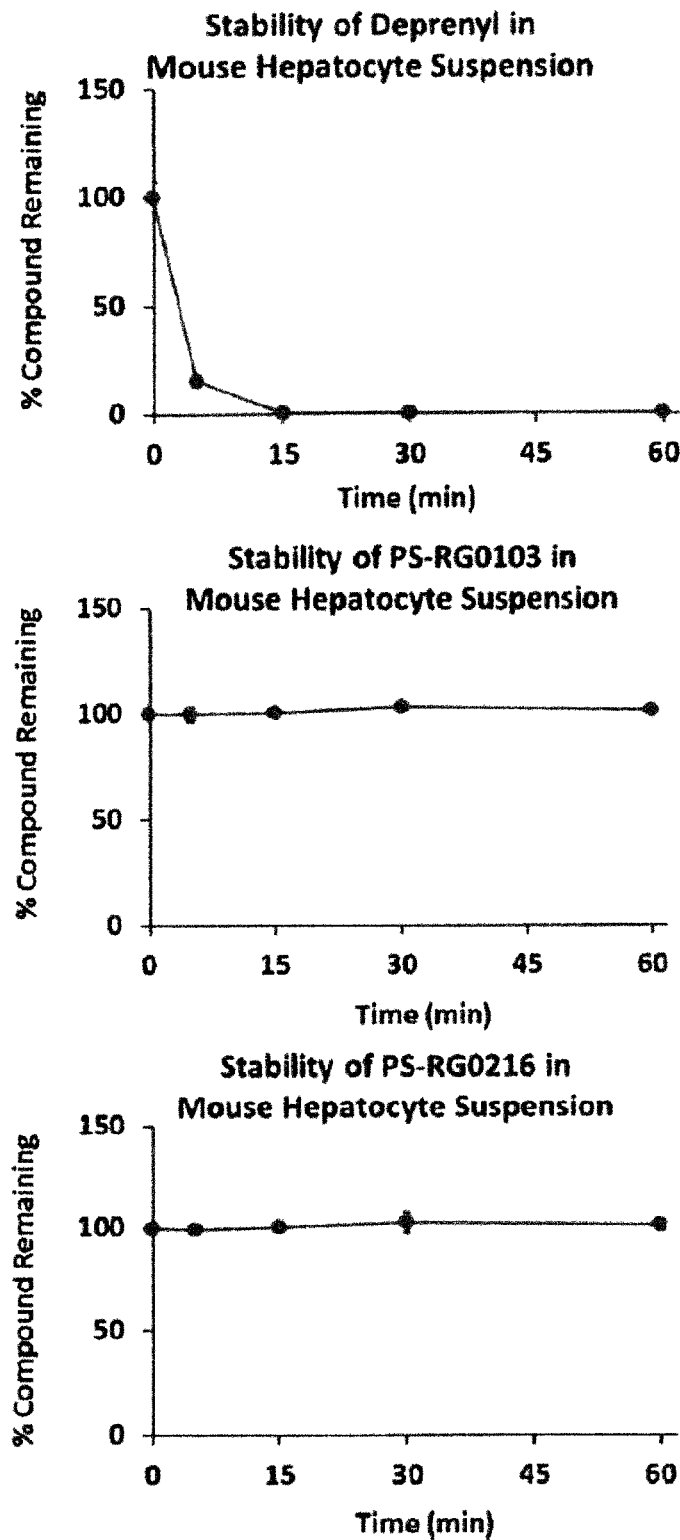

FIG. 13 shows mouse hepatocyte stability assay was performed on compounds deprenyl, PS-RG0103 and PS-RG0216. Deprenyl, a known MAO-B inhibitor, resulted in less than 2.5% remaining after 60 minutes at room temperature. Compounds PS-RG0103 and PS-RG0216 showed stability at 101% and 100%, respectively.

Figure 14:
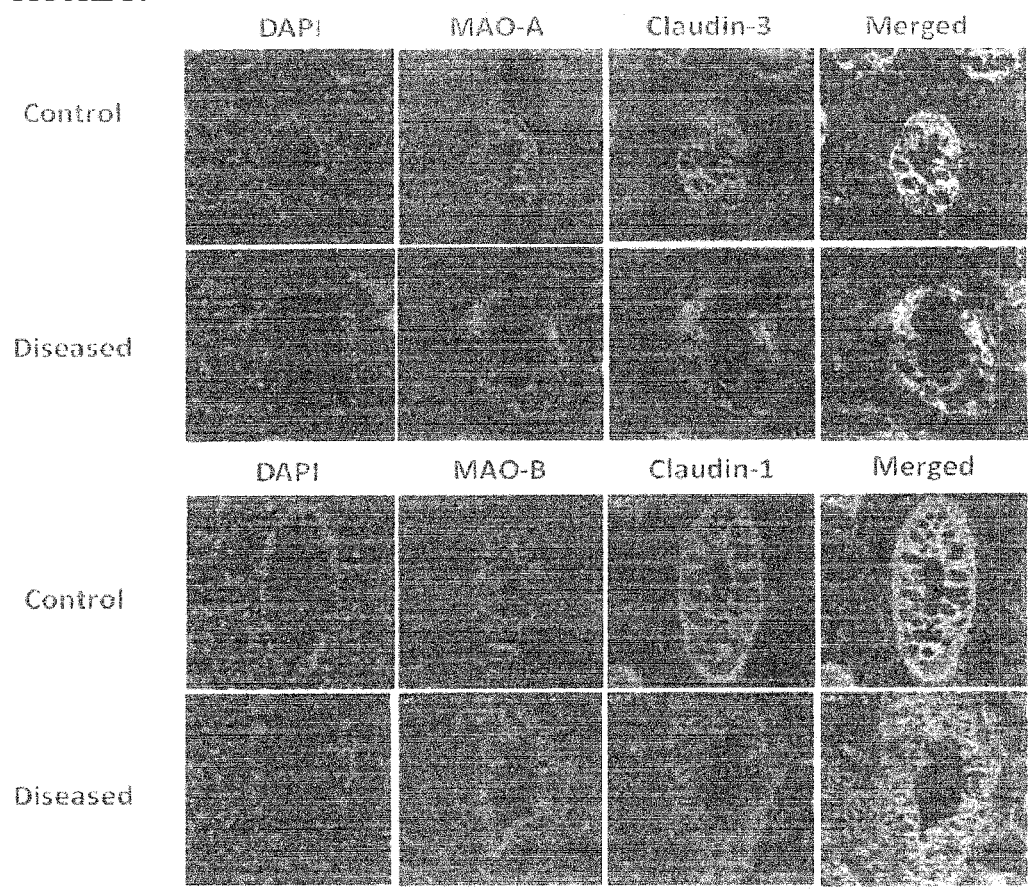

FIG. 14 shows MAO B protein expression preferentially induced in disease sites from patients with Ulcerative Colitis (UC). Punch biopsies were taken from a diseased site and an adjacent non-diseased (control) site of the bowel in patients with ulcerative colitis. The biopsies were flash frozen and embedded in O.C.T. compound in a cryo-mold using a pre-cooled isopentane/liquid nitrogen bath. For immunofluorescence, tissues were fixed in 3% paraformaldehyde and blocked with 5% serum, 0.05% Tween-20 and 0.1% BSA in PBS. Tissue staining for MAO-A were performed using 5 μg/mL of mouse anti-MAO-A antibody (Millipore™, Cat#MABN306), counter-stained with 1.25 μg/mL of rabbit anti-claudin-3 antibody (Invitrogen™, Cat#341700) to highlight epithelial cell tight junctions and labeled with AlexaFluor 594™ goat anti-rabbit IgG (red—not shown) and AlexaFluor 488™ goat anti-mouse IgG (green—not shown) as secondary antibodies, respectively. Tissue staining for MAO-B were performed using 15 μg/mL of rabbit anti-MAO-B antibody (Sigma™, Cat#M1946), counter-stained with 10 μg/mL of mouse anti-claudin-1 antibody (Invitrogen™, Cat#37-4900) to highlight epithelial cell tight junctions, labeled with AlexaFluor 568™ goat anti-mouse IgG (red not shown) and AlexaFluor 488™ goat anti-rabbit IgG (green not shown) as secondary antibodies, respectively and examined using confocal microcopy at 63× magnification. Representative images (from Patient 2) indicates MAO A expression (red) primarily located to epithelial cells (green—not shown) with little change between health and disease sites. In contrast, MAO-B protein expression (red—not shown) was weakly expressed when compared to MAO A expression in non-diseased epithelial cells. However, in disease sites MAO B expression was significantly increased in both the epithelial and connective tissue compartment.

Figure 15:
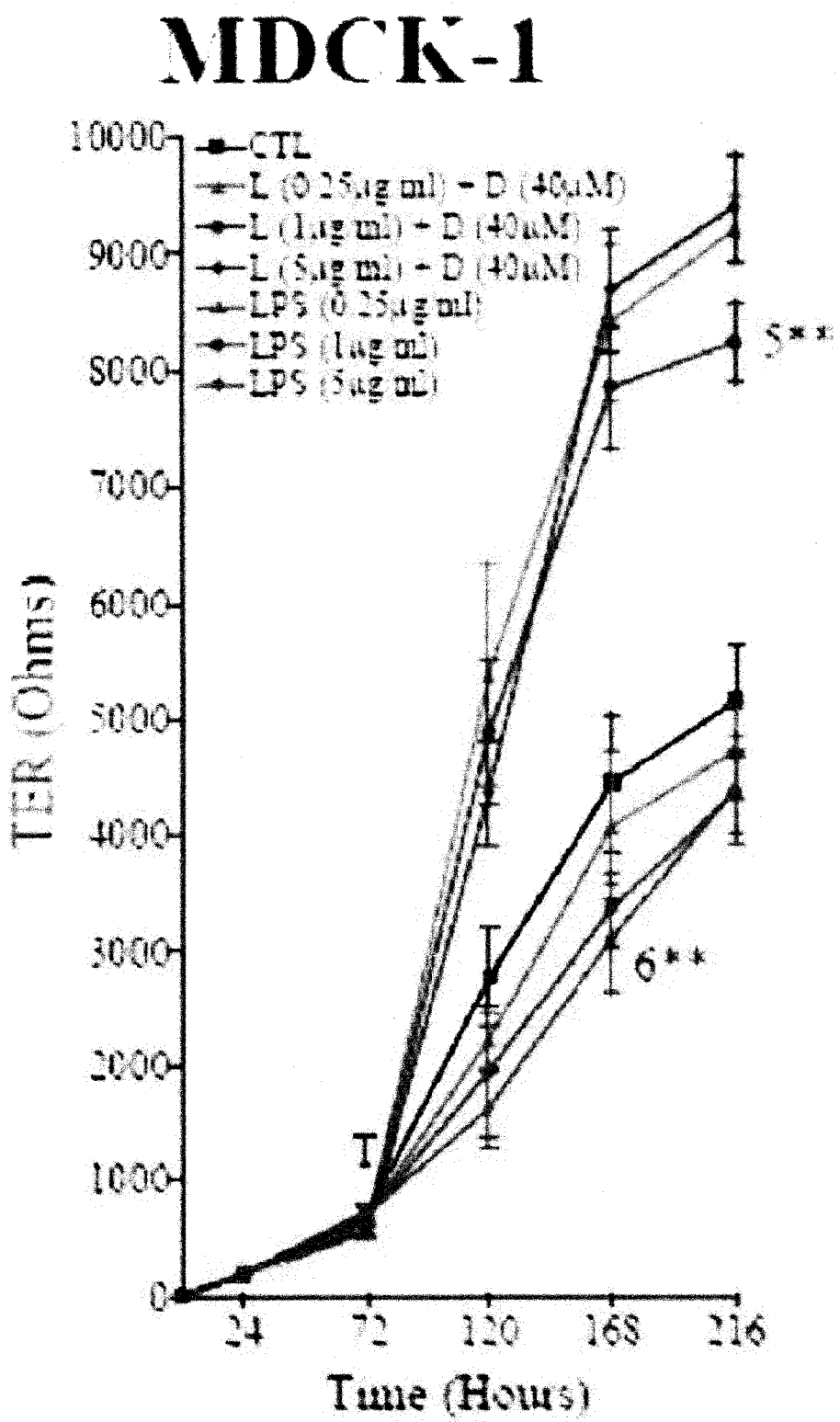

FIGS. 15A-C show deprenyl reduces LPS-induced barrier loss in three epithelial cell lines. Porcine ligament epithelial (PLE), rat intestinal epithelial (IEC-6) and Madin Darby canine kidney (MDCK-I) cell lines cultured in Transwell™ chambers and treated with LPS±deprenyl (D). PLE, IEC-6, and MDCK were challenged at 72 hours (T) with LPS (L)±deprenyl. MDCK-I cultures were treated with a concentration range of LPS and 40 μM deprenyl. In each case, TEER was measured every 48 hours after treatment. Statistically significant differences were identified. Specifically, in all three cell lines, LPS significantly reduced the barrier (TEER) ($p<0.01$) [#s 2, 4, and 6] and LPS+deprenyl significantly induced TEER above control (CTL) ($p<0.01$) [#s 1, 3, and 5].

Figure 16:
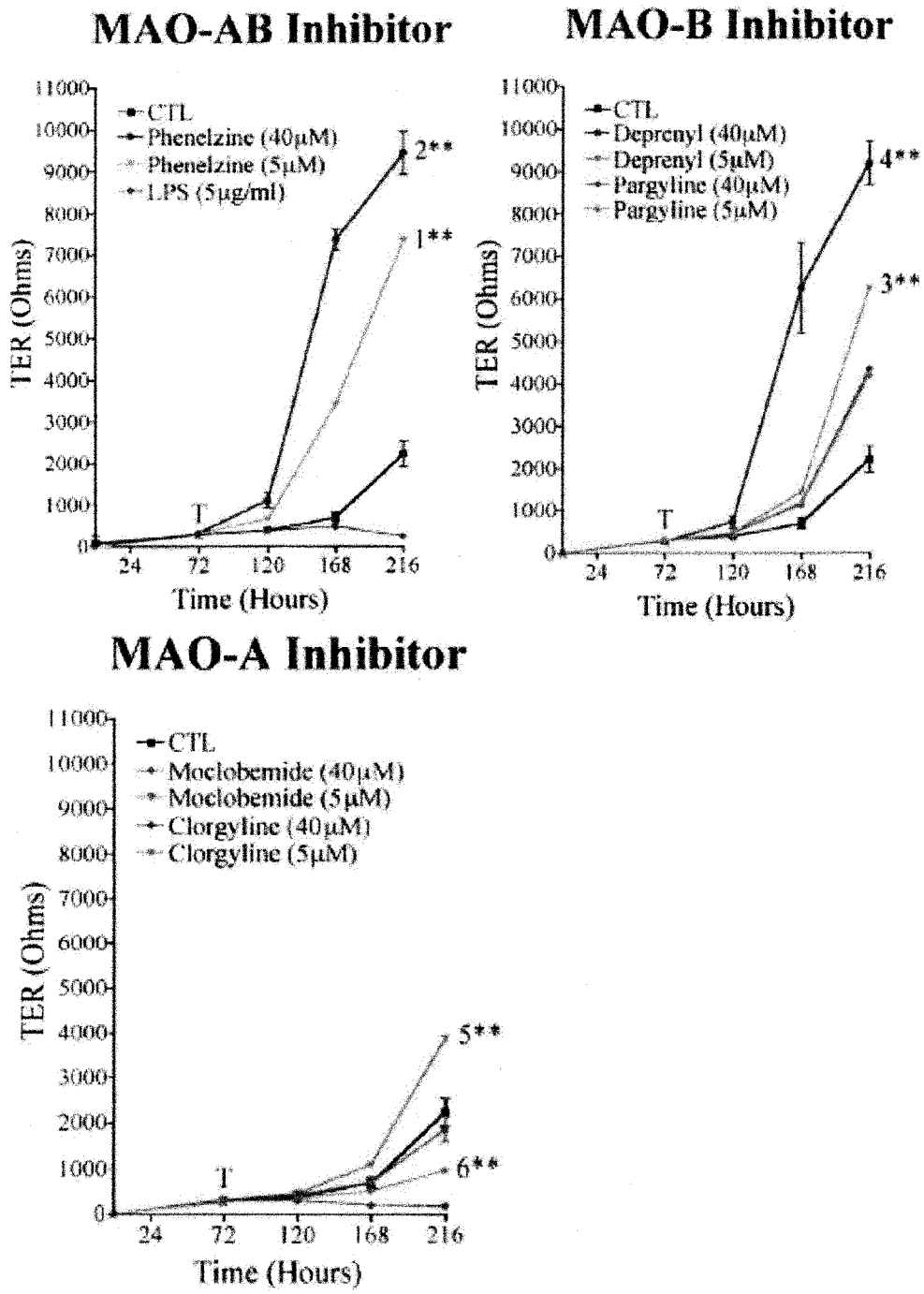

FIG. 16 shows MAO A/B, MAO B and MAO A class inhibitors uniquely impact MDCK-I cell TEER. Transwell cultures were treated at 72 hours (T) post-cell plating. Analysis of 144-hour barrier (TEER) using one-way ANOVA with Tukey post-hoc testing found a significant decrease in TER with LPS ($p<0.01$). TEER was increased over control (CTL) ($p<0.01$) for 5 and 40 μm phenelzine, 5 and 40 μm deprenyl and pargyline, and 5 μm moclobemide. However, 5 and 40 μm clorgyline significantly reduced the barrier ($p<0.01$).

Figure 17:
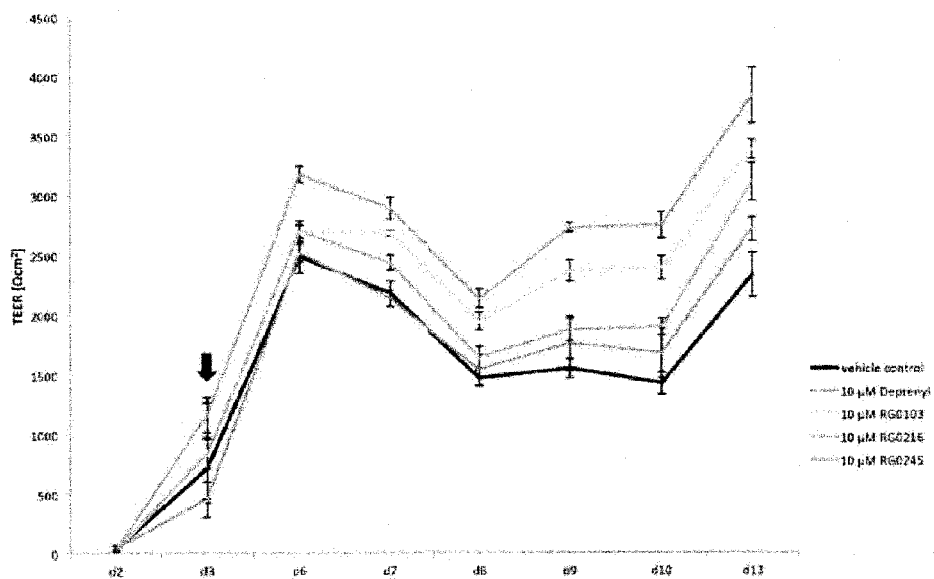

FIG. 17 shows the effect of deprenyl and novel MAO B inhibitors on transepithelial electrical resistance (TEER) in MDCK (NBL-2) cells. (A). MDCK (NBL-2) cells were seeded at 42000 cells/cm$^2$ on 24-well Polyester Transwell inserts in MEM α medium (#12561-056, Gibco™) containing 10% FBS. TEER was measured using a Millicell® ERS-2 voltohmmeter (Millipore™) starting on day 2 after seeding, followed by a change of media. On day 3 TEER was measured and cells were treated with 10 μM deprenyl, RG0103, RG0216, RG0245 or vehicle (H$_2$O) control in complete media (arrow). On days 6, 7, 8, 9, 10 and 13 TEER was measured. Only on days 6 and 8 media including the aforementioned treatments was changed. Data represent the mean±standard deviation (n=4). (B). P values for each day and treatment group compared to vehicle control. Statistical significance was determined using a one-way ANOVA and Tukey post-hoc test in SPSS (IBM).

Figure 18:
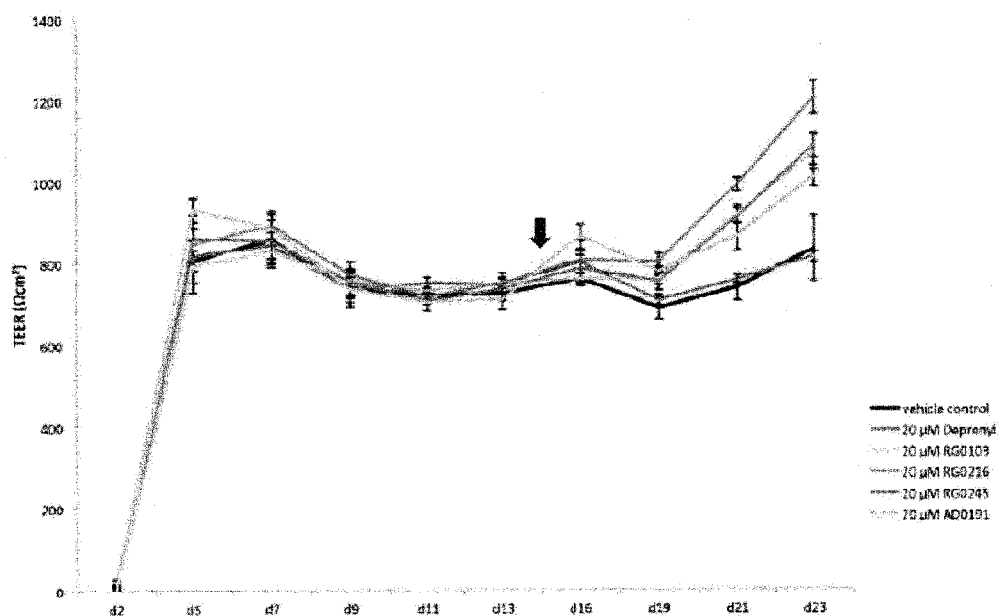

FIG. 18 shows the effect of deprenyl and novel MAO B inhibitors on transepithelial electrical resistance (TEER) in Caco-2 cells. A. Caco-2 cells were seeded at 76000 cells/cm$^2$ on 24-well Polyester Transwell inserts in DMEM medium (#10313-021, Gibco™) containing 10% FBS, 1× GlutaMax (#35050-061, Gibco™) and 1× Penicillin-Streptomycin (#15140-122, Gibco™). TEER was measured using a Millicell® ERS-2 voltohmmeter (Millipore™) starting on day 2 after seeding, followed by a change of media. On days 5, 7, 9, 11 and 13 TEER was measured followed by a media change. On day 14 cells were treated with 20 μM deprenyl, RG0103, RG0216, RG0245, AD0191 or vehicle (H$_2$O) control in complete media (arrow). On days 16, 19, 21 and 23 TEER was measured and media was changed including the aforementioned treatments. Data represent the mean±standard deviation (n=4). B. P values for each day and treatment group compared to vehicle control. Statistical significance was determined using a one-way ANOVA and Tukey post-hoc test in SPSS (IBM).

Figure 19:
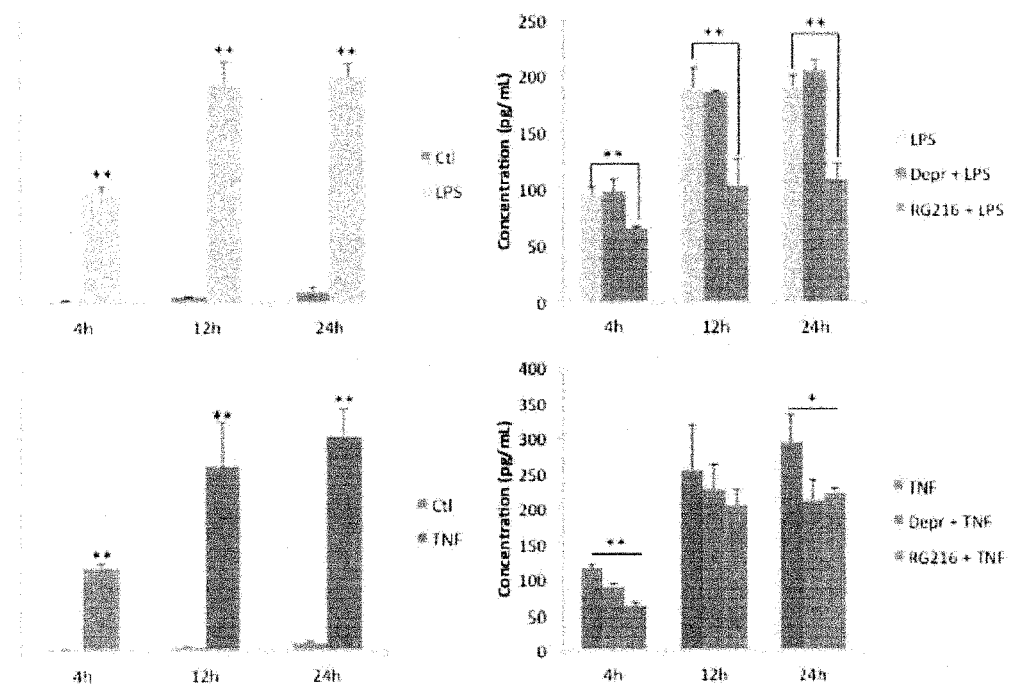

FIG. 19 shows attenuation of IL-8 protein expression in LPS- and TNFα-treated human epithelial colorectal adenocarcinoma cells (Caco-2) by deprenyl and RG0216. Caco-2 cells were seeded at 83300 cells/cm$^2$ on a polystyrene 96-well plate in DMEM medium (#10313-021, Gibco™) containing 10% FBS. On day 5 after seeding, wells were replaced with fresh media containing 2.5% FBS. Cells were treated for 4, 12 or 24 h on day 6 or 7 with 1 μg/mL LPS or 50 ng/mL TNFα alone or 1 μg/mL LPS or TNFα+20 μM deprenyl or RG0216. Supernatants of the treated cells were analyzed for pro- and anti-inflammatory cytokine proteins using the Human Proinflammatory 7-Plex Ultra-Sensitive Kit™ (K15008C, MSD™) measured by the Sector Imager 2400A (MSD™). Left panel: Absolute concentrations of IL-8 protein in supernatants of cells treated with control (media only), 1 μg/mL LPS or 50 ng/mL TNFα. Right panel: Absolute IL-8 concentrations induced or attenuated by 1 μg/mL LPS or 50 ng/mL TNFα±deprenyl or RG0216. Values were determined by subtracting supernatant cytokine concentrations of control from supernatant cytokine concentrations of treated cells. Results are expressed as mean±standard deviation (n=3). Statistical significance was determined using a one-way ANOVA and Tukey post-hoc test in SPSS (IBM™) comparing control and LPS or TNFα (E & F) (top panel) or LPS or TNFα and deprenyl or RG0216 (bottom panel). *$p<0.05$, **$p<0.001$ FIGS. 20A-F show attenuation of IL-8 (A & B), IL-6 (C & D) and TNFα protein expression in LPS-treated human intestinal microvascular endothelial cells (HIMEC) by deprenyl and novel MAO B inhibitors. Human microvascular endothelial cells were seeded at 37500 cells/cm$^2$ on a fibronectin-coated polystyrene 96-well plate in MCDB 131 medium (#10372-019, Gibco™) containing 20% FBS. On day 2 after seeding, wells were replaced with fresh media containing 2.5% FBS. Cells were treated for 1 or 3 hrs on day 3 with 10, 100, 1000 ng/ml LPS alone or 1000 ng/mL LPS+10 μM deprenyl, RG0103, RG0216, RG0245 or AD191. Supernatants of the treated cells were analyzed for pro- and anti-inflammatory cytokine proteins using the Human Proinflammatory 7-Plex Ultra-Sensitive Kit (K15008C, MSD) measured by the Sector Imager 2400A (MSD). Left panel: Absolute concentrations of IL-8, IL-6 and TNFα protein in supernatants of cells treated with control (media only) or increasing concentrations of LPS. Right panel: Absolute IL-8, IL-6 or TNFα concentrations induced or attenuated by 1000 ng/mL LPS±the novel MAO B inhibitors. Values were determined by subtracting supernatant cytokine concentrations of control from supernatant cytokine concentrations of treated cells. Results are expressed as mean±standard deviation (n=3). Statistical significance was determined using a one-way ANOVA and Tukey post-hoc test in SPSS (IBM) comparing control and LPS (left panel) or LPS and novel MAO B inhibitors (right panel). *$p<0.05$, **$p<0.001$ FIGS. 21A and B show a 3% DSS induced colitis and protects epithelial cell-cell claudin-3 localization. Control, deprenyl±DSS treated C57BL/6 mice were treated with 3% DSS in the drinking water and animals sacrificed on day 7. (A). In DSS-treated mice the gross colon images were associated with looser stool and H&E stained sections demonstrated deeper crypts and disorganized epithelium. (B). Control mice demonstrate classical claudin-3 localization that is severely disrupted in DSS-treated animals. In contrast, claudin-3 was better localized to epithelial cell-cell contacts in DSS+deprenyl-treated animals. Increased cell infiltrate is evident in the DSS-treated animals by the DAPI (blue) staining.

Figure 22A:
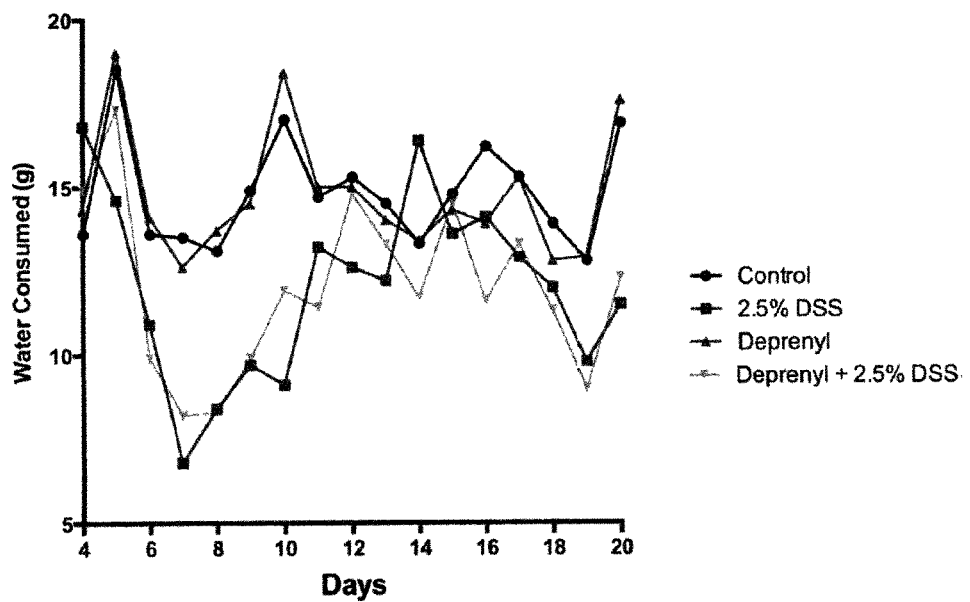
Figure 22B:
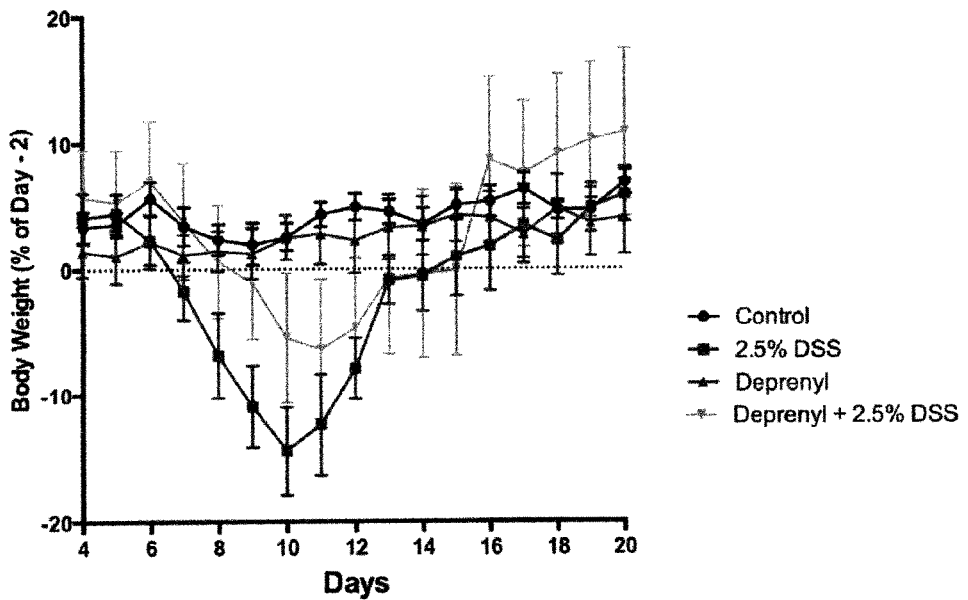

FIGS. 22A and B show the effect of deprenyl on DSS-induced colitis in C57BL/6 mice. Female 8-12 week-old C57BL/6 mice, weighing approximately 20 g, were obtained from Charles River. Colitis was induced with 2.5% DSS (40-50 kDa, Affymetrix™) added to the drinking water for 7 days. From day 8 on, water was given to all groups. Two days prior to DSS treatment mice were subcutaneously injected with 3 mg/kg deprenyl and then once daily for the remainder of the study. Each treatment group consisted of 5 mice housed in one cage. During the entire experiment the drinking solution was weighed prior to being given to the mice and the following day to determine the quantity consumed (A). Daily body weight was measured and calculated by dividing body weight on the specific day by the body weight at day −2. Values are expressed as percent change from day −2 (B).

DETAILED DESCRIPTION

Any terms not directly defined herein shall be understood to have the meanings commonly associated with them as understood within the art of the invention. As employed throughout the specification, the following terms, unless otherwise indicated, shall be understood to have the following meanings.

The inventors have demonstrated that gene and protein expression of monoamine oxidase B (MAO-B), a pro-oxidative enzyme, is increased in models of epithelial barrier disease. In two in vivo models the inventors have shown that clinically-approved MAO inhibitors dramatically improved the barrier, reduced periodontal disease and protected the gastrointestinal tract barrier in a *Citrobacter rodentium* diarrhea model of human pathogenic *E. coli* infection. These findings suggest that MAO inhibitors may be used to manage mucosal diseases. However, in their current form, MAO inhibitors cross the blood-brain barrier (BBB) and thus are associated with significant adverse effects and drug-drug interactions. MAO inhibitors, in particular MAO-B inhibitors that have a reduced ability to cross the BBB, may be useful for treating non-CNS diseases, such as epithelial barrier diseases, without these undesirable side effects as described herein.

As used herein, the term epithelial and endothelial disease means diseases involving epithelial and endothelial cells, respectively. As used herein a barrier disease refers to both epithelial and endothelial disease. In the gastrointestinal (GI) tract, epithelial cells form a barrier to support nutrient and water transport while preventing microbial contamination of the interstitial tissues. Along with plasma membranes, the intercellular tight junction is the primary cellular determinant of epithelial barrier function. Disruption of tight junction structure, as a result of specific protein mutations or aberrant regulatory signals, can be both a cause and an effect of disease. Many GI diseases are characterized as epithelial barrier diseases, including Crohn's disease and ulcerative colitis. Similarly many oral diseases such as periodontitis are epithelial barrier diseases. Other diseases involving epithelial cells may include asthma. Endothelial cell diseases may include LPS-induced endothelial cell hyperpermeability.

Another example of a barrier disease, is septicemia. LPS-induced expression of cytokines/chemokines in endothelial cells was based on a hypothesis that MAO B inhibitors may possibly be used to treat vascular collapse due to septicemia. Septicemia is believed to induce a system wide cytokine storm in endothelial cells that in turn leads to cytokine expression, loss of barrier which may result in vascular collapse Although perhaps not considered a barrier disease, solid epithelial cell tumors are also likely to benefit from MAO-B specific inhibitors, which may also be used to reduce solid epithelial cell tumor metastasis.

It has been reported that treatment with non-selective MAO Inhibitors (phenelzine, and tranylcypromine) may halt, or result in remission of rheumatoid arthritis, potentially via inhibition of PGE2 synthesis (Lieb, (1983) Int J Immunopharmacol. 983; 5(4):353-7; U.S. Pat. No. 4,409, 243; and U.S. Pat. No. 4,490,385) and/or by decreasing Tumor Necrosis Factor-α (TNF-α) levels (Altschuler et al., (2000) Int J Immunopharmacol. 2000 November; 22(11): 1007-8).

Obesity is a chronic medical condition defined by the excess accumulation of adipose tissue. The prevalence of obesity has dramatically increased with the global prevalence nearly doubling in the last 30 years. The World Health Organization reports that in 2008, 10% of men and 14% of women aged 20+ were classified as obese, representing a combined estimated of more than half a billion adults world-wide (WHO, 2013). Obesity frequently results in the development of a number of adverse co-morbidities, including type 2 diabetes, inflammatory diseases (such as rheumatoid arthritis), cardiometabolic disorders, and increases the risk for development of a number of forms of cancer. Obesity is defined as having a body mass index (BMI) of 30 or above. The index is a measure of an individual's body weight relative to height. BMI is calculated by dividing body weight (in kilograms) by height (in meters) squared. Normal and healthy body weight is defined as having a BMI between 20 and 24.9. Treatments targeting obesity focus on reducing the amount of adipose tissue in patients, which in turn reduces BMI levels to a more normal range.

MAO inhibitors have been clinically shown to be useful in the treatment of CNS disorders. However, discovery that they also possess anti-obesity activity via a peripheral (i.e., non-CNS) mechanism, provides a novel approach for the treatment of obesity. MAO enzymes have been identified in a number of peripheral (non-CNS) tissues (Saura et al., (1992) J Neurosci. 12(5):1977-99), with abdominal and mammary human adipocytes possessing high levels of MAO activity (Pizzinat et al., (1999) Biochem Pharmacol. 58(11): 1735-42). Utilizing the non-selective, MAO A/B inhibitor phenelzine, it was shown that it can inhibit MAO activity in adipocytes (Carpéné et al., Pharmacol Res. (2008) 57(6): 426-34). Furthermore, in both obese and non-obese rats, phenelzine inhibited MAO activity, diminished body weight gain, and reduced intra-abdominal adipose tissue (Carpéé et al., Pharmacol Res. (2007) 56(6):522-30; Carpéné et al., Pharmacol Res. (2008) 57(6):426-34).

In further work by Jenrin Discovery, Inc. (US 2007/0078172; US 2014/0155355; U.S. Pat. No. 8,541,475; U.S. Pat. No. 8,138,209; U.S. Pat. No. 7,956,220) it was observed that when compared to untreated controls, rats treated with the selective MAO-B inhibitor L-selegiline demonstrated a 14% lower weight gain over the course of a 14 week study. Significantly, food intake was comparable between the two groups, indicating that the reduced weight gain was not a result of CNS-mediated appetite-suppressant effects. Analysis of individual tissue and organ weights at the conclusion of the study revealed that the reduced weight gain was due almost exclusively to a selective reduction in fat tissue. Assessment of total body fat reveled that compared to control rats, total body fat was reduced by 30% in rats dosed with L-selegiline. Finally, plasma leptin levels, a biomarker for overall adiposity, were significantly reduced (41%) in rats dosed with L-selegiline.

If the CNS effects of MAO inhibitors can be reduced or eliminated, their peripherally mediated anti-obesity properties should allow for their use as clinically relevant therapeutics for the treatment of obesity and the assortment of co-morbidities to which it contributes. Therefore, it is highly desirable to identify find MAO-B inhibitors with limited or no CNS effects. These MAO-B inhibitors are expected to promote weight loss without substantially reducing caloric intake. These inhibitors may be administered in conjunction with an agent designed to function as an appetite suppressant or a lipase inhibitor, which is expected to produce additive or synergistic effects on weight loss. Similarly, co-administration of an MAO-B inhibitor together with one or more other agents shown to be useful for treating the indications described above (e.g., diabetes, cardiometabolic disorders, inflammatory diseases and a combination thereof) is expected to be beneficial, by producing, for example, either additive or synergistic effects.

As used herein, the term 'MAO-B' refers to monoamine oxidase B, an enzyme that in humans is encoded by the MAOB gene, EntrezGene ID: 4129. Monoamine oxidases are a family of enzymes that catalyze the oxidation of monoamines. In humans there are two types, MAO-A and MAO-B.

MAO inhibitors are known in the art (for example, deprenyl and clorgyline and those described in Jenrin Discovery, Inc. in US 2007/0078172, US 2014/0155355, U.S. Pat. No. 8,541,475, U.S. Pat. No. 8,138,209 and U.S. Pat. No. 7,956,220). Furthermore, the present application identifies a number of compounds having the desired activity. The compounds tested are listed below in TABLE 1.

TABLE 1

| Compound Code | Compound Structure | Molecular Formula | MW (g/mol) |
|---|---|---|---|
| Deprenyl | 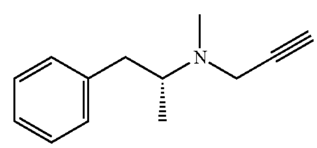 | $C_{13}H_{17}N$ | 187.281 |
| Clorgyline | 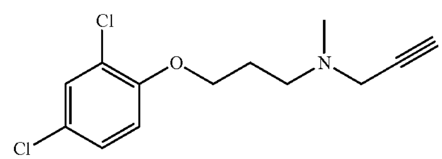 [SMILES: C#CCN(C)CCCOc1ccc(Cl)cc1Cl] | $C_{13}H_{15}Cl_2NO$ | 272.17 |
| PS-AD0031 | 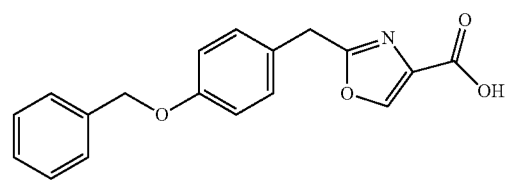 [SMILES: O=C(O)c1coc(Cc2ccc(OCc3ccccc3)cc2)n1] | $C_{18}H_{15}NO_4$ | 309.316 |
| PS-AD0064 | 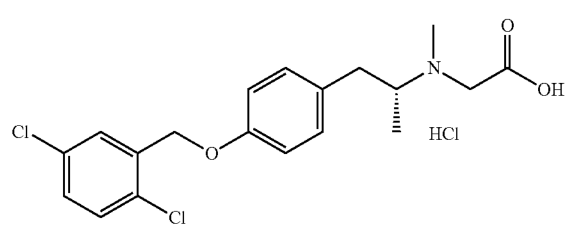 [SMILES: C[C@H](Cc1ccc(OCc2cc(Cl)ccc2Cl)cc1)N(C)CC(=O)O ; Cl] | $C_{19}H_{22}NO_3Cl_3$ | 418.742 |
| PS-AD0065 | 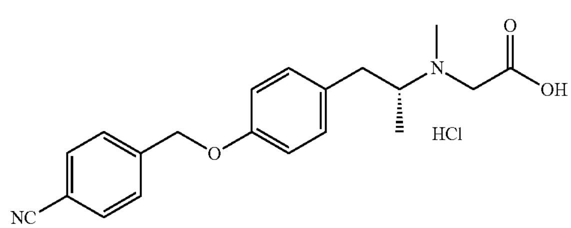 [SMILES: C[C@H](Cc1ccc(OCc2ccc(C#N)cc2)cc1)N(C)CC(=O)O ; Cl] | $C_{20}H_{23}N_2O_3Cl$ | 374.861 |

TABLE 1-continued
Tested Compounds
| Compound Code | Compound Structure | Molecular Formula | MW (g/mol) |
|---|---|---|---|
| PS-AD0065 B | 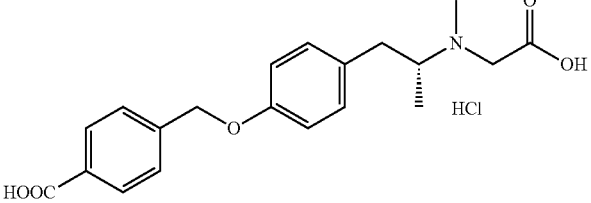 | $C_{20}H_{24}NO_5Cl$ | 393.864 |
| PS-AD0068 | 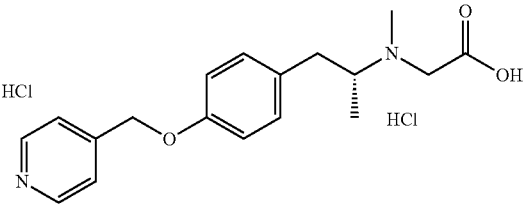 [SMILES: Cl ; C[C@H](Cc1ccc(OCc2ccncc2)cc1)N(C)CC(=O)O ; Cl] | $C_{18}H_{24}N_2O_3Cl_2$ | 387.301 |
| PS-AD0095 | 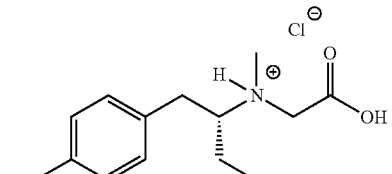 | $C_{19}H_{23}Cl_2NO_3$ | 384.297 |
| PS-AD0179 | 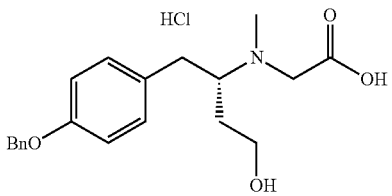 [SMILES: CN(CC(=O)O)[C@H](CCO)Cc1ccc(OCc2ccccc2)cc1 ; Cl] | $C_{20}H_{26}ClNO_4$ | 379.878 |
| PS-AD0186 | 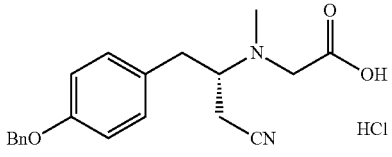 [SMILES: CN(CC(=O)O)[C@H](CC#N)Cc1ccc(OCc2ccccc2)cc1 ; Cl] | $C_{20}H_{23}ClN_2O_3$ | 374.861 |
| PS-AD0191 | 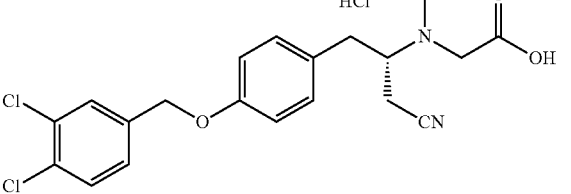 | $C_{20}H_{21}Cl_3N_2O_3$ | 443.751 |
| PS-AD0223 | 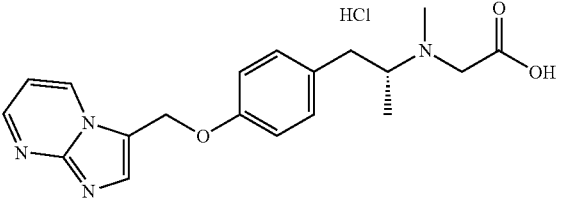 [SMILES: C[C@H](Cc1ccc(OCc2cnc3ncccn23)cc1)N(C)CC(=O)O ; Cl] | $C_{19}H_{23}ClN_4O_3$ | 390.864 |

TABLE 1-continued

Tested Compounds

| Compound Code | Compound Structure | Molecular Formula | MW (g/mol) |
|---|---|---|---|
| PS-RG0008 | (4-phenoxyphenyl)-CH2-CH(CH3)-N(CH3)-CH2-COOH · HCl | $C_{18}H_{22}NO_3Cl$ | 335.825 |
| PS-RG0019 | benzyl-N(CH3)-CH2-COOH · HCl | $C_{10}H_{14}NO_2Cl$ | 215.677 |
| PS-RG0020 | phenethyl-N(CH3)-CH2-COOH · HCl | $C_{11}H_{18}NO_2Cl$ | 229.703 |
| PS-RG0031A | (4-benzyloxyphenyl)-CH2-CH(CH3)-N(CH3)-CH2-COOH · HCl | $C_{19}H_{24}NO_3Cl$ | 349.852 |
| PS-RG0058 | (4-phenoxyphenyl)-CH2-CH2-N(CH3)-CH2-COOH · HCl | $C_{17}H_{20}NO_3Cl$ | 321.799 |
| PS-RG0061 | (4-benzyloxyphenyl)-CH2-CH(CH3)-N(CH3)-CH2-C≡CH · HCl | $C_{20}H_{24}NOCl$ | 329.864 |
| PS-RG0064 | (4-benzyloxyphenyl)-CH2-CH2-N(CH3)-CH2-COOH · HCl | $C_{18}H_{22}NO_3Cl$ | 335.825 |
| PS-RG0070 | phenethyl-N(CH3)-CH2-C≡CH · HCl | $C_{12}H_{16}NCl$ | 209.715 |

TABLE 1-continued
Tested Compounds
| Compound Code | Compound Structure | Molecular Formula | MW (g/mol) |
|---|---|---|---|
| PS-RG0080 | 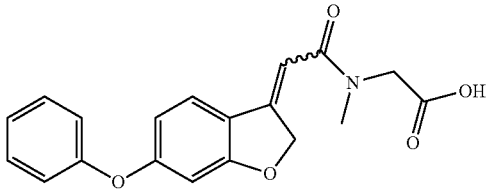 [SMILES: CN(CC(=O)O)C(=O)C=C1COc2cc(Oc3ccccc3)ccc21] | C$_{19}$H$_{17}$NO$_5$ | 339.342 |
| PS-RG0097 | 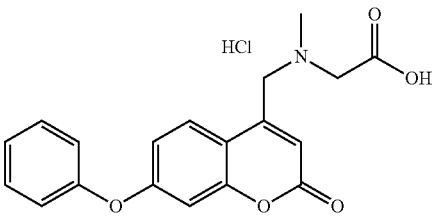 [SMILES: CN(CC(=O)O)Cc1cc(=O)oc2cc(Oc3ccccc3)ccc12 ; Cl] | C$_{19}$H$_{18}$NO$_5$Cl | 379.803 |
| PS-RG0098 | 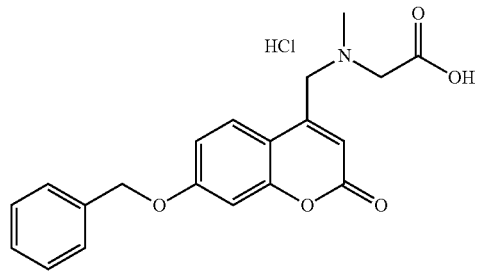 [SMILES: CN(CC(=O)O)Cc1cc(=O)oc2cc(OCc3ccccc3)ccc12 ; Cl] | C$_{20}$H$_{20}$NO$_5$Cl | 389.83 |
| PS-RG0103 | 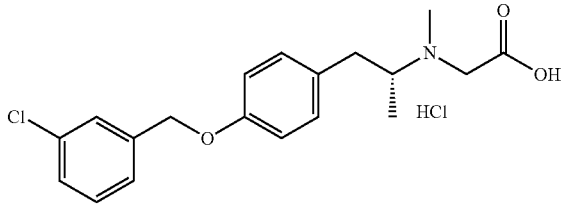 [SMILES: C[C@H](Cc1ccc(OCc2cccc(Cl)c2)cc1)N(C)CC(=O)O ; Cl] | C$_{19}$H$_{23}$NO$_3$Cl$_2$ | 384.297 |
| PS-RG0121 | 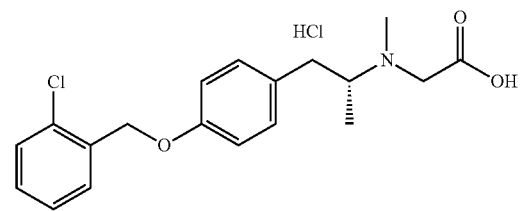 [SMILES: C[C@H](Cc1ccc(OCc2ccccc2Cl)cc1)N(C)CC(=O)O ; Cl] | C$_{19}$H$_{23}$NO$_3$Cl$_2$ | 384.297 |
| PS-RG0122 | 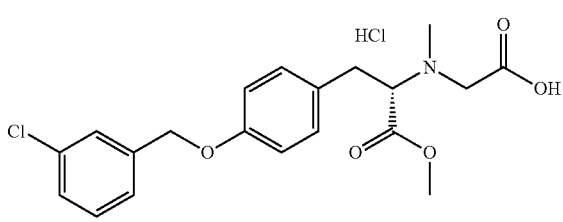 [SMILES: COC(=O)[C@H](Cc1ccc(OCc2cccc(Cl)c2)cc1)N(C)CC(=O)O ; Cl] | C$_{20}$H$_{23}$NO$_5$Cl$_2$ | 428.306 |

TABLE 1-continued

Tested Compounds

| Compound Code | Compound Structure | Molecular Formula | MW (g/mol) |
|---|---|---|---|
| PS-RG0123 | 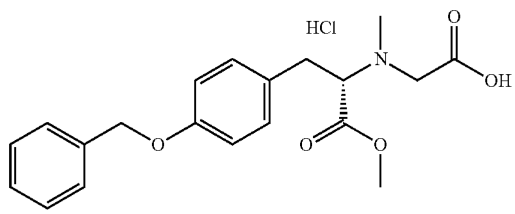 [SMILES: COC(=O)[C@H](Cc1ccc(OCc2ccccc2)cc1)N(C)CC(=O)O ; Cl] | $C_{20}H_{24}NO_5Cl$ | 393.861 |
| PS-RG0128 | 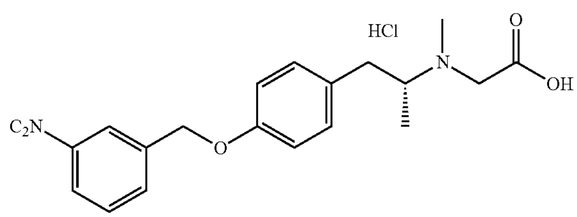 | $C_{19}H_{23}N_2O_5Cl$ | 394.849 |
| PS-RG0171 | 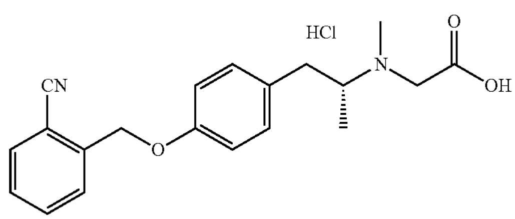 [SMILES: C[C@H](Cc1ccc(OCc2ccccc2C#N)cc1)N(C)CC(=O)O ; Cl] | $C_{20}H_{23}N_2O_3Cl$ | 374.861 |
| PS-RG0172 | 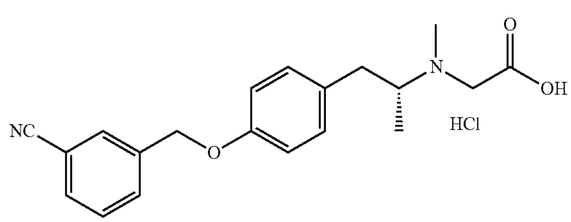 [SMILES: C[C@H](Cc1ccc(OCc2cccc(C#N)c2)cc1)N(C)CC(=O)O ; Cl] | $C_{20}H_{23}N_2O_3Cl$ | 374.861 |
| PS-RG0173 | 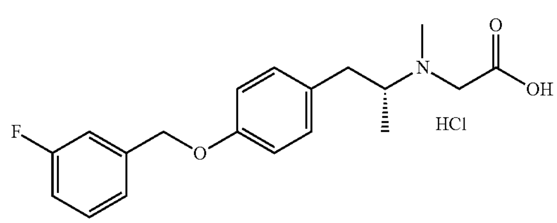 [SMILES: C[C@H](Cc1ccc(OCc2cccc(F)c2)cc1)N(C)CC(=O)O ; Cl] | $C_{19}H_{23}FNO_3Cl$ | 367.842 |
| PS-RG0174 | 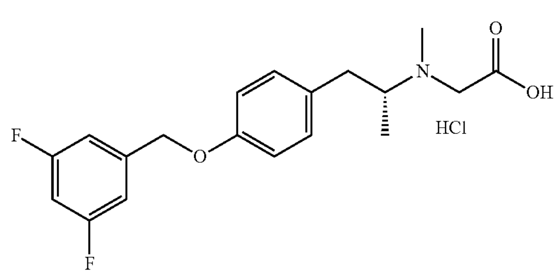 [SMILES: C[C@H](Cc1ccc(OCc2cc(F)cc(F)c2)cc1)N(C)CC(=O)O ; Cl] | $C_{19}H_{22}F_2NO_3Cl$ | 385.833 |

TABLE 1-continued

Tested Compounds

| Compound Code | Compound Structure | Molecular Formula | MW (g/mol) |
|---|---|---|---|
| PS-RG0188 | 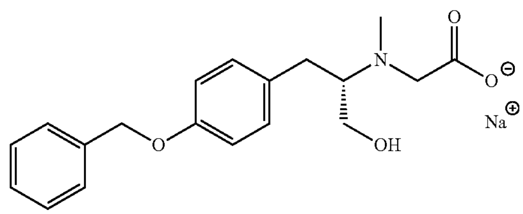 [SMILES: CN(CC(=O)[O-])[C@H](CO)Cc1ccc(OCc2ccccc2)cc1 ; [Na+]] | $C_{19}H_{22}NO_4Na$ | 351.372 |
| PS-RG0200 | 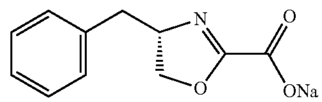 | $C_{11}H_{10}NO_3Na$ | 227.192 |
| PS-RG0210 | 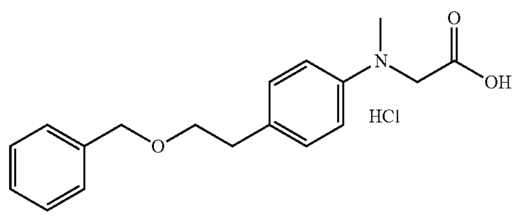 [SMILES: CN(CC(=O)O)c1ccc(CCOCc2ccccc2)cc1 ; Cl] | $C_{18}H_{22}NO_3Cl$ | 335.825 |
| PS-RG0216 | 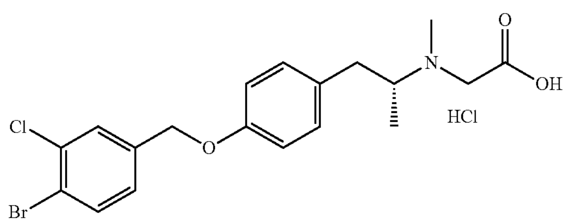 [SMILES: C[C@H](Cc1ccc(OCc2ccc(Br)c(Cl)c2)cc1)N(C)CC(=O)O ; Cl] | $C_{19}H_{22}NO_3BrCl_2$ | 463.193 |
| PS-RG0217 | 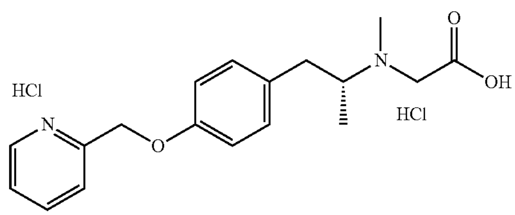 [SMILES: C[C@H](Cc1ccc(OCc2ccccn2)cc1)N(C)CC(=O)O ; Cl ; Cl] | $C_{18}H_{24}N_2O_3Cl_2$ | 387.301 |
| PS-RG0218 | 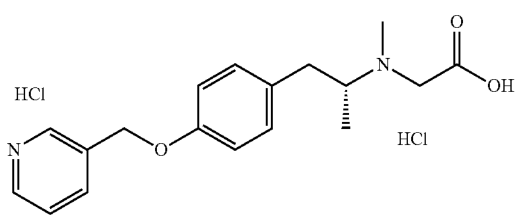 [SMILES: C[C@H](Cc1ccc(OCc2cccnc2)cc1)N(C)CC(=O)O ; Cl ; Cl] | $C_{18}H_{24}N_2O_3Cl_2$ | 387.301 |
| PS-RG0219 | 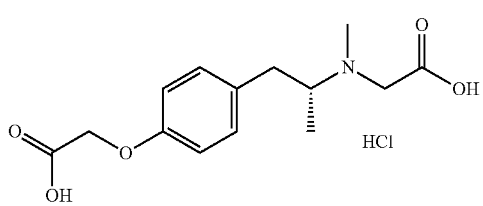 [SMILES: C[C@H](Cc1ccc(OCC(=O)O)cc1)N(C)CC(=O)O ; Cl] | $C_{14}H_{20}NO_5Cl$ | 317.765 |

TABLE 1-continued
Tested Compounds
| Compound Code | Compound Structure | Molecular Formula | MW (g/mol) |
|---|---|---|---|
| PS-RG0221 | 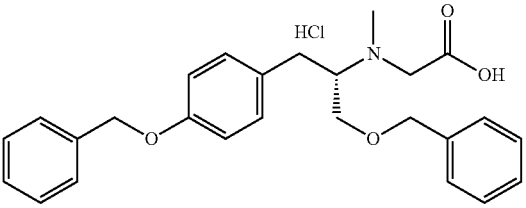 [SMILES: CN(CC(=O)O)[C@H](COCc1ccccc1)Cc1ccc(OCc2ccccc2)cc1 ; Cl] | $C_{26}H_{30}NO_4Cl$ | 455.979 |
| PS-RG0226 | 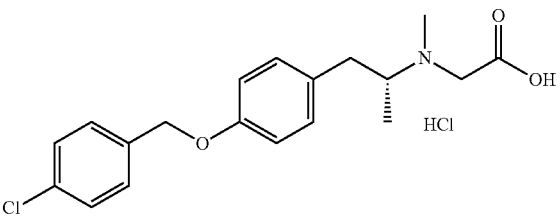 [SMILES: C[C@H](Cc1ccc(OCc2ccc(Cl)cc2)cc1)N(C)CC(=O)O ; Cl] | $C_{19}H_{23}NO_3Cl_2$ | 384.297 |
| PS-RG0227 | 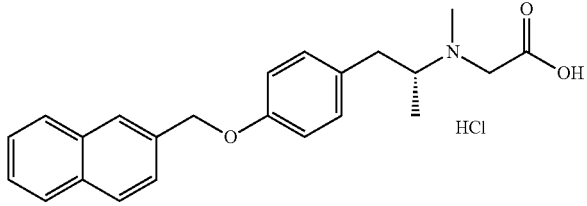 [SMILES: C[C@H](Cc1ccc(OCc2ccc3ccccc3c2)cc1)N(C)CC(=O)O ; Cl] | $C_{23}H_{26}NO_3Cl$ | 399.915 |
| PS-RG0245 | 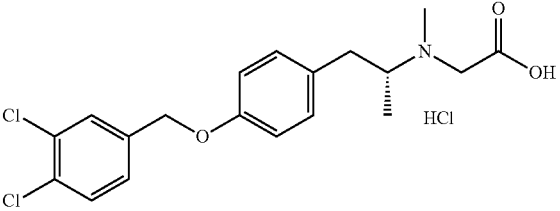 [SMILES: C[C@H](Cc1ccc(OCc2ccc(Cl)c(Cl)c2)cc1)N(C)CC(=O)O ; Cl] | $C_{19}H_{22}NO_3Cl_3$ | 418.739 |
| PS-RG0246 | 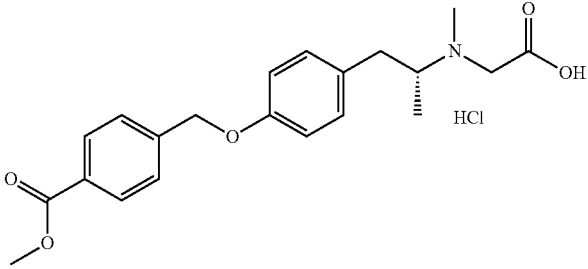 [SMILES: COC(=O)c1ccc(COc2ccc(C[C@@H](C)N(C)CC(=O)O)cc2)cc1 ; Cl] | $C_{21}H_{26}NO_3Cl$ | 407.891 |

TABLE 1-continued

Tested Compounds

| Compound Code | Compound Structure | Molecular Formula | MW (g/mol) |
|---|---|---|---|
| PS-RG0247 | 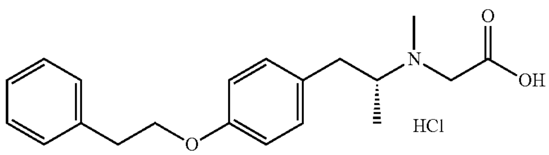 [SMILES: C[C@H](Cc1ccc(OCCc2ccccc2)cc1)N(C)CC(=O)O ; Cl] | $C_{20}H_{26}NO_3Cl$ | 363.882 |
| PS-RG0264 | 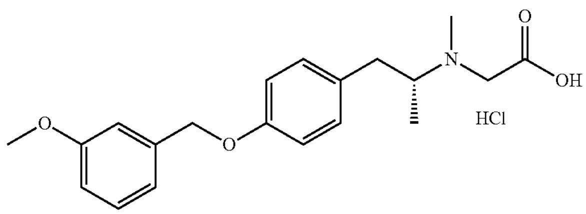 [SMILES: COc1cccc(COc2ccc(C[C@@H](C)N(C)CC(=O)O)cc2)c1 ; Cl] | $C_{20}H_{26}NO_4Cl$ | 379.881 |

It will be understood by a person of skill that COOH and N(R)$_2$ may include the corresponding ions, for example carboxylate ions and ammonium ions, respectively. Alternatively, where the ions are shown, a person of skill in the art will appreciate that the counter ion may also be present.

Those skilled in the art will appreciate that the point of covalent attachment of the moiety to the compounds as described herein may be, for example, and without limitation, cleaved under specified conditions. Specified conditions may include, for example, and without limitation, in vivo enzymatic or non-enzymatic means. Cleavage of the moiety may occur, for example, and without limitation, spontaneously, or it may be catalyzed, induced by another agent, or a change in a physical parameter or environmental parameter, for example, an enzyme, light, acid, temperature or pH. The moiety may be, for example, and without limitation, a protecting group that acts to mask a functional group, a group that acts as a substrate for one or more active or passive transport mechanisms, or a group that acts to impart or enhance a property of the compound, for example, solubility, bioavailability or localization.

In some embodiments, compounds of Formula I and Formula II above may be used for systemic treatment of at least one indication selected from the group consisting of: inflammatory bowel diseases (for example, Crohn's disease, ulcerative colitis), periodontal diseases, asthma and LPS-induced endothelial cell hyperpermeability. In some embodiments compounds of Formula I or Formula II may be used in the preparation of a medicament or a composition for systemic treatment of an indication described herein. In some embodiments, methods of systemically treating any of the indications described herein are also provided.

Compounds as described herein may be in the free form or in the form of a salt thereof. In some embodiment, compounds as described herein may be in the form of a pharmaceutically acceptable salt, which are known in the art (Berge S. M. et al., *J. Pharm. Sci.* (1977) 66(1):1-19). Pharmaceutically acceptable salt as used herein includes, for example, salts that have the desired pharmacological activity of the parent compound (salts which retain the biological effectiveness and/or properties of the parent compound and which are not biologically and/or otherwise undesirable). Compounds as described herein having one or more functional groups capable of forming a salt may be, for example, formed as a pharmaceutically acceptable salt. Compounds containing one or more basic functional groups may be capable of forming a pharmaceutically acceptable salt with, for example, a pharmaceutically acceptable organic or inorganic acid. Pharmaceutically acceptable salts may be derived from, for example, and without limitation, acetic acid, adipic acid, alginic acid, aspartic acid, ascorbic acid, benzoic acid, benzenesulfonic acid, butyric acid, cinnamic acid, citric acid, camphoric acid, camphorsulfonic acid, cyclopentanepropionic acid, diethylacetic acid, digluconic acid, dodecylsulfonic acid, ethanesulfonic acid, formic acid, fumaric acid, glucoheptanoic acid, gluconic acid, glycerophosphoric acid, glycolic acid, hemisulfonic acid, heptanoic acid, hexanoic acid, hydrochloric acid, hydrobromic acid, hydriodic acid, 2-hydroxyethanesulfonic acid, isonicotinic acid, lactic acid, malic acid, maleic acid, malonic acid, mandelic acid, methanesulfonic acid, 2-napthalenesulfonic acid, naphthalenedisulphonic acid, p-toluenesulfonic acid, nicotinic acid, nitric acid, oxalic acid, pamoic acid, pectinic acid, 3-phenylpropionic acid, phosphoric acid, picric acid, pimelic acid, pivalic acid, propionic acid, pyruvic acid, salicylic acid, succinic acid, sulfuric acid, sulfamic acid, tartaric acid, thiocyanic acid or undecanoic acid. Compounds containing one or more acidic functional groups may be capable of forming pharmaceutically acceptable salts with a pharmaceutically acceptable base, for example, and without limitation, inorganic bases based on alkaline metals or alkaline earth metals or organic bases such as primary amine compounds, secondary amine compounds, tertiary amine compounds, quaternary amine compounds, substituted amines, naturally occurring substituted amines, cyclic amines or basic ion-exchange resins Pharmaceutically acceptable salts may be derived from, for example, and without limitation, a hydroxide, carbonate, or bicarbonate of a pharmaceutically acceptable metal cation such as ammonium, sodium, potassium, lithium, calcium, magnesium, iron, zinc, copper, manganese or aluminum, ammonia, benzathine, meglumine, methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, glucamine, methylglucamine, theobromine, purines, piperazine, piperidine, procaine, N-ethylpiperidine, theobromine, tetramethylammonium compounds, tetraethylammonium compounds, pyridine, N,N-dimethylaniline, N-methylpiperidine, morpholine, N-methylmorpholine, N-ethylmorpholine, dicyclohexylamine, dibenzylamine, N,N-dibenzylphenethylamine, 1-ephenamine, N,N'-dibenzylethylenediamine or polyamine resins. In some embodiments, compounds as described herein may contain both acidic and basic groups and may be in the form of inner salts or zwitterions, for example, and without limitation, betaines. Salts as described herein may be prepared by conventional processes known to a person skilled in the art, for example, and without limitation, by reacting the free form with an organic acid or inorganic acid or base, or by anion exchange or cation exchange from other salts. Those skilled in the art will appreciate that preparation of salts may occur in situ during isolation and purification of the compounds or preparation of salts may occur by separately reacting an isolated and purified compound.

In some embodiments, compounds and all different forms thereof (e.g. free forms, salts, polymorphs, isomeric forms) as described herein may be in the solvent addition form, for example, solvates. Solvates contain either stoichiometric or non-stoichiometric amounts of a solvent in physical association the compound or salt thereof. The solvent may be, for example, and without limitation, a pharmaceutically acceptable solvent. For example, hydrates are formed when the solvent is water or alcoholates are formed when the solvent is an alcohol.

In some embodiments, compounds and all different forms thereof (e.g. free forms, salts, solvates, isomeric forms) as described herein may include crystalline and amorphous forms, for example, polymorphs, pseudopolymorphs, conformational polymorphs, amorphous forms, or a combination thereof. Polymorphs include different crystal packing arrangements of the same elemental composition of a compound. Polymorphs usually have different X-ray diffraction patterns, infrared spectra, melting points, density, hardness, crystal shape, optical and electrical properties, stability and/or solubility. Those skilled in the art will appreciate that various factors including recrystallization solvent, rate of crystallization and storage temperature may cause a single crystal form to dominate.

In some embodiments, compounds and all different forms thereof (e.g. free forms, salts, solvates, polymorphs) as described herein include isomers such as geometrical isomers, optical isomers based on asymmetric carbon, stereoisomers, tautomers, individual enantiomers, individual diastereomers, racemates, diastereomeric mixtures and combinations thereof, and are not limited by the description of the formula illustrated for the sake of convenience.

In some embodiments, pharmaceutical compositions as described herein may comprise a salt of such a compound, preferably a pharmaceutically or physiologically acceptable salt. Pharmaceutical preparations will typically comprise one or more carriers, excipients or diluents acceptable for the mode of administration of the preparation, be it by injection, inhalation, topical administration, lavage, or other modes suitable for the selected treatment. Suitable carriers, excipients or diluents (used interchangeably herein) are those known in the art for use in such modes of administration.

Suitable pharmaceutical compositions may be formulated by means known in the art and their mode of administration and dose determined by the skilled practitioner. For parenteral administration, a compound may be dissolved in sterile water or saline or a pharmaceutically acceptable vehicle used for administration of non-water soluble compounds such as those used for vitamin K. For enteral administration, the compound may be administered in a tablet, capsule or dissolved in liquid form. The tablet or capsule may be enteric coated, or in a formulation for sustained release. Many suitable formulations are known, including, polymeric or protein microparticles encapsulating a compound to be released, ointments, pastes, gels, hydrogels, or solutions which can be used topically or locally to administer a compound. A sustained release patch or implant may be employed to provide release over a prolonged period of time. Many techniques known to one of skill in the art are described in *Remington: the Science & Practice of Pharmacy* by Alfonso Gennaro, $20^{th}$ ed., Lippencott Williams & Wilkins, (2000). Formulations for parenteral administration may, for example, contain excipients, polyalkylene glycols such as polyethylene glycol, oils of vegetable origin, or hydrogenated naphthalenes. Biocompatible, biodegradable lactide polymer, lactide/glycolide copolymer, or polyoxyethylene-polyoxypropylene copolymers may be used to control the release of the compounds. Other potentially useful parenteral delivery systems for modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Compounds or pharmaceutical compositions as described herein or for use as described herein may be administered by means of a medical device or appliance such as an implant, graft, prosthesis, stent, etc. Also, implants may be devised which are intended to contain and release such compounds or compositions. An example would be an implant made of a polymeric material adapted to release the compound over a period of time.

An "effective amount" of a pharmaceutical composition as described herein includes a therapeutically effective amount or a prophylactically effective amount. A "therapeutically effective amount" refers to an amount effective, at dosages and for periods of time necessary, to achieve the desired therapeutic result, such as reduced tumor size, increased life span or increased life expectancy. A therapeutically effective amount of a compound may vary according to factors such as the disease state, age, sex, and weight of the subject, and the ability of the compound to elicit a desired response in the subject. Dosage regimens may be adjusted to provide the optimum therapeutic response. A therapeutically effective amount is also one in which any toxic or detrimental effects of the compound are outweighed by the therapeutically beneficial effects. A "prophylactically effective amount" refers to an amount effective, at dosages and for periods of time necessary, to achieve the desired prophylactic result, such as smaller tumors, increased life span, increased life expectancy or prevention of the progression of prostate cancer to an androgen-independent form. Typically, a prophylactic dose is used in subjects prior to or at an earlier stage of disease, so that a prophylactically effective amount may be less than a therapeutically effective amount.

It is to be noted that dosage values may vary with the severity of the condition to be alleviated. For any particular subject, specific dosage regimens may be adjusted over time according to the individual need and the professional judgment of the person administering or supervising the administration of the compositions. Dosage ranges set forth herein are exemplary only and do not limit the dosage ranges that may be selected by medical practitioners. The amount of active compound(s) in the composition may vary according to factors such as the disease state, age, sex, and weight of the subject. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage.

In some embodiments, compounds and all different forms thereof as described herein may be used, for example, and without limitation, in combination with other treatment methods for at least one indication selected from the group consisting of: inflammatory bowel diseases (including Crohn's disease, ulcerative colitis, periodontal diseases, asthma and LPS-induced endothelial cell hyperpermeability.

In general, compounds as described herein should be used without causing substantial toxicity. Toxicity of the compounds as described herein can be determined using standard techniques, for example, by testing in cell cultures or experimental animals and determining the therapeutic index, i.e., the ratio between the LD50 (the dose lethal to 50% of the population) and the LD100 (the dose lethal to 100% of the population). In some circumstances however, such as in severe disease conditions, it may be appropriate to administer substantial excesses of the compositions. Some compounds as described herein may be toxic at some concentrations. Titration studies may be used to determine toxic and non-toxic concentrations. Toxicity may be evaluated by examining a particular compound's or composition's specificity across cell lines Animal studies may be used to provide an indication if the compound has any effects on other tissues.

Compounds as described herein may be administered to a subject. As used herein, a "subject" may be a human, non-human primate, rat, mouse, cow, horse, pig, sheep, goat, dog, cat, etc. The subject may be suspected of having or at risk for having a disease associated with MAO-B. The disease may be an epithelial or endothelial disease. The disease may be selected from inflammatory bowel diseases (including Crohn's disease, ulcerative colitis), periodontal diseases, asthma and LPS-induced endothelial cell hyperpermeability.

General Methodologies

Synthesized MAO B compounds are analyzed using a three step screen. (1) a cell free assay is used to determine enzyme activity and selectivity; (2) compounds move to a bank of cell culture assays to examine viability, cytotoxicity and apoptosis; (3) compounds then move to a second bank of cell culture based assays to examine positive barrier protection effects and lack of penetration across a cell culture based blood brain barrier model.

1) Cell Free Enzyme Assay

MAO B specific inhibitory activity and selectivity over MAO A is assayed using a commercial kit [Fluoro MAO A and B detection kit (Cell Technology Inc™)]. This kit uses a non-fluorescent detection reagent to measure $H_2O_2$ released from the conversion of an MAO A and MAO B substrate specific to its aldehyde. Furthermore, $H_2O_2$ oxidizes the detection reagent in a 1:1 stoichiometry to produce a fluorescent product (resorufin). MAO B and A activity is screened for in relation to deprenyl. This information is then provided to the medicinal chemists to help direct synthesis of subsequent iterations. Targets demonstrating a selectivity index (SI)=MAO B/MAO A>100 and IC 50 activity between 1 and 300 nm are then screened using cell based assays.

2) Cell Based Assay (Viability, Cytotoxicity, Apoptosis)

Inhibitors identified in the cell free enzyme activity screen are tested for toxicity using the ApoTox-Glo™ Triplex Assay (Promega™). Madine Darby Canine Kidney (MDCK-I) cells and CaCo 2 intestinal epithelial cells (model for GI tissues) are screened using this assay. Briefly 20,000 cells are plated into 96-well plates and treated with deprenyl or novel MAO B inhibitors±LPS or H2O2, and cell viability (400Ex/505Em) and cytotoxicity (485Ex/520Em) assayed following the manufacturers' protocols. Caspase-3 and -7 activity (marker of apoptosis) are then detected by the addition of Caspase-Glo 3/7. Deprenyl and novel MAO B inhibitors are tested over a wide concentration and time range.

3a) Analysis of Epithelial Cell Barrier Formation, Disruption and MAO B Inhibitor Protection Transepithelial Resistance (TER) is a common method to screen for barrier integrity. Equal micromolar concentrations of control, deprenyl (positive control), and novel MAO B inhibitors±LPS are added and TER is assayed over 6 days. For select compounds barrier integrity and protection is also measured using tracer studies because TER accuracy in examining TJ integrity has recently come into question (Van Itallie et al., 2008). Fluorescein isothiocyanate conjugated 10 kD dextran (Invitrogen™) will be added to the apical Transwell™ compartment, fixed, and examined for dextran permeation (Umeda et al., 2006). We expect control and deprenyl-treated cells with an intact barrier to maintain the tracer at the apical membrane region, whereas the breached monolayers will show tracer permeation between the cells.

3b) Analysis of BBB Permeability

Novel MAO B inhibitors selected based on the above screening program will be screened using an in vitro model of blood brain barrier (BBB). Madin-Darby canine kidney (MDCK-WT) and MDCK cells transfected with the human MDR1 gene (MDCK-MDR1) are well established in vitro models used to predict a compound's ability to permeate the blood brain barrier (BBB). The MDCK-MDR1 cells are especially useful, as it is transfected with MDR1, the gene that codes for human P-glycoprotein (P-gp), a major efflux transporter that prevents toxic materials, including therapeutic compounds, from going into the brain. Apparent permeability ($P_{app}$), Efflux ratio ($P_{app\ B-A}/P_{app\ A-B}$), as well as the Net flux ratio (Efflux ratio$_{MDCK-MDR1}$/Efflux ratio$_{MDCK-WT}$) can be calculated to identify compound BBB permeability and identify compounds that are substrates of P-gp.

Various alternative embodiments and examples are described herein. These embodiments and examples are illustrative and should not be construed as limiting the scope of the invention.

Experimental Procedures Accompanying FIGS. 1 to 6

Figure 1:
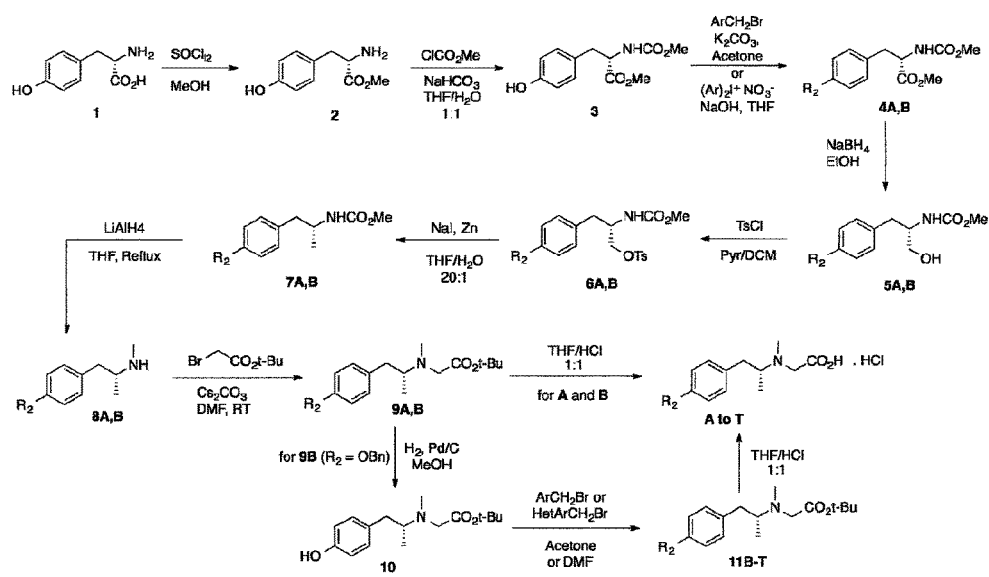
FIG. 1 shows a synthetic scheme for the synthesis of the polar deprenyl analogues A-T.

For FIG. 1 (Compounds A to T)

L-Tyrosine methyl ester hydrochloride (2)

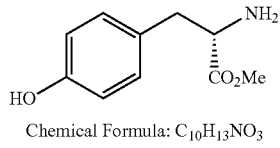

Chemical Formula: C$_{10}$H$_{13}$NO$_3$
Exact Mass: 195.09

Compound 2 was obtained as an off-white solid (19.0 g, 99% yield) from commercial L-tyrosine 1 following a procedure described by Sanda, F. et al. in *Polymer*, 2010, 51, 2255-2263.

L-N-(methoxycarbonyl)tyrosine methyl ester (3)

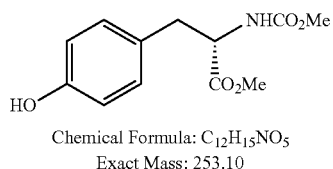

Chemical Formula: C$_{12}$H$_{15}$NO$_5$
Exact Mass: 253.10

Compound 3 was obtained from 2 as a white solid (16.4 g, quantitative yield) according to a procedure described by Boyle T. P. et al. in US patent 2006074501/2006.

L-(N-methoxycarbonyl)(O-Phenyl)tyrosine methyl ester (4A)

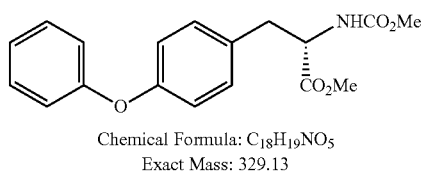

Chemical Formula: C$_{18}$H$_{19}$NO$_5$
Exact Mass: 329.13

According to Olofsson, B. et al., *Org. Lett.* 2011, 13, 1552-1555

Compound 3 (200 mg, 0.79 mmol) was added to a stirred suspension of tBuOK (97 mg, 0.87 mmol) in THF (2 mL) at 0° C. and the mixture was stirred for 30 min. Diphenyliodonium nitrate (325 mg, 0.95 mmol) was then added in one portion and the resulting deep yellow mixture was stirred at room temperature overnight. The reaction was then quenched with water at 0° C. and extracted with DCM. The combined organic layers were dried over Na$_2$SO$_4$, filtered and concentrated in vacuo. The crude residue, a yellowish wax, was flash silica gel column chromatographed (Hexane/EtOAc 95:5 to 70:30) affording 4A as a colorless wax (193 mg, 74% yield).

$^1$H NMR (400 MHz, CDCl$_3$) δ: 7.36-7.31 (m, 2H), 7.12-7.06 (m, 3H), 7.01-6.98 (m, 2H), 6.95-6.91 (m, 2H), 5.16 (br d, J=7.8 Hz, 1H), 4.63 (dt, J=7.8, 6.0 Hz, 1H), 3.73 (s, 3H), 3.67 (s, 3H), 3.13-3.03 (m, 2H).

L-(N-methoxycarbonyl)(O-Phenyl))tyrosinol (5A)

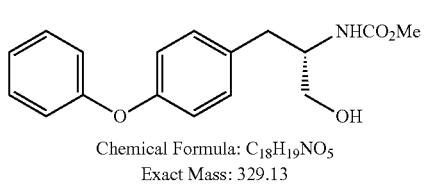

Chemical Formula: C$_{18}$H$_{19}$NO$_5$
Exact Mass: 329.13

Following the procedure described for the synthesis of 5B, methyl ester 4A (2.0 g, 6.1 mmol) was converted to a 5:3 mixture of product 5A (calculated yield: 1.1 g, 59%), obtained as a colorless wax. This mixture was engaged in the next step without further purification.

L-(N-methoxycarbonyl)(O-Phenyl))tyrosinol tosylate (6A)

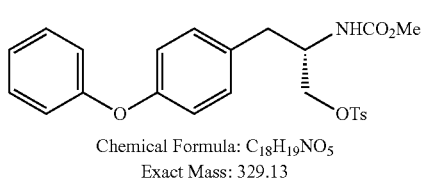

Chemical Formula: C$_{18}$H$_{19}$NO$_5$
Exact Mass: 329.13

Following the procedure described for the synthesis of 6B, alcohol 5A (500 mg, 1.66 mmol) was converted to 6A (white solid, 330 mg, 44% yield).

$^1$H NMR (400 MHz, CDCl$_3$) δ: 7.79-7.77 (m, 2H), 7.36-7.32 (m, 4H), 7.13-7.09 (m, 1H), 7.03-7.01 (m, 2H), 6.99-6.96 (m, 2H), 6.87-6.85 (m, 2H), 4.89 (br d, J=7.6 Hz, 1H), 4.06-3.99 (m, 2H), 3.94 (dd, J=9.5, 3.0 Hz, 1H), 3.62 (s, 3H), 2.87-2.75 (m, 2H), 2.43 (s, 3H).

(R)-methyl (1-(4-phenoxyphenyl)propan-2-yl)carbamate (7A)

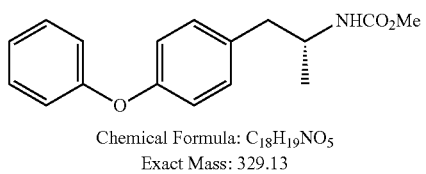

Chemical Formula: C$_{18}$H$_{19}$NO$_5$
Exact Mass: 329.13

Following the procedure described for the synthesis of 7B, tosylate 6A (2.5 g, 5.5 mmol) was converted to 7A (white solid, 1.3 g, 83% yield).

(R)-1-(4-(phenoxy)phenyl)-N-methylpropan-2-amine (8A)

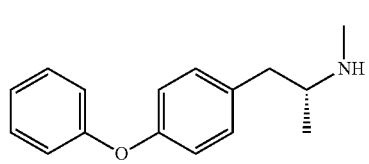

Chemical Formula: C$_{18}$H$_{19}$NO$_5$
Exact Mass: 329.13

Following the procedure described for the synthesis of 7B, tosylate 7A was converted to 8A (white solid).

N—((R)-(1-(4-(phenoxy)phenyl)propan-2-yl)(methyl))glycine tert-butyl ester (9A)

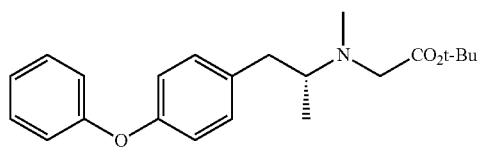

Chemical Formula: C$_{18}$H$_{19}$NO$_5$
Exact Mass: 329.13

Compound 8A (200 mg, 1.65 mmol) was dissolved in DMF (10 mL) in a 10-20 mL microwave tube. Cs$_2$CO$_3$ (538 mg, 1.65 mmol) and K$_2$CO$_3$ (456 mg, 3.31 mmol) and tert-butyl bromoacetate (244 µL, 1.65 mmol) were added sequentially, and the mixture was heated under microwave conditions at 80° C. for 90 minutes. The crude mixture was then filtered, concentrated under vacuum, taken up in H$_2$O, and extracted with DCM. The combined organic layers were dried over Na$_2$SO$_4$, filtered, and concentrated in vacuo. The residue was flash silica gel column chromatographed (DCM to DCM/MeOH 95:5), affording 9A as yellowish wax (507 mg, 80% yield).

$^1$H NMR (400 MHz, CDCl$_3$) δ: 7.36-7.31 (m, 2H), 7.17-7.14 (m, 2H), 7.12-7.08 (m, 1H), 7.03-6.99 (m, 2H), 6.96-6.93 (m, 2H), 3.24 (s, 2H), 3.02-2.95 (m, 2H), 2.44 (s, 3H), 2.39 (m/dd, J=14.1, 10.8 Hz, 1H), 1.50 (s, 9H), 0.97 (d, J=6.6 Hz, 3H).

$^{13}$C NMR (100 MHz, CDCl$_3$) δ: 170.2 (C$_{quat.}$), 157.8 (C$_{quat.}$), 155.5 (C$_{quat.}$), 135.5 (C$_{quat.}$), 130.6 (2CH), 129.9 (2CH), 123.2 (CH), 119.1 (2CH), 118.8 (2CH), 81.0 (C$_{quat.}$), 60.6 (CH), 56.2 (CH$_2$), 39.2 (CH$_2$), 38.4 (CH$_3$), 28.4 (3CH$_3$), 14.7 (CH$_3$).

N—((R)-(1-(4-(phenoxy)phenyl)propan-2-yl)(methyl))glycine hydrochloride (A) (PS-RG0008)

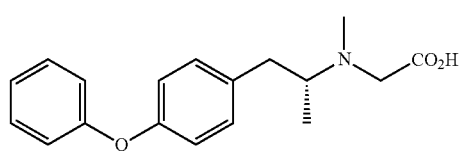

Chemical Formula: C$_{18}$H$_{19}$NO$_5$
Exact Mass: 329.13

Concentrated HCl (1.5 mL) was added dropwise to a cooled (0° C.) solution of tert-butyl ester 9A (295 mg, 0.83 mmol) in THF (1.5 mL), and stirring was continued for 3 h. The solvent was then removed in vacuo, and the crude product mixture was taken up in water and washed with DCM. Concentration of the water layer furnished product A as a light yellow solid (186 mg, 67% yield).

$^1$H NMR (400 MHz, DMSO-d6) δ: 10.05 (br s, 1H), 7.40-7.37 (m, 2H), 7.30-7.27 (m, 2H), 7.15-7.11 (m, 1H), 7.00-6.97 (m, 4H), 4.16 (br s, 2H), 3.63 (br s, 2H), 3.25 (d, J=11.9 Hz, 1H), 2.86 (s, 3H), 2.70 (t, J=11.9, 1H), 1.12 (d, J=6.2 Hz, 3H).

$^{13}$C NMR (100 MHz, MeOD) δ: 168.7 (C$_{quat.}$), 158.6 (C$_{quat.}$), 158.3 (C$_{quat.}$), 132.1 (2CH), 132.0 (C$_{quat.}$), 131.1 (2CH), 124.7 (CH), 120.2 (2CH), 120.1 (2CH), 65.2 (CH), 54.1 (CH$_2$), 37.5 (CH$_3$), 37.3 (CH$_2$), 13.2 (CH$_3$).

HRMS: m/z calculated for C$_{18}$H$_{22}$NO$_3^+$: 300.15942, found: 300.15891.

L-(N-methoxycarbonyl)(O-Benzyl)tyrosine methyl ester (4B)

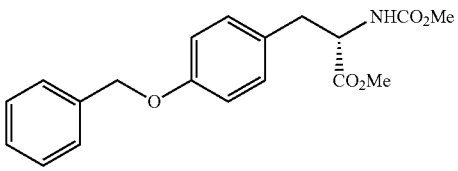

Chemical Formula: C$_{19}$H$_{21}$NO$_5$
Exact Mass: 343.14

Compound 3 (8.0 g, 32 mmol), benzyl bromide (4.5 mL, 38 mmol) and K$_2$CO$_3$ (5.2 g, 38 mmol) in acetone (125 mL) was stirred for 16 h at room temperature and then refluxed for 3 h. Solids were filtered off and the filtrate was concentrated to dryness in vacuo. The crude product mixture was column chromatographed (silica gel; Hexane/EtOAc 9:1 to 1:1), affording 4B as a translucent wax, which turned into a white solid upon standing (9.3 g, 85% yield).

$^1$H NMR (400 MHz, CDCl$_3$) δ: 7.44-7.37 (m, 4H), 7.35-7.30 (m, 1H), 7.05-7.01 (m, 2H), 6.92-6.88 (m, 2H), 5.13 (br d, J=7.8 Hz, 1H), 5.04 (s, 2H), 4.61 (dt, J=7.8, 5.8 Hz, 1H), 3.72 (s, 3H), 3.67 (s, 3H), 3.09-3.00 (m, 2H).

L-(N-methoxycarbonyl)(O-Benzyl))tyrosinol (5B)

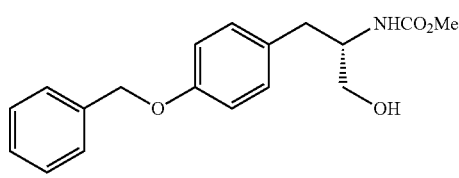

Chemical Formula: C₁₈H₂₁NO₄
Exact Mass: 315.15

NaBH₄ (2.2 g, 54 mmol) was added in portions to a solution of compound 4B (7.4 g, 22 mmol) in EtOH (100 mL) at 0° C. The resulting suspension was stirred overnight at room temperature. The reaction was quenched by addition of MeOH and with stirring at 0° C. for 30 min. The mixture was then concentrated in vacuo, and the residue was taken up in DCM and washed twice with brine and water. The organic layer was dried over Na₂SO₄, filtered, and concentrated to dryness in vacuo. The product was passed through a short column of silica pad (Hexane/EtOAc 1:2), affording a 10:3 mixture (6.3 g) of 5B (calculated yield: 4.8 g, 71%) and an unidentified side product as a colorless wax. This mixture was engaged in the next step without further purification.

L-(N-methoxycarbonyl)(O-Benzyl))tyrosinol tosylate (6B)

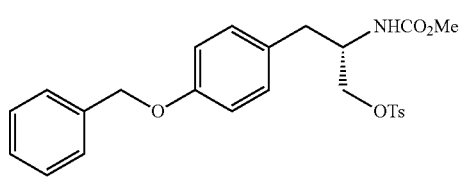

Chemical Formula: C₂₅H₂₇NO₆S
Exact Mass: 469.16

Compound 5B (500 mg, 1.59 mmol) was dissolved in DCM (6 mL) and pyridine (2 mL). Tosyl chloride (907 mg, 4.76 mmol) was added in portions and the resulting solution was stirred overnight at room temperature. The reaction was then quenched at 0° C. by addition of water, and the resultant mixture was extracted with DCM. The organic layer was dried over Na₂SO₄, filtered, and concentrated in vacuo. The crude product was flash column chromatographed (silica gel; Hexane/EtOAc 9:1 to 7:3), affording 6B as a white solid (508 mg, 68% yield).

¹H NMR (400 MHz, CDCl₃) δ: 7.79-7.76 (m, 2H), 7.44-7.31 (m, 7H), 7.00-6.98 (m, 2H), 6.85-6.83 (m, 2H), 5.03 (s, 2H), 4.82 (br d, J=7.7 Hz, 1H), 4.03-3.95 (m, 2H), 3.92 (dd, J=9.5, 2.9 Hz, 1H), 3.61 (s, 3H), 2.84-2.71 (m, 2H), 2.46 (s, 3H)

(R)-methyl (1-(4-benzyloxyphenyl)propan-2-yl) carbamate (7B)

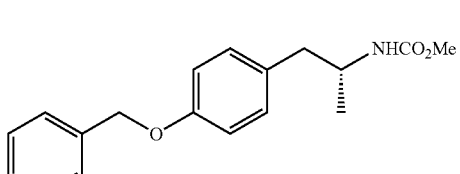

Chemical Formula: C₁₈H₂₁NO₃
Exact Mass: 299.15

According to Yamada, K. et al., *Syn. Commun.* 1998, 28, 1935-1940

A mixture of compound 6B (550 mg, 1.17 mmol), zinc dust (7.66 mg, 11.71 mmol) and NaI (878 mg, 5.86 mmol) in THF (5 mL) H₂O (0.3 mL) was refluxed for 2.5 h. The remaining zinc was then filtered off and the filtrate was concentrated in vacuo. The residue was then taken up in DCM/water, the layers were separated and the aqueous layer was extracted twice with DCM. The combined organic layers were dried over Na₂SO₄, filtered, and concentrated in vacuo, affording 7B as a colorless wax, which turned into a white solid upon standing (357 mg, quantitative yield).

¹H NMR (400 MHz, CDCl₃) δ: 7.45-7.43 (m, 2H), 7.41-7.37 (m, 2H), 7.35-7.31 (m, 1H), 7.12-7.09 (m, 2H), 6.94-6.91 (m, 2H), 5.05 (s, 2H), 4.63 (br s, 1H), 3.94 (br s, 1H), 3.65 (s, 3H), 2.80 (dd, J=13.6, 5.2 Hz, 1H), 2.66 (dd, J=13.6, 7.1 Hz, 1H), 1.13 (d, J=6.6 Hz, 3H).

¹³C NMR (100 MHz, CDCl₃) δ: 157.6 ($C_{quat.}$), 156.5 ($C_{quat.}$), 137.2 ($C_{quat.}$), 130.53 (2CH), 130.45 ($C_{quat.}$), 128.7 (2CH), 128.1 (CH), 127.6 (2CH), 114.9 (2CH), 70.1 (CH₂), 52.0 (CH₃), 48.2 (CH), 42.1 (CH₂), 20.3 (CH₃).

(R)-1-(4-(benzyloxy)phenyl)-N-methylpropan-2-amine (8B)

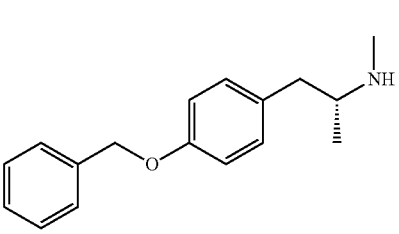

Chemical Formula: C₁₇H₂₁NO
Exact Mass: 255.16

A solution of 7B (1.15 g, 3.84 mmol) in dry THF (5 mL) was added slowly to a solution of LiAlH₄ (583 mg, 15.37 mmol) in dry THF (10 mL) at 0° C. The resultant mixture was stirred at reflux for 4 h and then quenched at 0° C. by sequential addition of H₂O (600 μL), 10% NaOH$_{aq}$ (600 μL), and H₂O (1.2 mL), and the solids were removed by vacuum filtration. The crude product was purified by silica gel flash chromatography (DCM/MeOH 98:2 to 9:1), affording 8B as a colorless oil (529 mg, 54% yield).

¹H NMR (400 MHz, CDCl₃) δ: 7.45-7.42 (m, 2H), 7.41-7.37 (m, 2H), 7.35-7.30 (m, 1H), 7.12-7.09 (m, 2H), 6.94-6.90 (m, 2H), 5.05 (s, 2H), 2.81 (m, 1H), 2.67 (dd,

J=13.4, 7.0 Hz, 1H), 2.58 (dd, J=13.4, 6.3 Hz, 1H), 2.40 (s, 3H), 1.78 (br s, 1H), 1.06 (d, J=6.1 Hz, 3H).

N—((R)-(1-(4-(benzyloxy)phenyl)propan-2-yl)(methyl)) glycine tert-butyl ester (9B)

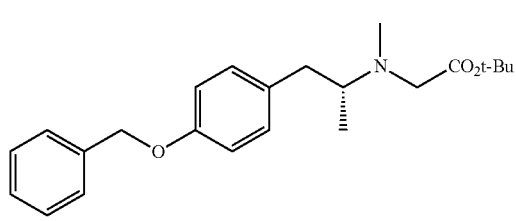

Chemical Formula: C$_{23}$H$_{31}$NO$_3$
Exact Mass: 369.23

Tert-butyl bromoacetate (304 µL, 2.06 mmol) was added dropwise to a vigorously stirred solution of compound 8B (525 mg, 2.06 mmol) in DMF (3 mL). Cs$_2$CO$_3$ (1.34 g, 4.11 mmol) was added after 5 minutes, and the resulting suspension was stirred overnight at room temperature. The crude mixture was diluted with water and extracted with DCM. The combined organic layers were dried over Na$_2$SO$_4$, filtered and concentrated in vacuo. The crude product mixture was column chromatographed (silica gel; Hexane/ EtOAc 8:2 to 5:5), affording 9B as a viscous light yellow oil (603 mg, 79% yield).

$^1$H NMR (400 MHz, CDCl$_3$) δ: 7.45-7.42 (m, 2H), 7.40-7.36 (m, 2H), 7.34-7.30 (m, 1H), 7.11-7.07 (m, 2H), 6.91-6.88 (m, 2H), 5.04 (s, 2H), 3.22 (br s, 2H), 2.97-2.88 (m, 2H), 2.41 (s, 3H), 2.36-2.29 (m, 1H), 1.48 (s, 9H), 0.93 (d, J=6.7 Hz, 3H).

N—((R)-(1-(4-(benzyloxy)phenyl)propan-2-yl) (methyl))glycine hydrochloride (B) (PS-RG0031A)

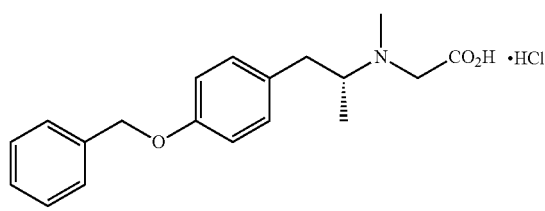

Chemical Formula: C$_{19}$H$_{23}$NO$_3$
Exact Mass: 313.17

Concentrated HCl (1.5 mL) was added dropwise to a cooled (0° C.) solution of tert-butyl ester 9B (200 mg, (0.54 mmol) in THF (1.5 mL), and stirring was continued for 3 h. The solvent was then removed in vacuo, and product B (105 mg, 55% yield) was isolated after trituration of the crude solid residue with DCM, and subsequent separation of the crude residue from small quantities (15 mg, 11%) of the product resulting from O-debenzylation by C-18 reverse phase chromatography (H$_2$O/MeOH, 95:5 to 50:50).

$^1$H NMR (400 MHz, MeOD) δ: 7.43-7.41 (m, 2H), 7.38-7.34 (m, 2H), 7.32-7.28 (m, 1H), 7.21-7.18 (m, 2H), 6.99-6.96 (m, 2H), 5.07 (s, 2H), 3.70-3.59 (m, 2+1H), 3.13 (dd, J=13.2, 4.2 Hz, 1H), 2.88 (s, 3H), 2.73 (dd, J=13.2, 10.5 Hz, 1H), 1.21 (d, J=6.7 Hz, 3H).

$^{13}$C NMR (100 MHz, MeOD) δ: 170.0 (C$_{quat.}$), 159.6 (C$_{quat.}$), 138.8 (C$_{quat.}$), 131.6 (2CH), 129.65 (2CH), 129.57 (C$_{quat.}$), 129.0 (CH), 128.7 (2CH), 116.5 (2CH), 71.1 (CH$_2$), 64.5 (CH), 56.6 (CH$_2$), 38.9 (CH$_3$), 37.7 (CH$_2$), 13.3 (CH$_3$).

HRMS: m/z calculated for C$_{19}$H$_{24}$NO$_3^+$: 314.17507, found: 314.17456.

N—((R)-(1-(4-phenol)propan-2-yl)(methyl))glycine tert-butyl ester (10)

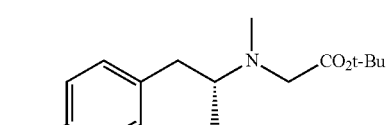

Chemical Formula: C$_{16}$H$_{25}$NO$_3$
Exact Mass: 279.18

Compound 9B was dissolved in nitrogen flushed MeOH (600 mg, 1.62 mmol), palladium on charcoal (60 mg) was added and the reaction was stirred overnight at room temperature under hydrogen at 1 atmosphere. The mixture was then filtered through Celite and then alumina to remove the catalyst and the filtrate was concentrated in vacuo, affording 10 as a light yellow oil (453 mg, 99% yield).

$^1$H NMR (400 MHz, CDCl$_3$) δ: 7.00 (d, J=8.1 Hz, 2H), 6.74 (d, J=8.1 Hz, 2H), 3.23 (s, 2H), 2.95-2.90 (m, 2H), 2.41 (s, 3H), 2.30 (dd, J=13.3, 11.2 Hz), 1.47 (s, 9+1H), 0.92 (d, J=6.1 Hz, 3H).

N—((R)-(1-(4-(2-chlorobenzyloxy)phenyl)propan-2-yl)(methyl))glycine tert-butyl ester (11C)

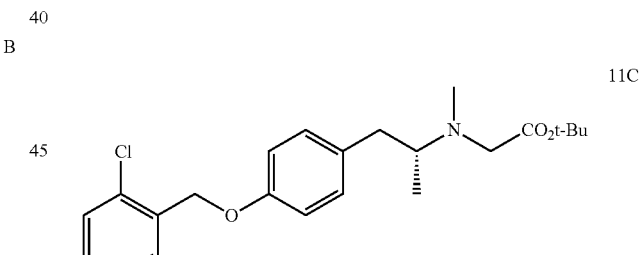

Chemical Formula: C$_{23}$H$_{30}$ClNO$_3$
Exact Mass: 403.19

Compound 10 (100 mg, 0.36 mmol), 2-chlorobenzyl bromide (0.40 mmol, 51 µL) and K$_2$CO$_3$ (148 mg, 1.07 mmol) were added to DMF (2.0 mL) and the resulting mixture was stirred overnight at room temperature. Solids in suspension were filtered off and the solvent was evaporated in vacuo. The crude product mixture was column chromatographed (silica gel; Hexane/EtOAc 8:2 to 5:5), affording 11C as a viscous light yellow oil (83 mg, 57% yield).

$^1$H NMR (400 MHz, CDCl$_3$) δ: 7.57-7.54 (m, 1H), 7.40-7.37 (m, 1H), 7.30-7.22 (m, 2H), 7.12-7.08 (m, 2H), 6.92-6.88 (m, 2H), 5.14 (s, 2H), 3.22 (br s, 2H), 2.97-2.89 (m, 2H), 2.41 (s, 3H), 2.36-2.30 (m, 1H), 1.48 (s, 9H), 0.93 (d, J=6.7 Hz, 3H).

N—((R)-1-(4-(2-chlorobenzyloxy)phenyl)propan-2-yl)(methyl))glycine hydrochloride (C) (PS-RG0121)

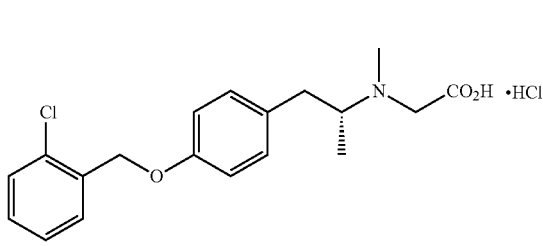

Chemical Formula: $C_{19}H_{22}ClNO_3$
Exact Mass: 347.13

Concentrated HCl (1.5 mL) was added dropwise to a cooled (0° C.) solution of tert-butyl ester 11C (83 mg, 0.21 mmol) in THF (1.5 mL), and stirring was continued for 3 h. The solvent was then removed in vacuo, and product C (69 mg, 87% yield) was isolated by C-18 reverse phase chromatography ($H_2O$/MeOH, 95:5 to 50:50).

$^1$H NMR (400 MHz, MeOD) δ: 7.56-7.52 (m, 1H), 7.44-7.40 (m, 1H), 7.33-7.28 (m, 2H), 7.23-7.20 (m, 2H), 6.98-6.96 (m, 2H), 5.13 (s, 2H), 3.70-3.61 (m, 2+1H), 3.15 (dd, J=13.1, 4.0 Hz, 1H), 2.88 (s, 3H), 2.72 (dd, J=13.1, 10.6 Hz, 1H), 1.21 (d, J=6.7 Hz, 3H).

$^{13}$C NMR (100 MHz, MeOD) δ: 170.0 ($C_{quat.}$), 159.4 ($C_{quat.}$), 136.2 ($C_{quat.}$), 134.2 ($C_{quat.}$), 131.7 (2CH), 130.6 (3CH), 129.9 ($C_{quat.}$), 128.3 (CH), 116.4 (2CH), 68.4 ($CH_2$), 64.4 (CH), 56.6 (br, $CH_2$), 38.9 (br, $CH_3$), 37.7 ($CH_2$), 13.3 ($CH_3$).

HRMS: m/z calculated for $C_{19}H_{23}ClNO_3^+$: 348.13610, found: 348.13620.

N—((R)-1-(4-(3-chlorobenzyloxy)phenyl)propan-2-yl)(methyl))glycine hydrochloride (D) (PS-RG0103)

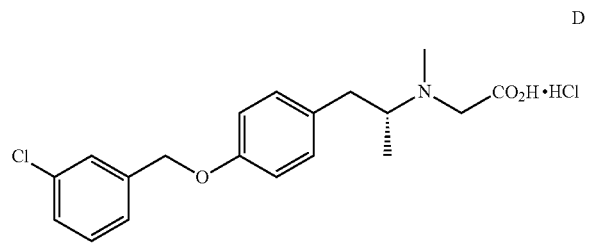

Chemical Formula: $C_{19}H_{22}ClNO_3$
Exact Mass: 347.13

Following the procedure for the preparation of 11C, and its conversion to compound C on acid treatment, compound D was obtained as a white solid (54 mg, 71% yield) after C-18 reverse phase chromatography ($H_2O$/MeOH, 95:5 to 30:70).

$^1$H NMR (400 MHz, MeOD) δ: 7.43 (br s 1H), 7.35-7.33 (m, 2H), 7.31-7.27 (m, 1H), 7.20 (d, J=8.7 Hz, 2H), 6.96 (d, J=8.7 Hz, 2H), 5.04 (s, 2H), 3.70-3.55 (m, 2+1H), 3.14 (dd, J=13.1, 4.0 Hz, 1H), 2.88 (s, 3H), 2.71 (dd, J=13.1, 10.6 Hz, 1H), 1.20 (d, J=6.6 Hz, 3H).

$^{13}$C NMR (100 MHz, MeOD) δ: 170.0 ($C_{quat.}$), 159.3 ($C_{quat.}$), 141.2 ($C_{quat.}$), 135.5 ($C_{quat.}$), 131.7 (2CH), 131.2 (CH), 129.8 ($C_{quat.}$), 129.0 (CH), 128.4 (CH), 126.8 (CH), 116.5 (2CH), 70.1 ($CH_2$), 64.4 (CH), 56.7 (br, $CH_2$), 38.9 (br, $CH_3$), 37.7 ($CH_2$), 13.2 ($CH_3$).

HRMS: m/z calculated for $C_{19}H_{23}ClNO_3^+$: 348.13610, found: 348.13617.

(R)—N-(1-(4-((4-chlorobenzyl)oxy)phenyl)propan-2-yl)-N-methylglycine hydrochloride (E) (PS-RG00226)

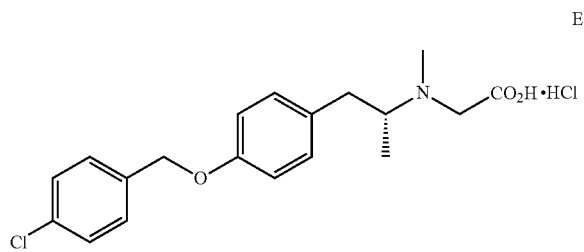

Chemical Formula: $C_{19}H_{22}ClNO_3$
Exact Mass: 347.13

Following the procedure for the preparation of 11C, and its conversion to compound C on acid treatment, compound E was obtained as a colorless solid (25 mg, 66% yield) after C-18 reverse phase chromatography ($H_2O$/MeOH, 90:10 to 30:70).

$^1$H NMR (400 MHz, MeOD) δ: 7.40 (d, J=8.4 Hz, 2H), 7.35 (d, J=8.4 Hz, 2H), 7.20 (d, J=8.4 Hz, 2H), 6.96 (d, J=8.4 Hz, 2H), 5.03 (s, 2H), 3.70-3.59 (m, 2+1H), 3.14 (dd, J=13.1, 3.8 Hz, 1H), 2.88 (s, 3H), 2.72 (dd, J=13.1, 10.6 Hz, 1H), 1.20 (d, J=6.6 Hz, 3H).

$^{13}$C NMR (100 MHz, MeOD) δ: 170.0 ($C_{quat.}$), 159.4 ($C_{quat.}$), 137.6 ($C_{quat.}$), 134.7 ($C_{quat.}$), 131.6 (2CH), 130.2 (2CH), 129.8 ($C_{quat.}$), 129.7 (2CH), 116.5 (2CH), 70.3 ($CH_2$), 64.5 (CH), 56.6 (br, $CH_2$), 38.8 (br, $CH_3$), 37.7 ($CH_2$), 13.2 ($CH_3$).

HRMS: m/z calculated for $C_{19}H_{23}ClNO_3^+$: 348.13610, found: 348.13519.

(R)—N-(1-(4-((2-cyanobenzyl)oxy)phenyl)propan-2-yl)-N-methylglycine hydrochloride (F) (PS-RG0171)

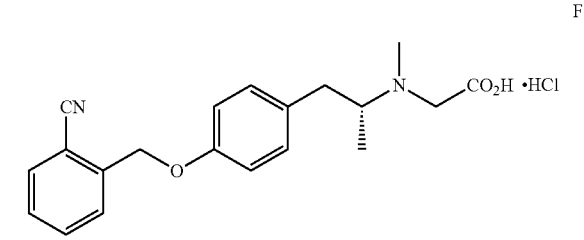

Chemical Formula: $C_{20}H_{22}N_2O_3$
Exact Mass: 338.16

Following the procedure for the preparation of 11C, and its conversion to compound C on acid treatment, compound F was obtained as a colorless solid (88 mg, 77% yield) after C-18 reverse phase chromatography ($H_2O$/MeOH, 90:10 to 30:70).

$^1$H NMR (400 MHz, MeOD) δ: 7.77 (br d, J=7.6, 1H), 7.70-7.66 (m, 2H), 7.54-7.47 (m, 1H), 7.25-7.21 (m, 2H), 7.02-6.99 (m, 2H), 5.21 (s, 2H), 3.71-3.60 (m, 2+1H), 3.16 (dd, J=13.2, 4.0 Hz, 1H), 2.89 (s, 3H), 2.73 (dd, J=13.2, 10.5 Hz, 1H), 1.21 (d, J=6.7 Hz, 3H).

$^{13}$C NMR (100 MHz, MeOD) δ: 170.0 ($C_{quat.}$), 159.2 ($C_{quat.}$), 141.9 ($C_{quat.}$), 134.5 (CH), 134.4 (CH), 131.8 (2CH), 130.5 (CH), 130.3 ($C_{quat.}$), 130.1 (CH), 118.3 ($C_{quat.}$), 116.5 (2CH), 113.0 ($C_{quat.}$), 69.2 ($CH_2$), 64.4 (CH), 56.6 (br, $CH_2$), 38.9 (br, $CH_3$), 37.7 ($CH_2$), 13.2 ($CH_3$).

HRMS: m/z calculated for $C_{20}H_{23}N_2O_3^+$: 339.17032, found: 339.17056.

(R)—N-(1-(4-((3-cyanobenzyl)oxy)phenyl)propan-2-yl)-N-methylglycine hydrochloride (G) (PS-RG0172)

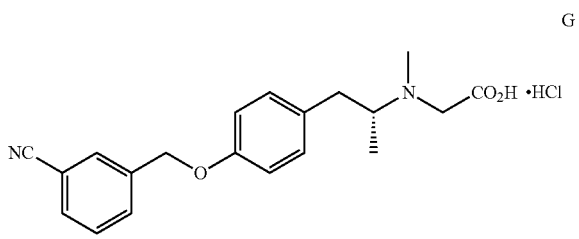

Chemical Formula: $C_{20}H_{22}N_2O_3$
Exact Mass: 338.16

Following the procedure for the preparation of 11C, and its conversion to compound C on acid treatment, compound G was obtained as colorless solid (90 mg, 75% yield) after C-18 reverse phase chromatography ($H_2O$/MeOH, 90:10 to 30:70).

$^1$H NMR (400 MHz, MeOD) δ: 7.78 (br s 1H), 7.74 (br d, J=7.7 Hz, 1H), 7.66 (dt, J=7.7, 1.3 Hz, 1H), 7.55 (t, J=7.7 Hz, 1H), 7.24-7.20 (m, 2H), 7.00-6.96 (m, 2H), 5.11 (s, 2H), 3.70-3.58 (m, 2+1H), 3.15 (dd, J=13.2, 4.2 Hz, 1H), 2.89 (s, 3H), 2.73 (dd, J=13.2, 10.6 Hz, 1H), 1.21 (d, J=6.7 Hz, 3H).

$^{13}$C NMR (100 MHz, MeOD) δ: 170.0 ($C_{quat.}$), 159.2 ($C_{quat.}$), 140.7 ($C_{quat.}$), 133.1 (CH), 132.7 (CH), 132.0 (CH), 131.7 (2CH), 130.8 (CH), 130.1 ($C_{quat.}$), 119.8 ($C_{quat.}$), 116.5 (2CH), 113.7 ($C_{quat.}$), 69.8 ($CH_2$), 64.4 (CH), 56.7 (br, $CH_2$), 38.9 (br, $CH_3$), 37.7 ($CH_2$), 13.2 ($CH_3$).

HRMS: m/z calculated for $C_{20}H_{23}N_2O_3^+$: 339.17032, found: 339.17050.

(R)—N-(1-(4-((4-cyanobenzyl)oxy)phenyl)propan-2-yl)-N-methylglycine hydrochloride (H) (PS-AD0065)

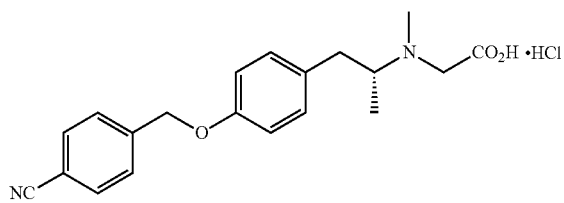

Chemical Formula: $C_{20}H_{22}N_2O_3$
Exact Mass: 338.16

Following the procedure for the preparation of 11C, and its conversion to compound C on acid treatment, compound H was obtained as an off-white solid (51 mg, 49% yield) after C-18 reverse phase chromatography ($H_2O$/MeOH, 90:10 to 30:70).

$^1$H NMR (400 MHz, MeOD) δ: 7.72 (d, J=8.2 Hz, 2H), 7.60 (d, J=8.2 Hz, 2H), 7.22 (d, J=8.6 Hz, 2H), 6.97 (d, J=8.6 Hz, 2H), 5.15 (s, 2H), 3.70-3.59 (m, 2+1H), 3.15 (dd, J=13.1, 4.2 Hz, 1H), 2.89 (s, 3H), 2.73 (dd, J=13.1, 10.6 Hz, 1H), 1.21 (d, J=6.6 Hz, 3H).

$^{13}$C NMR (100 MHz, MeOD) δ: 170.0 ($C_{quat.}$), 159.2 ($C_{quat.}$), 144.7 ($C_{quat.}$), 133.6 (201), 131.7 (2CH), 130.1 ($C_{quat.}$), 129.1 (2CH), 119.8 ($C_{quat.}$), 116.5 (2CH), 112.6 ($C_{quat.}$), 70.0 ($CH_2$), 64.4 (CH), 56.7 (br, $CH_2$), 38.9 (br, $CH_3$), 37.7 ($CH_2$), 13.3 ($CH_3$).

HRMS: m/z calculated for $C_{20}H_{23}N_2O_3^+$: 339.17032, found: 339.17065.

(R)—N-(1-(4-((3-fluorobenzyl)oxy)phenyl)propan-2-yl)-N-methylglycine hydrochloride (I) (PS-RG0173)

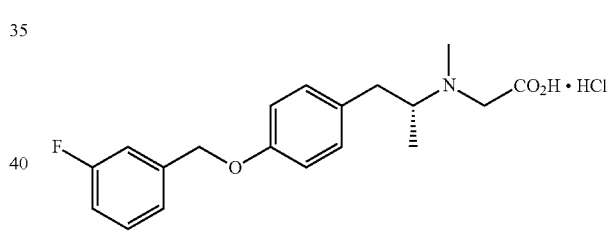

Chemical Formula: $C_{19}H_{22}FNO_3$
Exact Mass: 331.16

Following the procedure for the preparation of 11C, and its conversion to compound C on acid treatment, compound I was obtained as a colorless solid (86 mg, 77% yield) after C-18 reverse phase chromatography ($H_2O$/MeOH, 90:10 to 30:70).

$^1$H NMR (400 MHz, MeOD) δ: 7.35 (td, J=8.0, 6.0 Hz, 1H), 7.22-7.18 (m, 3H), 7.16-7.13 (m, 1H), 7.01 (td, J=8.5, 2.5 Hz, 1H), 6.97-6.93 (m, 2H), 5.03 (s, 2H), 3.70-3.59 (m, 2+1H), 3.15 (dd, J=13.2, 3.9 Hz, 1H), 2.88 (s, 3H), 2.70 (dd, J=13.2, 10.6 Hz, 1H), 1.19 (d, J=6.6 Hz, 3H).

$^{13}$C NMR (100 MHz, MeOD) δ: 170.0 ($C_{quat.}$), 164.4 (d, J=244.2 Hz, $C_{quat.}$), 159.3 ($C_{quat.}$), 141.7 (d, J=7.3 Hz, $C_{quat.}$), 131.7 (2CH), 131.4 (d, J=8.1 Hz, CH), 129.9 ($C_{quat.}$), 124.2 (d, J=2.8 Hz, CH), 116.4 (2CH), 115.6 (d, J=21.3 Hz, CH), 115.1 (d, J=22.3 Hz, CH), 70.1 (d, J=2.1 Hz, $CH_2$), 64.3 (CH), 56.6 (br, $CH_2$), 38.8 (br, $CH_3$), 37.7 ($CH_2$), 13.2 ($CH_3$).

HRMS: m/z calculated for $C_{19}H_{23}FNO_3^+$: 332.16565, found: 332.16595.

(R)—N-(1-(4-((3,5-difluorobenzyl)oxy)phenyl)propan-2-yl)-N-methylglycine hydrochloride (J) (PS-RG0174)

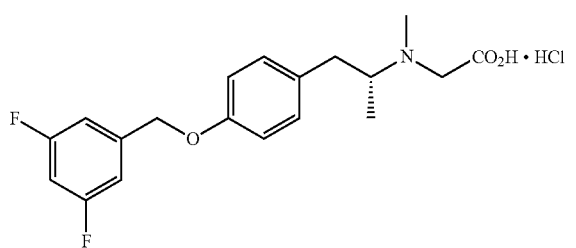

Chemical Formula: $C_{19}H_{21}F_2NO_3$
Exact Mass: 349.15

Following the procedure for the preparation of 11C, and its conversion to compound C on acid treatment, compound J was obtained as a colorless solid (108 mg, 79% yield) after C-18 reverse phase chromatography ($H_2O$/MeOH, 90:10 to 30:70).

$^1$H NMR (400 MHz, MeOD) δ: 7.24-7.20 (m, 2H), 7.07-7.01 (m, 2H), 6.99-6.96 (m, 2H), 6.87 (tt, J=9.2, 2.3 Hz, 1H), 5.09 (s, 2H), 3.70-3.59 (m, 2+1H), 3.15 (dd, J=13.2, 4.2 Hz, 1H), 2.88 (s, 3H), 2.73 (dd, J=13.2, 10.5 Hz, 1H), 1.21 (d, J=6.7 Hz, 3H).

$^{13}$C NMR (100 MHz, MeOD) δ: 170.0 ($C_{quat.}$), 164.7 (dd, J=247.2, 12.4 Hz, $C_{quat.}$), 159.1 ($C_{quat.}$), 143.6 (t, J=9.1 Hz, $C_{quat.}$), 131.7 (2CH), 130.1 ($C_{quat.}$), 116.8 (2CH), 111.0 (dd, J=19.1, 6.9 Hz, CH), 103.9 (t, J=25.9 Hz, CH), 69.6 (t, J=2.2 Hz, $CH_2$), 64.4 (CH), 56.6 (br, $CH_2$), 38.8 (br, $CH_3$), 37.7 ($CH_2$), 13.2 ($CH_3$).

HRMS: m/z calculated for $C_{19}H_{22}F_2NO_3^+$: 350.15623, found: 350.15649.

(R)—N-(1-(4-((4-bromo-3-chlorobenzyl)oxy)phenyl)propan-2-yl)-N-methylglycine hydrochloride (K) (PS-RG00216)

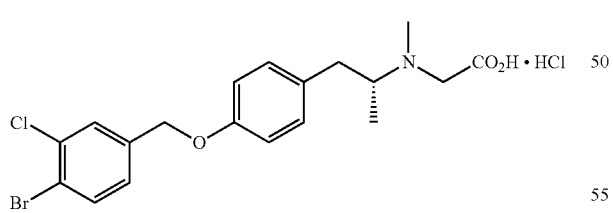

Chemical Formula: $C_{19}H_{21}BrClNO_3$
Exact Mass: 425.04

Following the procedure for the preparation of 11C, and its conversion to compound C on acid treatment, compound K was obtained as a colorless solid (87 mg, 76% yield) after C-18 reverse phase chromatography ($H_2O$/MeOH, 90:10 to 30:70).

$^1$H NMR (400 MHz, MeOD) δ: 7.65 (d, J=8.3 Hz, 1H), 7.58 (d, J=1.7 Hz, 1H), 7.26 (dd, J=8.3, 1.7 Hz, 1H), 7.21 (d, J=8.6 Hz, 2H), 6.96 (d, J=8.6 Hz, 2H), 5.02 (s, 2H), 3.69-3.58 (m, 2+1H), 3.14 (dd, J=13.2, 4.1 Hz, 1H), 2.88 (s, 3H), 2.72 (dd, J=13.2, 10.6 Hz, 1H), 1.20 (d, J=6.7 Hz, 3H).

$^{13}$C NMR (100 MHz, MeOD) δ: 170.0 ($C_{quat.}$), 159.2 ($C_{quat.}$), 140.5 ($C_{quat.}$), 135.5 ($C_{quat.}$), 135.1 (CH), 131.7 (2CH), 130.3 (CH), 130.0 ($C_{quat.}$), 128.4 (CH), 122.3 ($C_{quat.}$), 116.5 (2CH), 69.5 ($CH_2$), 64.4 (CH), 56.6 (br, $CH_2$), 38.8 (br, $CH_3$), 37.7 ($CH_2$), 13.3 ($CH_3$).

HRMS: m/z calculated for $C_{19}H_{22}BrClNO_3^+$: 426.03001, found: 426.03046 (main isotope).

(R)—N-(1-(4-((3,4-dichlorobenzyl)oxy)phenyl)propan-2-yl)-N-methylglycine hydrochloride (L) (PS-RG0245)

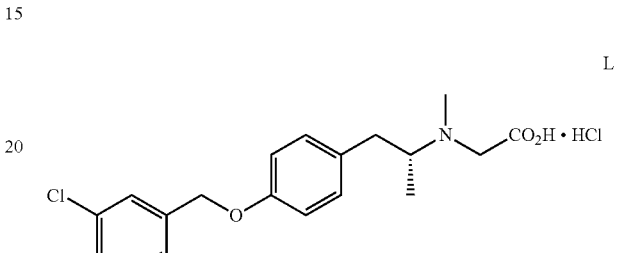

Chemical Formula: $C_{19}H_{21}Cl_2NO_3$
Exact Mass: 381.09

Following the procedure for the preparation of 11C, and its conversion to compound C on acid treatment, compound L was obtained as a colorless solid (43 mg, 68% yield) after C-18 reverse phase chromatography ($H_2O$/MeOH, 90:10 to 30:70).

$^1$H NMR (400 MHz, MeOD) δ: 7.58 (d, J=1.1 Hz, 1H), 7.50 (d, J=8.2 Hz, 1H), 7.34 (dd, J=8.2, 1.1 Hz, 1H), 7.21 (d, J=8.4 Hz, 2H), 6.96 (d, J=8.4 Hz, 2H), 5.04 (s, 2H), 3.70-3.59 (m, 2+1H), 3.14 (dd, J=13.2, 4.1 Hz, 1H), 2.88 (s, 3H), 2.72 (dd, J=13.2, 10.5 Hz, 1H), 1.21 (d, J=6.6 Hz, 3H).

$^{13}$C NMR (100 MHz, MeOD) δ: 170.0 ($C_{quat.}$), 159.2 ($C_{quat.}$), 139.8 ($C_{quat.}$), 133.5 ($C_{quat.}$), 132.7 ($C_{quat.}$), 131.8 (CH), 131.7 (2CH), 130.4 (CH), 130.0 ($C_{quat.}$), 128.3 (CH), 116.5 (2CH), 69.5 ($CH_2$), 64.4 (CH), 56.7 (br, $CH_2$), 38.9 (br, $CH_3$), 37.7 ($CH_2$), 13.3 ($CH_3$).

HRMS: m/z calculated for $C_{19}H_{20}Cl_2NO_3^-$: 380.08257, found: 380.08289 (main isotope).

(R)—N-(1-(4-((2,5-dichlorobenzyl)oxy)phenyl)propan-2-yl)-N-methylglycine hydrochloride (M) (PS-AD0064)

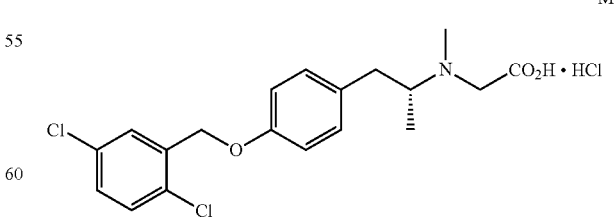

Chemical Formula: $C_{19}H_{21}Cl_2NO_3$
Exact Mass: 381.09

Following the procedure for the preparation of 11C, and its conversion to compound C on acid treatment, compound M was obtained as an off-white solid (61 mg, 77% yield) after C-18 reverse phase chromatography (H$_2$O/MeOH, 90:10 to 50:50).

$^1$H NMR (400 MHz, MeOD) δ: 7.53 (d, J=1.7 Hz, 1H), 7.39 (d, J=8.4 Hz, 1H), 7.30 (dd, J=8.4, 1.7 Hz, 1H), 7.23 (d, J=7.7 Hz, 2H), 6.97 (d, J=7.7 Hz, 2H), 5.08 (s, 2H), 3.71-3.58 (m, 2+1H), 3.16 (br d, J=12.1 Hz, 1H), 2.88 (s, 3H), 2.73 (br t, J=11.6 Hz, 1H), 1.21 (d, J=5.9 Hz, 3H).

$^{13}$C NMR (100 MHz, MeOD) δ: 170.1 (C$_{quat.}$), 159.0 (C$_{quat.}$), 138.2 (C$_{quat.}$), 134.2 (C$_{quat.}$), 132.2 (C$_{quat.}$), 131.9 (CH), 131.8 (2CH), 130.33 (CH), 130.27 (C$_{quat.}$), 129.9 (CH), 116.4 (2CH), 67.8 (CH$_2$), 64.4 (CH), 56.6 (br, CH$_2$), 38.9 (br, CH$_3$), 37.7 (CH$_2$), 13.3 (CH$_3$).

N—((R)-(1-(4-(3-nitrobenzyloxy)phenyl)propan-2-yl)(methyl))glycine hydrochloride (N) (PS-RG0128)

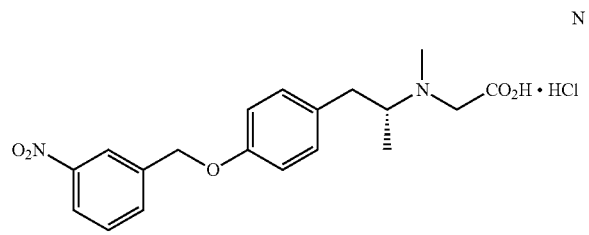

Chemical Formula: C$_{19}$H$_{22}$N$_2$O$_5$
Exact Mass: 358.15

Following the procedure for the preparation of 11C, and its conversion to compound C on acid treatment, compound N was obtained as a pale yellow solid (34 mg, 65% yield) after C-18 reverse phase chromatography (H$_2$O/MeOH, 90:10 to 30:70).

$^1$H NMR (400 MHz, MeOD) δ: 8.30 (br s, 1H), 8.16 (dd, J=8.0, 1.8 Hz, 1H), 7.83 (d, J=7.6 Hz, 1H), 7.61 (t, J=8.0 Hz, 1H), 7.22 (d, J=8.4 Hz, 2H), 7.00 (d, J=8.4 Hz, 2H), 5.18 (s, 2H), 3.66 (br s, 2+1H), 3.15 (dd, J=13.0, 3.7 Hz, 1H), 2.89 (s, 3H), 2.73 (dd, J=13.0, 10.6 Hz, 1H), 1.21 (d, J=6.6 Hz, 3H).

$^{13}$C NMR (100 MHz, MeOD) δ: 170.0 (C$_{quat.}$), 159.1 (C$_{quat.}$), 149.9 (C$_{quat.}$), 141.3 (C$_{quat.}$), 134.6 (CH), 131.7 (2CH), 131.0 (CH), 130.1 (C$_{quat.}$), 123.8 (CH), 123.1 (CH), 116.5 (2CH), 69.7 (CH$_2$), 64.4 (CH), 56.6 (br, CH$_2$), 38.9 (br, CH$_3$), 37.7 (CH$_2$), 13.2 (CH$_3$).

HRMS: m/z calculated for C$_{19}$H$_{21}$N$_2$O$_5$$^-$: 357.14560, found: 357.14594.

(R)—N-(1-(4-((3-methoxybenzyl)oxy)phenyl)propan-2-yl)-N-methylglycine hydrochloride (O) (PS-RG0264)

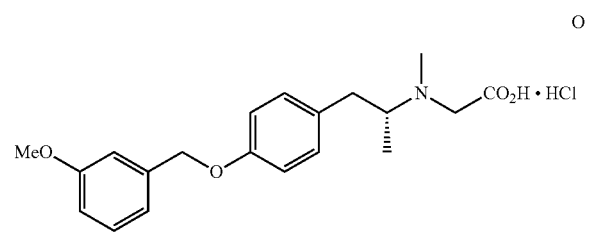

Chemical Formula: C$_{20}$H$_{25}$NO$_4$
Exact Mass: 343.18

Following the procedure for the preparation of 11C, and its conversion to compound C on acid treatment, compound O was obtained as a colorless solid (57 mg, 68% yield) after C-18 reverse phase chromatography (H$_2$O/MeOH, 60:40 to 30:70).

$^1$H NMR (400 MHz, CDCl$_3$) δ: 7.27 (t, J=7.8 Hz, 1H), 7.13 (d, J=8.2 Hz, 2H), 6.98-6.95 (m, 2H), 6.88 (d, J=8.2 Hz, 2H), 6.84 (dd, J=8.4, 2.2 Hz, 1H), 4.98 (s, 2H), 3.80 (s, 3H), 3.71 (br s, 1H), 3.57 (d, J=15.8 Hz, 1H), 3.50 (d, J=15.8 Hz, 1H), 3.24 (dd, J=13.1, 3.8 Hz, 1H), 2.83 (s, 3H), 2.52 (dd, J=13.1, 10.6 Hz, 1H), 1.17 (d, J=6.5 Hz, 3H).

$^{13}$C NMR (100 MHz, CDCl$_3$) δ: 168.0 (C$_{quat.}$), 160.0 (C$_{quat.}$), 158.1 (C$_{quat.}$), 138.6 (C$_{quat.}$), 130.5 (2CH), 129.8 (2CH), 128.4 (C$_{quat.}$), 119.8 (CH), 115.4 (CH), 113.7 (2CH), 113.0 (CH), 70.1 (CH$_2$), 62.5 (CH), 55.8 (br, CH$_2$), 55.4 (CH$_3$), 38.3 (br, CH$_3$), 37.5 (CH$_2$), 13.2 (CH$_3$).

HRMS: m/z calculated for C$_{20}$H$_{26}$NO$_4$$^+$: 344.18563, found: 344.18469.

(R)—N-(1-(4-((4-(methoxycarbonyl)benzyl)oxy)phenyl)propan-2-yl)-N-methylglycine hydrochloride (P) (PS-RG0246)

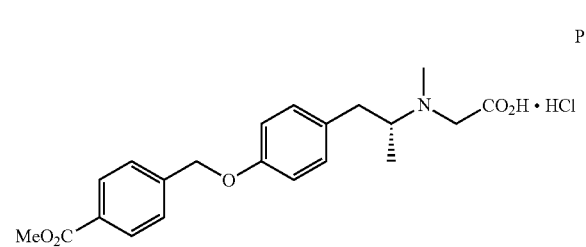

Chemical Formula: C$_{21}$H$_{25}$NO$_5$
Exact Mass: 371.17

Following the procedure for the preparation of 11C, and its conversion to compound C on acid treatment, compound P was obtained as a white solid (37 mg, 48% yield) after C-18 reverse phase chromatography (H$_2$O/MeOH, 90:10 to 30:70).

$^1$H NMR (400 MHz, MeOD) δ: 8.00 (d, J=8.1 Hz, 2H), 7.53 (d, J=8.1 Hz, 2H), 7.20 (d, J=8.4 Hz, 2H), 6.97 (d, J=8.4 Hz, 2H), 5.13 (s, 2H), 3.89 (s, 3H), 3.71-3.59 (m, 2+1H), 3.14 (dd, J=13.1, 4.0 Hz, 1H), 2.88 (s, 3H), 2.72 (dd, J=13.1, 10.6 Hz, 1H), 1.21 (d, J=6.7 Hz, 3H).

$^{13}$C NMR (100 MHz, MeOD) δ: 170.0 (C$_{quat.}$), 168.4 (C$_{quat.}$), 159.4 (C$_{quat.}$), 144.4 (C$_{quat.}$), 134.5 (C$_{quat.}$), 131.7 (2CH), 130.9 (C$_{quat.}$), 130.8 (2CH), 129.9 (C$_{quat.}$), 128.4 (2CH), 116.5 (2CH), 70.4 (CH$_2$), 64.5 (CH), 56.7 (br, CH$_2$), 52.8 (CH$_3$), 38.8 (br, CH$_3$), 37.7 (CH$_2$), 13.3 (CH$_3$).

HRMS: m/z calculated for C$_{21}$H$_{24}$NO$_5$$^-$: 370.16600, found: 370.1739.

(R)-4-((4-(2-((carboxymethyl)(methyl)amino)propyl)phenoxy)methyl)benzoic acid hydrochloride (Q) (PS-RG0065B)

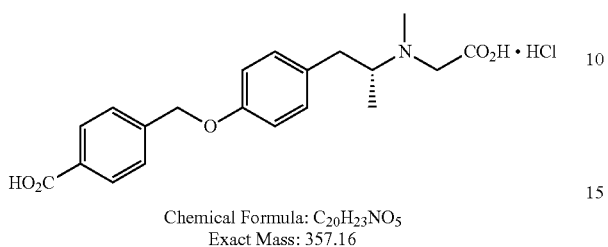

Chemical Formula: $C_{20}H_{23}NO_5$
Exact Mass: 357.16

Following the procedure for the preparation of 11C, and its conversion to compound C on acid treatment, compound Q was obtained as an off-white solid (13 mg, 12% yield after C-18 reverse phase chromatography ($H_2O$/MeOH, 90:10 to 50:50).

$^1$H NMR (400 MHz, MeOD) δ: 7.88 (d, J=8.2 Hz, 2H), 7.53 (d, J=8.2 Hz, 2H), 7.21 (d, J=8.3 Hz, 2H), 6.98 (d, J=8.3 Hz, 2H), 5.15 (s, 2H), 3.64 (br s, 2+1H), 3.13 (dd, J=13.0, 3.7 Hz, 1H), 2.88 (s, 3H), 2.73 (dd, J=13.0, 10.6 Hz, 1H), 1.21 (d, J=6.6 Hz, 3H).

$^{13}$C NMR (100 MHz, MeOD) δ: 172.2 ($C_{quat.}$), 170.0 ($C_{quat.}$), 159.5 ($C_{quat.}$), 143.0 ($C_{quat.}$), 134.5 ($C_{quat.}$), 131.7 (2CH), 129.8 ($C_{quat.}$), 129.0 (2CH), 128.4 (2CH), 116.6 (2CH), 70.5 ($CH_2$), 64.4 (CH), 56.7 (br, $CH_2$), 38.9 (br, $CH_3$), 37.7 ($CH_2$), 13.3 ($CH_3$).

(R)—N-methyl-N-(1-(4-(naphthalen-2-ylmethoxy)phenyl)propan-2-yl)glycine hydrochloride (R) (PS-RG0227)

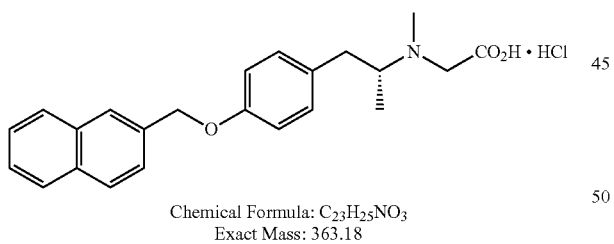

Chemical Formula: $C_{23}H_{25}NO_3$
Exact Mass: 363.18

Following the procedure for the preparation of 11C, and its conversion to compound C on acid treatment, compound R was obtained as a beige solid (30 mg, 62% yield) after C-18 reverse phase chromatography ($H_2O$/MeOH, 90:10 to 30:70).

$^1$H NMR (400 MHz, MeOD) δ: 7.87-7.81 (m, 4H), 7.52 (br d, J=8.3 Hz, 1H), 7.47-7.45 (m, 2H), 7.18 (d, J=8.2 Hz, 2H), 7.00 (d, J=8.2 Hz, 2H), 5.19 (s, 2H), 3.62 (br s, 2+1H), 3.11 (dd, J=13.1, 3.3 Hz, 1H), 2.85 (s, 3H), 2.69 (dd, J=13.1, 10.6 Hz, 1H), 1.17 (d, J=6.5 Hz, 3H).

$^{13}$C NMR (100 MHz, MeOD) δ: 170.0 ($C_{quat.}$), 159.6 ($C_{quat.}$), 136.3 ($C_{quat.}$), 134.9 ($C_{quat.}$), 134.6 ($C_{quat.}$), 131.6 (2CH), 129.6 ($C_{quat.}$), 129.4 (CH), 129.1 (CH), 128.9 (CH), 127.5 (CH), 127.4 (CH), 127.2 (CH), 126.6 (CH), 116.6 (2CH), 71.2 ($CH_2$), 64.5 (CH), 56.7 (br, $CH_2$), 38.8 (br, $CH_3$), 37.7 ($CH_2$), 13.3 ($CH_3$).

HRMS: m/z calculated for $C_{23}H_{26}NO_3^+$: 364.19072, found: 364.18982.

(R)—N-methyl-N-(1-(4-(pyridin-2-ylmethoxy)phenyl)propan-2-yl)glycine hydrochloride (S) (PS-RG0217)

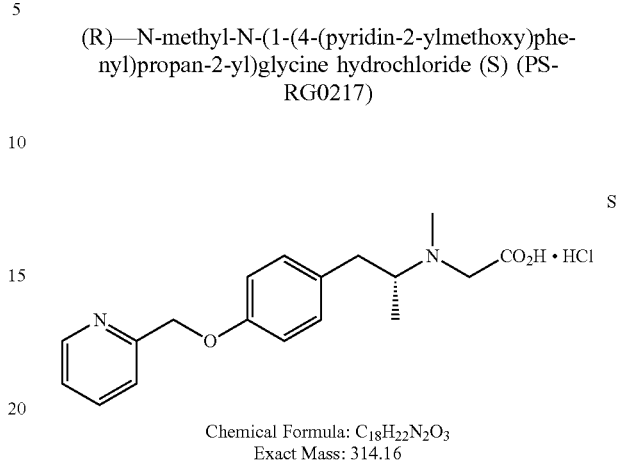

Chemical Formula: $C_{18}H_{22}N_2O_3$
Exact Mass: 314.16

Following the procedure for the preparation of 11C, and its conversion to compound C on acid treatment, compound S was obtained as a light brown solid (55 mg, 68% yield) after C-18 reverse phase chromatography ($H_2O$/MeOH, 90:10 to 30:70).

$^1$H NMR (400 MHz, MeOD) δ: 8.54 (d, J=4.9 Hz, 1H), 7.86 (td, J=7.8, 1.4 Hz, 1H), 7.59 (d, J=7.8 Hz, 1H), 7.37 (dd, J=7.8, 4.9 Hz, 1H), 7.22 (d, J=8.4 Hz, 1H), 7.00 (d, J=8.4 Hz, 1H), 5.16 (s, 2H), 3.69-3.60 (m, 2+1H), 3.15 (dd, J=13.1, 3.9 Hz, 1H), 2.89 (s, 3H), 2.73 (dd, J=13.1, 10.6 Hz, 1H), 1.21 (d, J=6.6 Hz, 3H).

$^{13}$C NMR (100 MHz, MeOD) δ: 170.0 ($C_{quat.}$), 159.3 ($C_{quat.}$), 158.4 ($C_{quat.}$), 150.0 (CH), 139.1 (CH), 131.7 (2CH), 130.0 ($C_{quat.}$), 124.6 (CH), 123.5 (CH), 116.5 (2CH), 71.4 ($CH_2$), 64.5 (CH), 56.7 (br, $CH_2$), 38.9 (br, $CH_3$), 37.6 ($CH_2$), 13.3 ($CH_3$).

HRMS: m/z calculated for $C_{18}H_{21}N_2O_3^-$: 313.15577, found: 313.15601.

(R)—N-methyl-N-(1-(4-(pyridin-4-ylmethoxy)phenyl)propan-2-yl)glycine hydrochloride (T) (PS-AD0068)

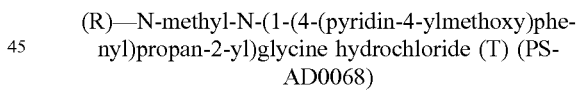

Chemical Formula: $C_{18}H_{22}N_2O_3$
Exact Mass: 314.16

Following the procedure for the preparation of 11C, and its conversion to compound C on acid treatment, compound T was obtained as an off-white wax (16 mg, 35% yield) after C-18 reverse phase chromatography ($H_2O$/MeOH, 90:10 to 30:70).

¹H NMR (400 MHz, MeOD) δ: 8.52 (d, J=4.9 Hz, 2H), 7.51 (d, J=4.9 Hz, 2H), 7.23 (d, J=8.2 Hz, 2H), 7.00 (d, J=8.2 Hz, 2H), 5.18 (s, 2H), 3.69-3.57 (m, 2+1H), 3.14 (dd, J=13.0, 3.5 Hz, 1H), 2.88 (s, 3H), 2.74 (dd, J=13.0, 10.7 Hz, 11-1), 1.21 (d, J=6.5 Hz, 3H).

¹³C NMR (100 MHz, MeOD) δ: 170.0 ($C_{quat.}$), 159.1 ($C_{quat.}$), 150.3 (2CH), 149.7 ($C_{quat.}$), 131.8 (2CH), 130.2 ($C_{quat.}$), 123.4 (2CH), 116.5 (2CH), 69.1 ($CH_2$), 64.4 (CH), 56.7 (br, $CH_2$), 38.9 (br, $CH_3$), 37.7 ($CH_2$), 13.3 ($CH_3$).

Figure 2:
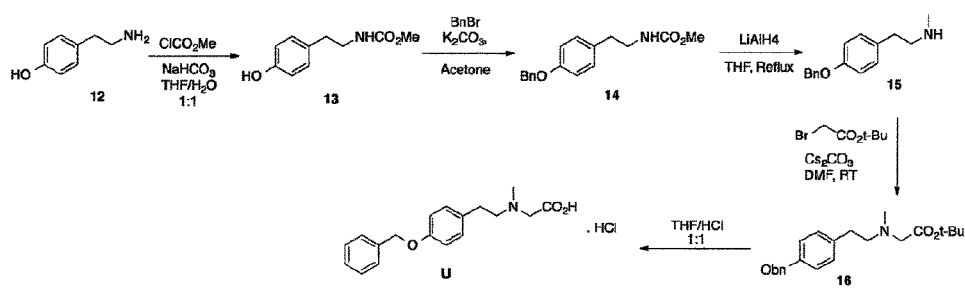
FIG. 2 shows a synthetic scheme for the preparation of polar deprenyl analogue U.

For FIG. 2 (compound U)

Methyl-(4-hydroxyphenethyl)carbamate (13)

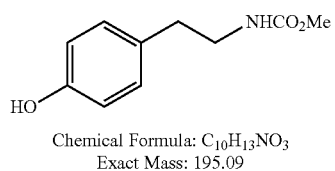

Chemical Formula: $C_{10}H_{13}NO_3$
Exact Mass: 195.09

Tyramine (1.5 g, 10.9 mmol) and sodium bicarbonate (2.8 g, 33.9 mmol) were dissolved in a 1:1 mixture of THF and water (20 mL each) and cooled to 0° C. before methyl chloroformate (0.9 mL, 12.0 mmol) was added dropwise. The mixture was stirred at 0° C. for 3 hours, then diluted with water and extracted with EtOAc and DCM. The organic layers were washed with water, combined, dried over $Na_2SO_4$, filtered, and concentrated in vacuo. Compound 13 was obtained as a slightly yellow wax (2.2 g, quantitative yield), which turned into a near colorless solid.

¹H NMR (400 MHz, CDCl₃) δ: 7.03-7.01 (m, 2H), 6.80-6.75 (m, 2H), 4.76 (br s, 1H), 3.66 (s, 3H), 3.42-3.37 (m, 2H), 2.72 (t, J=6.8 Hz, 2H).

Methyl-(4-(benzyloxy)phenethyl)carbamate (14)

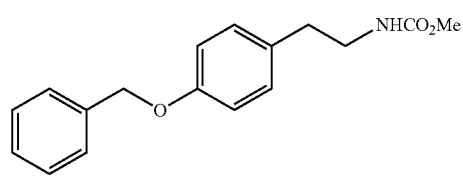

Chemical Formula: $C_{17}H_{19}NO_3$
Exact Mass: 285.14

Following the O-alkylation procedure described for the synthesis of 4B, compound 13 (1.0 g, 5.13 mmol) was converted to 14 (white solid; 1.5 g, quantitative yield).

¹H NMR (400 MHz, CDCl₃) δ: 7.45-7.36 (m, 4H), 7.34-7.30 (m, 1H), 7.11-7.09 (m, 2H), 6.94-6.90 (m, 2H), 5.05 (s, 2H), 4.66 (br s, 1H), 3.66 (s, 3H), 3.43-3.28 (m, 2H), 2.77 (t, J=6.8 Hz, 2H).

(4-(Benzyloxy)phenethyl)methylamine (15)

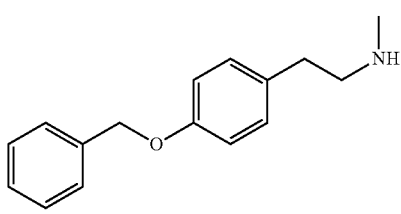

Chemical Formula: $C_{16}H_{19}NO$
Exact Mass: 241.15

Following the LiAlH₄ reduction procedure described for the synthesis of 8, carbamate 14 (500 mg, 1.75 mmol) was converted to 15 (colorless wax; 251 mg, 59% yield).

¹H NMR (400 MHz, CDCl₃) δ: 7.45-7.36 (m, 4H), 7.35-7.30 (m, 1H), 7.15-7.11 (m, 2H), 6.93-6.90 (m, 2H), 5.04 (s, 2H), 2.85-2.75 (m, 4H), 2.45 (s, 3H).

N,N-(4-(Benzyloxy)phenethyl)(methyl)glycine tert-butyl ester (16)

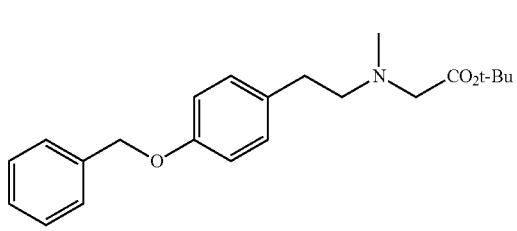

Chemical Formula: $C_{22}H_{29}NO_3$
Exact Mass: 355.21

Tert-Butylbromoacetate (80 μL, 0.54 mmol) was added to a solution of 15 (130 mg, 0.54 mmol) and $Cs_2CO_3$ (351 mg, 1.08 mmol) in DMF (3 mL) and the mixture was stirred overnight at room temperature. The mixture was then diluted with $H_2O$ and extracted with DCM. The combined organic layers were dried over $Na_2SO_4$, filtered and concentrated in vacuo. The crude product was flash silica gel column chromatographed (Hexane/EtOAc 9:1 to 5:5), affording 16 as a yellowish wax (108 mg, 56% yield).

¹H NMR (400 MHz, CDCl₃) δ: 7.44-7.36 (m, 4H), 7.34-7.30 (m, 1H), 7.14-7.10 (m, 2H), 6.92-6.98 (m, 2H), 5.04 (s, 2H), 3.21 (s, 2H), 2.77-2.69 (m, 4H), 2.44 (s, 3H), 1.47 (s, 9H).

N,N-(4-(Benzyloxy)phenethyl)(methyl)glycine hydrochloride (U) (PS-RG0064)

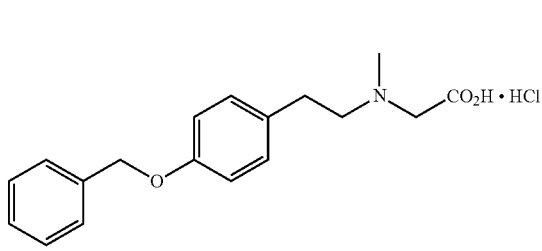

Chemical Formula: C$_{18}$H$_{21}$NO$_3$
Exact Mass: 299.15

Following the procedure for the preparation of compound C from 11C, compound U was obtained from 16 as a white powder (80 mg, 89% yield) after C-18 reverse phase chromatography (H$_2$O/MeOH, 90:10 to 30:70).

$^1$H NMR (400 MHz, MeOD) δ: 7.43-7.40 (m, 2H), 7.38-7.34 (m, 2H), 7.32-7.27 (m, 1H), 7.24-7.20 (m, 2H), 6.99-6.95 (m, 2H), 5.06 (s, 2H), 4.19-4.09 (m, 2H), 3.40 (br s, 2H), 3.05-3.01 (m, 2+3H).

$^{13}$C NMR (100 MHz, MeOD) δ: 168.4 (C$_{quat.}$), 159.6 (C$_{quat.}$), 138.8 (C$_{quat.}$), 131.1 (2CH), 129.6 (2CH), 129.4 (C$_{quat.}$), 129.0 (CH), 128.7 (2CH), 116.6 (2CH), 71.1 (CH$_2$), 59.4 (CH$_2$), 56.9 (CH$_2$), 42.2 (CH$_3$), 30.7 (CH$_2$).

HRMS: m/z calculated for C$_{18}$H$_{22}$NO$_3$$^+$: 300.15942, found: 300.15900.

Figure 3:
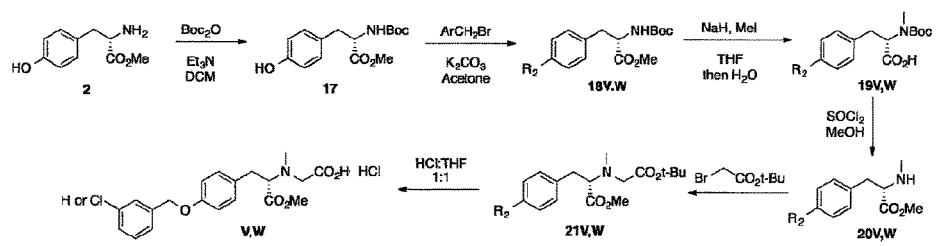
FIG. 3 shows a synthetic scheme for the preparation of polar deprenyl analogues V and W.

For FIG. 3 (compounds V and W)

N-(Boc)tyrosine methyl ester (17)

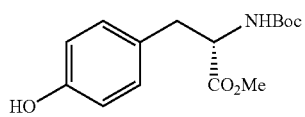

Chemical Formula: C$_{15}$H$_{21}$NO$_5$
Exact Mass: 295.14

Prepared according to a procedure described by Blacker, A. John et al. in *Eur. J. Org. Chem.* 2009, 3413-3426.

Compound 2 (3.5 g, 15.1 mmol) was suspended in DCM (50 mL), and cooled to 0° C. before triethylamine (4.2 mL, 30.2 mmol) was added dropwise. After 30 minutes a solution of Boc$_2$O (3.6 g, 16.6 mmol) in DCM (3 mL) was also added dropwise. The ice bath was removed and the reaction mixture was stirred overnight at room temperature. It was then quenched at 0° C. with H$_2$O, the layers were separated, and the organic layer was washed with water. The aqueous layers were extracted with DCM, and the combined organic layers were dried over Na$_2$SO$_4$, filtered, and concentrated in vacuo. The crude mixture was flash silica gel column chromatographed (Hexane/EtOAc 9:1 to 7:3), affording 17 as a colorless wax, which slowly turned into a white solid on standing (4.1 g, 91% yield).

$^1$H NMR (400 MHz, CDCl$_3$) δ: 6.98-6.94 (m, 2H), 6.73 (d, J=8.2 Hz, 2H), 5.00 (br d, J=8.0 Hz, 1H), 4.56-4.51 (m, 1H), 3.71 (s, 3H), 3.49 (s, 1H), 3.03 (dd, J=13.9, 5.7 Hz, 1H), 2.96 (dd, J=13.9, 6.1 Hz, 1H), 1.42 (s, 9H).

N-(Boc)(O-benzyloxy)tyrosine methyl ester (18V)

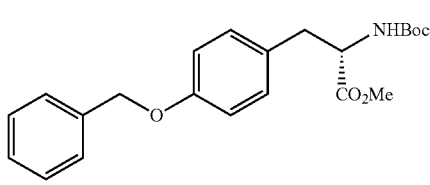

Chemical Formula: C$_{22}$H$_{27}$NO$_5$
Exact Mass: 385.19

Following the procedure used for the synthesis of 4A, compound 17 (1.0 g, 3.39 mmol) was converted to 18V, obtained as a white solid (1.3 g, 95% yield).

$^1$H NMR (400 MHz, CDCl$_3$) δ: 7.44-7.36 (m, 4H), 7.35-7.30 (m, 1H), 7.06-7.02 (m, 2H), 6.92-6.88 (m, 2H), 5.04 (s, 2H), 4.97 (br d, J=8.2 Hz, 1H), 4.57-4.52 (m, 1H), 3.71 (s, 3H), 3.08-2.97 (m, 2H), 1.42 (s, 9H).

N-(Boc)-N-(methyl)(O-benzyloxy)tyrosine (19V)

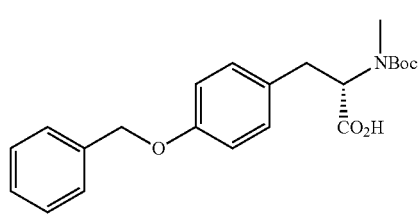

Chemical Formula: C$_{22}$H$_{27}$NO$_5$
Exact Mass: 385.19

To a solution of 18V (1.30 g, 3.37 mmol) and MeI (1.05 mL, 16.86 mmol) in dry THF (15 mL), cooled to 0° C., was added NaH (60% suspension in oil, 674 mg, 16.86 mmol) in portions. The resulting mixture was stirred overnight at room temperature and then cooled to 0° C. and quenched with ice water. After removal of the THF in vacuo, the residue was taken up in water and washed twice with hexane. The water layer was then acidified to pH 4 with citric acid and extracted with DCM. The combined organic layers washed with brine and water, dried over Na$_2$SO$_4$, filtered, and concentrated in vacuo. The crude mixture was flash silica gel column chromatographed (Hexane/EtOAc 6:4), affording 19V as a pale yellow oil (453 mg, 35% yield).

$^1$H NMR (400 MHz, CDCl$_3$) δ (mixture of atropoisomers): 7.44-7.36 (m, 4H), 7.34-7.30 (m, 1H), 7.14-7.09 (m, 2H), 6.93-6.89 (m, 2H), 5.04 (s, 2H), [4.76 (dd, J=10.8, 5.0 Hz, 1H)/4.56 (dd, J=10.8, 4.2 Hz, 1H] atropoisomers, [3.29-3.21 (m, 2H)/3.07 (dd, J=14.3, 11.1 Hz, 1H), 2.98 (dd, J=14.3, 11.1, 1H)] atropoisomers, [2.75 (s, 3H)/2.69 (s, 3H)] atropoisomers, [1.41 (s, 9H)/1.35 (s, 9H)] atropoisomers.

N-(methyl)(O-benzyloxy)tyrosine methyl ester (20V)

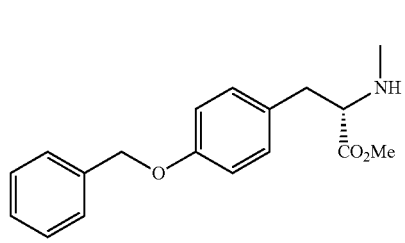

Chemical Formula: C$_{18}$H$_{21}$NO$_3$
Exact Mass: 299.15

Compound 19V (450 mg, 1.17 mmol) was dissolved in MeOH (6.0 mL) and cooled down to 0° C. before thionyl chloride (169 µL, 2.34 mmol) was added dropwise. The resulting solution was stirred overnight at room temperature. The solvent was then evaporated and the residue was dissolved in DCM and washed with 5% aqueous NaHCO$_3$, dried over Na$_2$SO$_4$, filtered, and concentrated in vacuo. Compound 20V was obtained as a pale yellow oil (245 mg, 62% yield).

$^1$H NMR (400 MHz, CDCl$_3$) δ: 7.44-7.36 (m, 4H), 7.34-7.30 (m, 1H), 7.10-7.07 (m, 2H), 6.92-6.88 (m, 2H), 5.04 (s, 2H), 3.67 (s, 3H), 3.41 (t, J=6.7 Hz, 1H), 2.94-2.86 (m, 2H), 2.36 (s, 3H), 1.66 (br s, 1H).

N-(tert-butyl acetate)-N-(methyl)(O-benzyloxy)tyrosine methyl ester (21V)

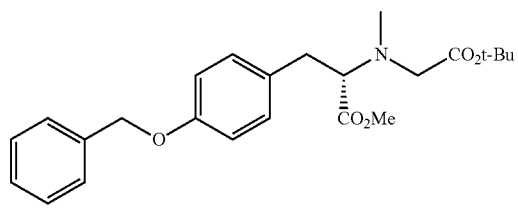

Chemical Formula: C$_{24}$H$_{31}$NO$_5$
Exact Mass: 413.22

Compound 20V (230 mg, 0.77 mmol) was dissolved in DMF (1.5 mL) and tert-butyl bromoacetate (114 µL, 0.77 mmol) was added dropwise. After 5 minutes of stirring, Cs$_2$CO$_3$ (501 mg, 1.54 mmol) was added and the resulting mixture was stirred overnight at room temperature. It was then diluted with a large amount of water and extracted with DCM. The organic layers were combined and dried over Na$_2$SO$_4$, filtered, and solvents were evaporated in vacuo. The crude product was purified through automated flash silica gel column (Hexane/EtOAc 9:1 to 7:3), affording 21V as a yellowish wax (157 mg, 49% yield).

$^1$H NMR (400 MHz, CDCl$_3$) δ: 7.44-7.35 (m, 4H), 7.34-7.29 (m, 1H), 7.15-7.11 (m, 2H), 6.90-6.87 (m, 2H), 5.02 (s, 2H), 3.59 (dd, J=9.4, 5.9 Hz, 1H), 3.59 (s, 3H), 3.42 (d, J=17.0 Hz, 1H), 3.26 (d, J=17.0 Hz, 1H), 2.99 (dd, J=13.4, 9.4 Hz, 1H), 2.93 (dd, J=13.4, 5.9 Hz, 1H), 2.48 (s, 3H), 1.47 (s, 9H).

N-Carboxymethyl)-N-(methyl-O-benzyloxytyrosine methyl ester hydrochloride (V) (PS-RG0123)

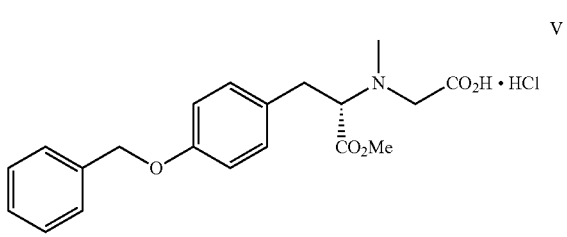

Chemical Formula: C$_{20}$H$_{23}$NO$_5$
Exact Mass: 357.16

Following the procedure for the preparation of compound C from 11C, compound V was obtained from 21V (100 mg, 0.24 mmol), as a white powder (82 mg, 86% yield) after C-18 reverse phase chromatography (H$_2$O/MeOH, 90:10 to 30:70).

$^1$H NMR (400 MHz, MeOD) δ: 7.42-7.39 (m, 2H), 7.37-7.32 (m, 2H), 7.31-7.26 (m, 1H), 7.16-7.12 (m, 2H), 6.96-6.89 (m, 2H), 5.03 (s, 2H), 3.89 (dd, J=8.4, 6.8 Hz, 1H), 3.59 (s, 3H), 3.58 (d, J=16.9 Hz, 1H), 3.48 (d, J=16.9 Hz, 1H), 3.09-2.99 (m, 2H), 2.62 (s, 3H).

$^{13}$C NMR (100 MHz, MeOD) δ: 173.0 (C$_{quat.}$), 172.3 (C$_{quat.}$), 159.4 (C$_{quat.}$), 138.8 (C$_{quat.}$), 131.4 (2CH), 130.2 (C$_{quat.}$), 129.6 (2CH), 129.0 (CH), 128.7 (2CH), 116.2 (2CH), 71.1 (CH$_2$), 69.3 (CH), 56.8 (CH$_2$), 52.4 (CH$_3$), 40.4 (CH$_3$), 35.5 (CH$_2$).

HRMS: m/z calculated for C$_{20}$H$_{24}$NO$_5$$^+$: 358.16490, found: 358.16473.

N-Carboxymethyl-N-methyl-O-3-chlorobenzyloxytyrosine methyl ester hydrochloride (W) (PS-RG0122)

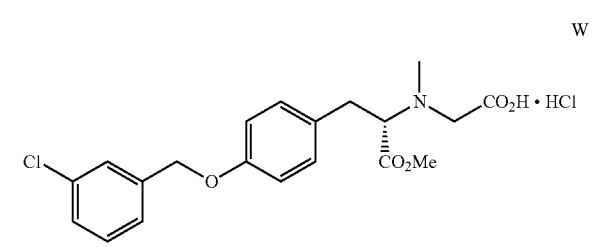

Chemical Formula: C$_{20}$H$_{22}$ClNO$_5$
Exact Mass: 391.12

Following the procedure for the preparation of compound C from 11C, compound W was obtained from 21W (100 mg, 0.22 mmol), as a yellow solid (72 mg, 75% yield) after C-18 reverse phase chromatography (H$_2$O/MeOH, 90:10 to 30:70).

$^1$H NMR (400 MHz, MeOD) δ: 7.43 (br s, 1H), 7.34-7.27 (m, 3H), 7.16-7.13 (m, 2H), 6.92-6.89 (m, 2H), 5.03 (s, 2H), 3.90 (t, J=7.6 Hz, 1H), 3.59 (d, J=16.9 Hz, 1H), 3.59 (s, 3H), 3.49 (d, J=16.9 Hz, 1H), 3.05-3.03 (m, 2H), 2.62 (s, 3H).

$^{13}$C NMR (100 MHz, MeOD) δ: 172.9 (C$_{quat.}$), 172.2 (C$_{quat.}$), 159.1 (C$_{quat.}$), 141.3 (C$_{quat.}$), 135.5 (C$_{quat.}$), 131.5 (2CH), 131.2 (CH), 130.4 (C$_{quat.}$), 129.0 (CH), 128.4 (CH), 126.8 (CH), 116.2 (2CH), 70.1 (CH$_2$), 69.3 (CH), 56.8 (CH$_2$), 52.4 (CH$_3$), 40.4 (CH$_3$), 35.5 (CH$_2$).

HRMS: m/z calculated for $C_{20}H_{24}NO_5^+$: 392.12593, found: 392.12552.

Figure 4:
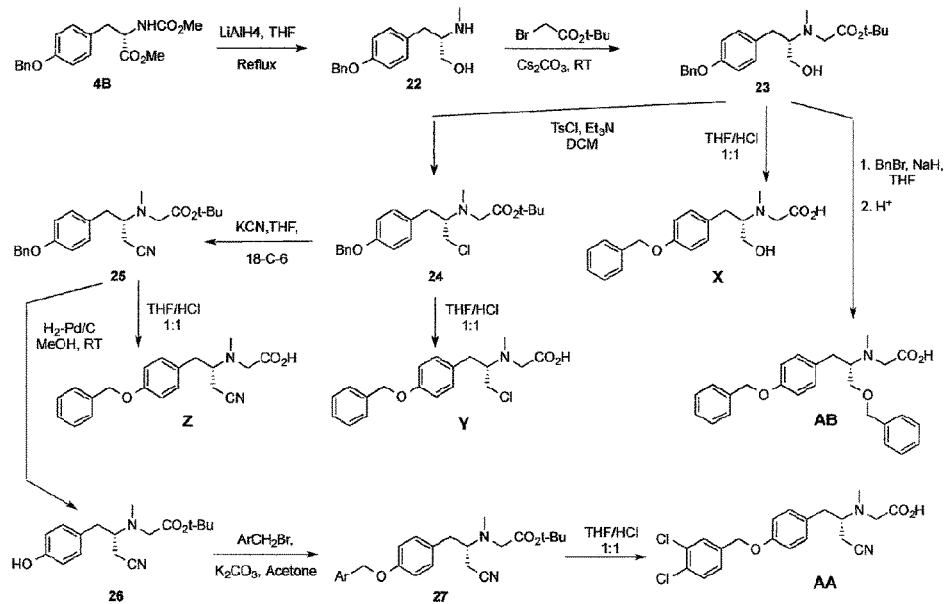
FIG. 4 shows a synthetic scheme for the preparation of polar deprenyl analogues X, Y, Z, AA, and AB.

For FIG. 4 (compounds X, Y, Z, AA, and AB)

(S)—N-(1-(4-(benzyloxy)phenyl)-3-hydroxypropan-2-yl)-N-methylamine 22

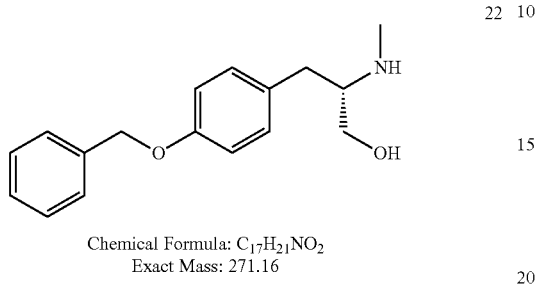

Chemical Formula: $C_{17}H_{21}NO_2$
Exact Mass: 271.16

Compound 4B (5.0 g, 14.6 mmol) was dissolved in dry THF (75 mL) and LiAlH4 (2.2 g, 58.2 mmol) was added by portion. The resulting suspension was stirred for 3 h at reflux. Once the reaction is complete it was successively quenched with water, 10% aqueous NaOH solution and water again (2.2 mL each). Once the solids in suspension turned white, they were filtered off and were washed with DCM and THF. The filtrate were then evaporated in vacuo and the residue was purified through flash silica gel column (Hexane:EtOAC 1:1 to EtOAc, then DCM:MeOH 7:3) affording a white solid (3.48 g, 88%).

$^1$H NMR (400 MHz, CDCl$_3$) δ: 7.44-7.31 (m, 5H), 7.10 (d, J=8.4 Hz, 2H), 6.92 (d, J=8.4 Hz, 2H), 5.05 (s, 2H), 3.64 (dd, J=10.8, 3.6 Hz, 1H), 3.34 (dd, J=10.8, 4.8 Hz, 1H), 2.78-2.64 (m, 2H+1H), 2.41 (s, 3H), 2.06 (br s, 2H).

tert-Butyl (S)—N-(1-(4-(benzyloxy)phenyl)-3-hydroxypropan-2-yl)-N-methylglycinate 23

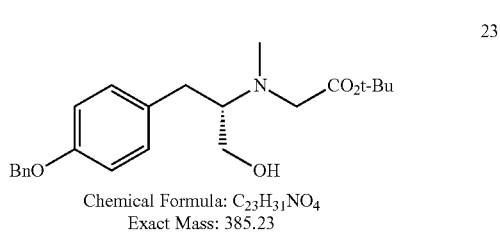 [SMILES: CN(CC(=O)OC(C)(C)C)[C@H](CO)Cc1ccc(OCc2ccccc2)cc1]

Chemical Formula: $C_{23}H_{31}NO_4$
Exact Mass: 385.23

To a solution of 22 (1.14 g, 4.20 mmol) in DMF (20 mL) was added Et3N (615 μL, 4.41 mmol) and tert-butyl bromoacetate (665 μL, 4.41 mmol). The mixture was stirred at room temperature overnight. DMF was removed by evaporation under vacuum. The residue was dissolved in DCM and washed with a solution of citric acid. The aqueous layer was extracted three times with DCM. Then the combined organic layers were successively washed with a saturated NaHCO3 solution, with brine and with water. The organic layers were dried over Na2SO4, filtered and concentrated under vacuum. The crude product was purified by automated flash chromatography (Hexane/EtOAc 70/30 to 50/50.) affording 23 as a colorless oil (1.30 g, 80%).

$^1$H NMR (400 MHz, CDCl$_3$) δ: 7.44-7.30 (m, 5H), 7.06 (d, J 8.4 Hz, 2H), 6.90 (d, J=8.4 Hz, 2H), 5.04 (s, 2H), 3.44 (dd, J=10.4, 4.4 Hz, 1H), 3.32 (br t, J=10.4 Hz, 1H), 3.28 (d, J=16.4 Hz, 1H), 3.13 (d, J=16.4 Hz, 1H), 3.01-2.94 (m, 1H), 2.78 (dd, J=13.6, 5.6 Hz, 1H), 2.43 (s, 3H), 2.35 (dd, J=13.6, 8.8 Hz, 1H), 1.47 (s, 9H).

(S)—N-(1-(4-(benzyloxy)phenyl)-3-hydroxypropan-2-yl)-N-methylglycine X (PS-RG0188)

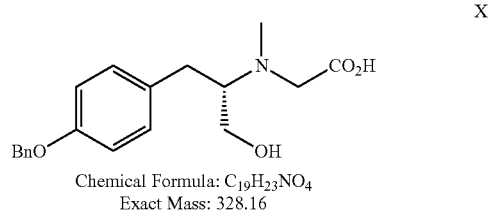 [SMILES: CN(CC(=O)O)[C@H](CO)Cc1ccc(OCc2ccccc2)cc1]

Chemical Formula: $C_{19}H_{23}NO_4$
Exact Mass: 328.16

Following the procedure for the preparation of compound C from 11C, compound X was obtained from 23 as a white powder (120 mg, 66% yield) after C-18 reverse phase chromatography (H$_2$O/MeOH, 90:10 to 30:70).

$^1$H NMR (400 MHz, MeOD) δ: 7.43-7.27 (m, 5H), 7.09 (d, J=8.6 Hz, 2H), 6.91 (d, J=8.6 Hz, 2H), 5.05 (s, 2H), 3.47 (dd, J=11.4, 10.0 Hz, 1H), 3.39 (dd, J=11.4, 3.8 Hz, 1H), 3.27 (d, J=15.5 Hz, 1H), 3.12 (d, J=15.5 Hz, 1H), 2.95 (br s, 1H), 2.84 (dd, J=13.4, 3.8 Hz, 1H), 2.39 (s, 3H), 2.28 (dd, J=13.4, 10.7 Hz, 1H).

$^{13}$C NMR (100 MHz, DMSO-d6) δ: 175.3 ($C_{quat.}$), 156.5 ($C_{quat.}$), 137.2 ($C_{quat.}$), 132.4 ($C_{quat.}$), 129.9 (2CH), 128.4 (2CH), 127.8 (CH), 127.7 (2CH), 114.6 (2CH), 69.1 (CH$_2$), 66.7 (CH), 59.7 (CH$_2$), 58.4 (CH$_2$), 37.1 (CH$_3$), 30.4 (CH$_2$).

tert-butyl (S)—N-(1(4-(benzyloxy)phenyl)-3-chloropropan-2-yl)-N-methylglycinate 24

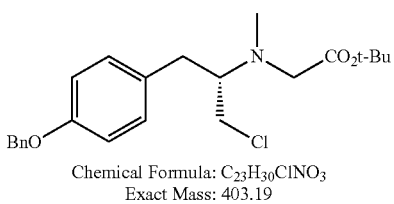

Chemical Formula: $C_{23}H_{30}ClNO_3$
Exact Mass: 403.19

To a solution of 23 (1.23 g, 3.20 mmol) in dry DCM (20 mL) was added Et3N (900 μL, 6.40 mmol) at 0° C. following by TsCl (1.22 g, 6.40 mmol) and DMAP (117 mg, 0.96 mmol). The mixture was stirred from 0° C. at room temperature overnight. Once the reaction is complete, the mixture was diluted with DCM and washed with a 10% citric solution. The organic phase was separated and the aqueous was extracted with DCM (3×). Then the combined organic phases were successively washed with a saturated NaHCO3 solution and with brine before being dried over Na2SO4, filtered and evaporated under vacuum. The crude product was purified by automated flash chromatography (Hexane to Hexane/EtOAc 85/15) affording 24 as a pale yellow oil (1.14 g, 88%).

$^1$H NMR (400 MHz, CDCl$_3$) δ: 7.45-7.31 (m, 5H), 7.18 (d, J=8.4 Hz, 2H), 6.93 (d, J=8.4 Hz, 2H), 5.05 (s, 2H), 4.16-4.10 (m, 1H), 3.31 (s, 2H), 3.20 (dd, J=14.4, 4.8 Hz, 1H), 2.90-2.85 (m, 3H), 2.49 (s, 3H), 1.47 (s, 9H).

(S)—N-(1-(4-(benzyloxy)phenyl)-3-chloropropan-2-yl)-N-methylglycine Y (PS-AD0095)

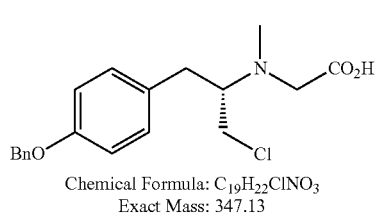

Chemical Formula: $C_{19}H_{22}ClNO_3$
Exact Mass: 347.13

Following the procedure for the preparation of compound C from 11C, compound X was obtained from 24 (84 mg, 0.21 mmol) as a yellow solid (24 mg, 30% yield) after C-18 reverse phase chromatography ($H_2O$/MeOH, 90:10 to 30:70).

$^1$H NMR (400 MHz, DMSO-d6) δ: 7.43-7.30 (m, 5H), 7.18 (d, J=8.4 Hz, 2H), 6.94 (d, J=8.4 Hz, 2H), 5.07 (s, 2H), 4.33-4.27 (m, 1H), 3.37-3.28 (m, 2H), 3.19 (dd, J=14.5, 3.9 Hz, 1H), 2.83 (d, J=6.3 Hz, 2H), 2.74 (dd, J=14.5, 8.9 Hz, 1H), 2.40 (s, 3H).

$^{13}$C NMR (100 MHz, DMSO-d6) δ: 171.9 ($C_{quat.}$), 157.0 ($C_{quat.}$), 137.2 ($C_{quat.}$), 130.4 (2CH), 130.0 ($C_{quat.}$), 128.4 (2CH), 127.8 (CH), 127.7 (2CH), 114.4 (2CH), 69.1 ($CH_2$), 62.1 ($CH_2$), 61.9 (CH), 57.8 ($CH_2$), 41.9 ($CH_3$), 40.5 ($CH_2$).

tert-butyl (S)—N-(1-(4-(benzyloxy)phenyl)-3-cyanopropan-2-yl)-N-methylglycinate 25

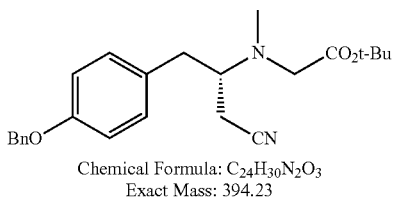

Chemical Formula: $C_{24}H_{30}N_2O_3$
Exact Mass: 394.23

To a solution of 24 (235 mg, 0.58 mmol) in dry DMF (2.5 mL) was added KCN (379 mg, 5.82 mmol), 18-crown-6 (31 mg, 0.12 mmol) and a catalytic amount of NaI. The mixture was stirred for 1 h30 at 100° C. under MW. Then the mixture was partitioned between DCM and a saturated NaHCO3 solution. The organic layer was successively washed with the saturated NaHCO3 solution and with brine before being dried over $Na_2SO_4$, filtered and evaporated under vacuum. Crude product was purified by automated flash chromatography (Hexane to Hexane/EtOAc 80/20) affording 25 as a pale yellow oil (183 mg, 80%).

$^1$H NMR (400 MHz, $CDCl_3$) δ: 7.45-7.31 (m, 5H), 7.14 (d, J=8.0 Hz, 2H), 6.93 (d, J=8.0 Hz, 2H), 5.05 (s, 2H), 3.39 (d, J=16.8 Hz, 1H), 3.33 (d, J=16.8 Hz, 1H), 3.26-3.20 (m, 1H), 3.02 (dd, J=13.6, 4.8 Hz, 1H), 2.67 (dd, J=13.6, 9.6 Hz, 1H), 2.53 (s, 3H), 2.46 (dd, J=17.2, 4.8 Hz, 1H), 2.37 (dd, J=17.2, 6.4 Hz, 1H), 1.48 (s, 9H).

$^{13}$C NMR (100 MHz, $CDCl_3$) δ: 170.3 ($C_{quat.}$), 157.6 ($C_{quat.}$), 136.9 ($C_{quat.}$), 130.3 ($C_{quat.}$), 130.0 (2CH), 128.5 (2CH), 127.9 (CH), 127.4 (2CH), 118.6 ($C_{quat.}$), 115.0 (2CH), 81.2 ($C_{quat.}$), 69.9 ($CH_2$), 61.6 (CH), 56.4 ($CH_2$), 37.8 ($CH_3$), 36.3 ($CH_2$), 28.0 (3$CH_3$), 18.8 ($CH_2$).

(S)—N-(1-(4-(benzyloxy)phenyl)-3-cyanopropan-2-yl)-N-methylglycine Z (PS-AD0186)

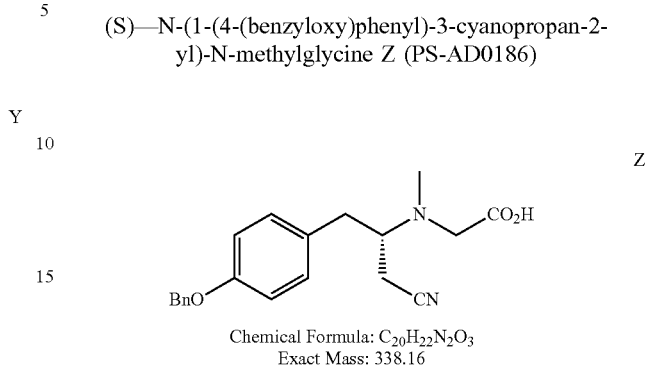

Chemical Formula: $C_{20}H_{22}N_2O_3$
Exact Mass: 338.16

Following the procedure for the preparation of compound C from 11C, compound Z was obtained from 25 (74 mg, 0.18 mmol) as a white solid (54 mg, 77%) after C-18 reverse phase chromatography ($H_2O$/MeOH, 90:10 to 30:70).

$^1$H NMR (400 MHz, MeOD) δ: 7.41-7.27 (m, 5H), 7.20 (d, J=8.3 Hz, 2H), 6.95 (d, J=8.3 Hz, 2H), 5.03 (s, 2H), 3.60-3.50 (m, 3H), 3.10 (dd, J=13.3, 5.0 Hz, 1H), 2.79 (dd, J=13.3, 9.8 Hz, 1H), 2.75-2.62 (m, 2H), 2.69 (s, 3H).

$^{13}$C NMR (100 MHz, MeOD) δ: 172.6 ($C_{quat.}$), 159.5 ($C_{quat.}$), 138.8 ($C_{quat.}$), 131.5 (2CH), 130.1 ($C_{quat.}$), 129.7 (2CH), 129.0 (CH), 128.7 (2CH), 119.1 ($C_{quat.}$), 116.5 (2CH), 71.1 ($CH_2$), 63.6 (CH), 57.2 ($CH_2$), 38.8 ($CH_3$), 36.2 ($CH_2$), 18.8 ($CH_2$).

(S)—N-(1-cyano-3-(4-hydroxyphenyl)propan-2-yl)-N-methylglycine 26

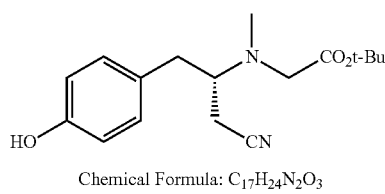

Chemical Formula: $C_{17}H_{24}N_2O_3$
Exact Mass: 304.18

Following the procedure outlined in FIG. 1 for the preparation of compound 10 from 9B, the corresponding compound 26 was prepared from 25 (213 mg, 0.54 mmol). Compound 26 was obtained as a colorless oil which solidified upon standing (148 mg, 90%).

$^1$H NMR (400 MHz, $CDCl_3$) δ: 7.06 (d, J=8.0 Hz, 2H), 6.77 (d, J=8.0 Hz, 2H), 5.43 (br s, OH), 3.38 (d, J=16.8 Hz, 1H), 3.33 (d, J=16.8 Hz, 1H), 3.22-3.17 (m, 1H), 2.99 (dd, J=13.6, 4.8 Hz, 1H), 2.64 (dd, J=13.6, 9.6 Hz, 1H), 2.52 (s, 3H), 2.46 (dd, J=17.0, 4.8 Hz, 1H), 2.36 (dd, J=17.0, 6.2 Hz, 1H), 1.47 (s, 9H).

tert-butyl-(S)—N-(1-cyano-3-(4-((3,4-dichlorobenzyl)oxy)phenyl)propan-2-yl)-N-methylglycinate 27

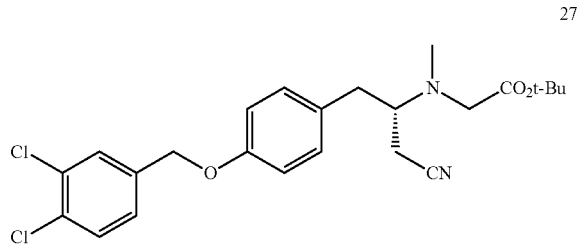

Chemical Formula: $C_{24}H_{28}Cl_2N_2O_3$
Exact Mass: 462.15

To a solution of 26 (131 mg, 0.43 mmol) in dry DMF (2 mL) were successively added K2CO3 (179 mg, 1.29 mmol) and 3,4-dichlorobenzyl bromide (83 µL, 0.56 mmol) under nitrogen. The reaction was stirred at room temperature overnight. The crude mixture was filtered through a pad of Celite and rinse with DCM. The filtrated was evaporated under vacuum. Crude product was purified by automated flash chromatography (Hexane/EtOAc 90/10 to 75/25) affording 27 as a colorless oil (175 mg, 88%).

$^1$H NMR (400 MHz, CDCl$_3$) δ: 7.53 (s, 1H), 7.45 (d, J=8.4 Hz, 1H), 7.25 (d, J=8.4 Hz, 1H), 7.14 (d, J=8.4 Hz, 2H), 6.88 (d, J=8.4 Hz, 2H), 4.99 (s, 2H), 3.38 (d, J=17.0 Hz, 1H), 3.32 (d, J=17.0 Hz, 1H), 3.26-3.19 (m, 1H), 3.02 (dd, J=13.6, 5.2 Hz, 1H), 2.68 (dd, J=13.6, 9.2 Hz, 1H), 2.52 (s, 3H), 2.46 (dd, J=17.2, 4.8 Hz, 1H), 2.37 (dd, J=17.2, 6.0 Hz, 1H), 1.47 (s, 9H).

$^{13}$C NMR (100 MHz, CDCl3) δ: 170.3 ($C_{quat.}$), 157.1 ($C_{quat.}$), 137.3 ($C_{quat.}$), 132.7 ($C_{quat.}$), 131.9 ($C_{quat.}$), 130.8 ($C_{quat.}$), 130.6 (CH), 130.2 (2CH), 129.2 (CH), 126.5 (CH), 118.6 ($C_{quat.}$), 115.0 (2CH), 81.3 ($C_{quat.}$), 68.5 (CH$_2$), 61.6 (CH), 56.4 (CH$_2$), 37.8 (CH$_3$), 36.4 (CH$_2$), 28.1 (3CH$_3$), 18.9 (CH$_2$).

(S)—N-(1-cyano-3-(4-((3,4-dichlorobenzyl)oxy)phenyl)propan-2-yl)-N-methylglycine AA (PS-AD0191)

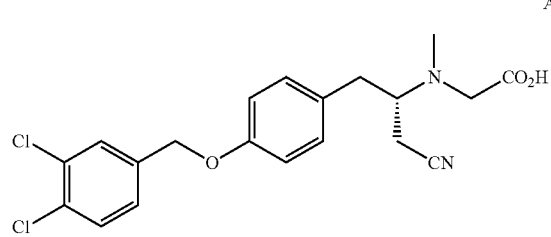

Chemical Formula: $C_{20}H_{20}Cl_2N_2O_3$
Exact Mass: 406.09

Following the procedure for the preparation of compound C from 11C, compound AA was obtained from 27 (162 mg, 0.44 mmol) as a white solid (120 mg, 66%) after C-18 reverse phase chromatography (H$_2$O/MeOH, 90:10 to 30:70).

$^1$H NMR (400 MHz, MeOD) δ: 7.58 (s, 1H), 7.49 (d, J=8.2 Hz, 1H), 7.33 (d, J=8.2 Hz, 1H), 7.22 (d, J=8.2 Hz, 2H), 6.95 (d, J=8.2 Hz, 2H), 5.03 (s, 2H), 3.57-3.48 (m, 3H), 3.10 (dd, J=13.3, 3.8 Hz, 1H), 2.79 (dd, J=13.3, 9.9 Hz, 1H), 2.74-2.62 (m, 2H), 2.66 (s, 3H).

$^{13}$C NMR (100 MHz, MeOD) δ: 173.1 ($C_{quat.}$), 159.1 ($C_{quat.}$), 139.8 ($C_{quat.}$), 133.5 ($C_{quat.}$), 132.6 ($C_{quat.}$), 131.8 (CH), 131.6 (2CH), 130.9 ($C_{quat.}$), 130.4 (CH), 128.3 (CH), 119.3 ($C_{quat.}$), 116.5 (2CH), 69.5 (CH$_2$), 63.6 (CH), 57.2 (CH$_2$), 38.7 (CH$_3$), 36.4 (CH$_2$), 18.8 (CH$_2$).

HRMS: m/z calculated for $C_{20}H_{20}Cl_2N_2O_3^-$: 405.07782, found: 405.07819.

(S)—N-(1-(benzyloxy)-3-(4-((3,4-dichlorobenzyl)oxy)phenyl)propan-2-yl)-N-methylglycine AB (PS-RG0221)

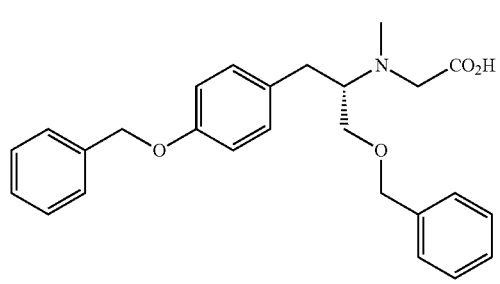

Chemical Formula: $C_{26}H_{29}NO_4$
Exact Mass: 419.21

Compound 23 (200 mg, 0.52 mmol) was put in solution in dry THF and cooled down to 0° C. before NaH (60% suspension in oil, 42 mg, 1.04 mmol) was added. After 10 min of stirring, benzyl bromide (93 µL, 0.78 mmol) was added dropwise and the resulting solution was stirred overnight at r.t. It was then cooled down to 0° C. and conc. HCl (20 mL) was added dropwise. The resulting solution was stirred for an additional 2 h before solvents were removed in vacuo. The crude product was purified through 2 successive reverse phase C18 columns (H$_2$O/MeOH 90:10 to 5:95 and then 50:50 to 20:80), affording AB as a white solid (108 mg, 46%).

$^1$H NMR (400 MHz, MeOD) δ: 7.43-7.42 (m, 2H), 7.38-7.27 (m, 8H), 7.15 (d, J=8.6 Hz, 2H), 6.94 (d, J=8.6 Hz, 2H), 5.06 (s, 2H), 4.55 (d, J=11.7 Hz, 1H), 4.45 (d, J=11.7 Hz, 1H), 3.83-3.68 (m, 3H), 3.64 (dd, J=11.7, 2.9 Hz, 1H), 3.55 (dd, J=11.7, 7.1 Hz, 1H), 3.07 (dd, J=13.3, 4.6 Hz, 1H), 2.93 (s, 3H), 2.90 (dd, J=13.3, 10.9 Hz, 1H).

$^{13}$C NMR (100 MHz, MeOD) δ: 170.0 ($C_{quat.}$), 159.7 ($C_{quat.}$), 138.8 ($C_{quat.}$), 138.6 ($C_{quat.}$), 131.5 (2CH), 129.74 (2CH), 129.66 (2CH), 129.4 (2CH), 129.3 (CH), 129.0

(CH), 128.9 ($C_{quat.}$), 128.7 (2CH), 116.6 (2CH), 74.5 ($CH_2$), 71.1 ($CH_2$), 67.4 (CH), 66.6 ($CH_2$), 58.1 ($CH_2$), 39.9 ($CH_3$), 32.1 ($CH_2$).

Figure 5:
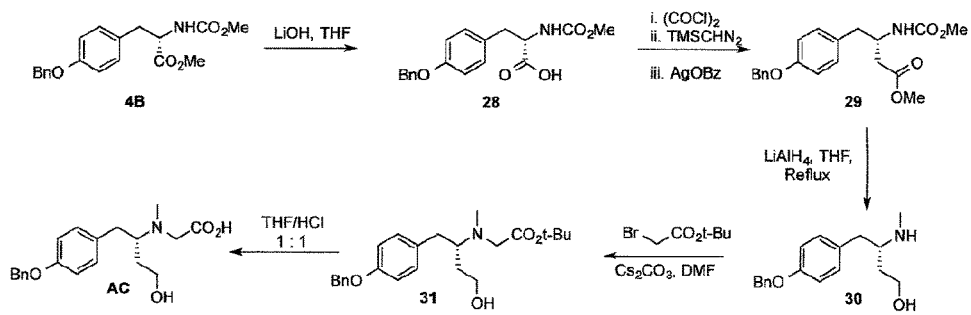
FIG. 5 shows a synthetic scheme for the preparation of polar deprenyl analogue AC.

For FIG. 5 (compound AC)

(S)-3-(4-(benzyloxy)phenyl)-2-((methoxycarbonyl)amino)propanoic acid 28

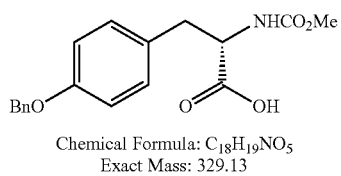

Chemical Formula: $C_{18}H_{19}NO_5$
Exact Mass: 329.13

Compound 4B (2.06 g, 6.0 mmol) was dissolved in THF (10 mL) and LiOH (0.50 g, 21.0 mmol), pre-dissolved in water (5 mL), was added in one portion. The suspension mixture was stirred at room temperature for 2 h30. The solution was acidified to pH=4 with a solution of KHSO4 1M. The mixture became blurry and white and was partitioned between DCM and water. The aqueous layer was extracted with DCM (three times). The combined organic layers were dried over Na2SO4, filtered and evaporated under vacuum. The crude product was engaged in the next step without further purification. Compound 28 was obtained as a white solid (2.0 g, 100%).

$^1$H NMR (400 MHz, $CDCl_3$) δ: 7.42-7.30 (m, 5H), 7.09 (d, J=8.2 Hz, 2H), 6.91 (d, J=8.2 Hz, 2H), 5.10 (br d, J=7.6 Hz, 1H), 5.03 (s, 2H), 4.66-4.62 (m, 1H), 3.67 (s, 3H), 3.16-3.04 (m, 2H).

(S)-4-(4-(benzyloxy)phenyl)-3-((methoxycarbonyl)amino)butanoic acid 29

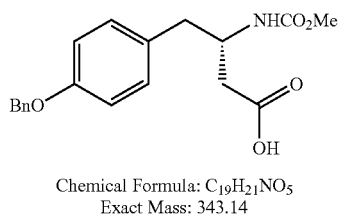

Chemical Formula: $C_{19}H_{21}NO_5$
Exact Mass: 343.14

The homologated ester 29 was obtained from 28 in three steps.

First step (acyl chloride formation): 28 (1.52 g, 4.62 mmol) was suspended in dry DCM (17 mL) and cooled down to 0° C. Oxalyl chloride (590 μL, 6.93 mmol) was added to the solution at 0° C. following by 5 drops of DMF. The mixture was stirred at room temperature overnight. The solvent was evaporated under vacuum and the crude was directly engaged in the next step.

Second step (diazoketone formation): The previous acyl chloride crude (1.60 g, 4.62 mmol) was dissolved in dry THF (20 mL) under N2 atmosphere. The solution was cooled down to −10° C. and a 2M solution of TMSD in Et2O (5.2 mL, 10.4 mmol) was added dropwise followed by Et3N (1.44 mL, 10.4 mmol). The solution was stirred from −10° C. to rt for 20 h. The reaction mixture was diluted with DCM and washed successively with a saturated NaHCO3 solution and a saturated NH4Cl solution. The organic layer was dried over Na2SO4, filtered and evaporated under vacuum. The crude product can be engaged directly in the next step without further purification.

Third step (homologated ester formation): To a solution of the former diazoketone (161 mg, 0.46 mmol) in MeOH (2 mL) was added a solution of AgOBz (63 mg, 0.27 mmol) in Et3N (1.21 mL, 8.66 mmol). The black mixture was stirred at room temperature overnight hidden from light. Then the solvent was evaporated under vacuum and the crude was partitioned between DCM and a 10% citric acid solution. The organic layer was then washed with a saturated NaHCO3 solution before being dried over Na2SO4, filtered and evaporated under vacuum. The crude product was purified by automated flash chromatography. (Hexane to Hexane/EtOAc 80/20) affording 29 as a pale yellow oil (82 mg, 48%).

$^1$H NMR (400 MHz, $CDCl_3$) δ: 7.44-7.30 (m, 5H), 7.10 (d, J=8.2 Hz, 2H), 6.92 (d, J=8.2 Hz, 2H), 5.28 (br s, 1H), 5.04 (s, 2H), 4.17 (br d, J=5.6 Hz, 1H), 3.68 (s, 3H), 3.64 (s, 3H), 2.91-2.85 (m, 1H), 2.80-2.75 (m, 1H), 2.55-2.45 (m, 1H). 4.66-4.62 (m, 1H).

$^{13}$C NMR (100 MHz, CDCl3) δ: 171.9 ($C_{quat.}$), 157.5 ($C_{quat.}$), 156.1 ($C_{quat.}$), 137.1 ($C_{quat.}$), 130.2 (2CH), 129.7 ($C_{quat.}$), 128.5 (2CH), 127.8 (CH), 127.4 (2CH), 114.8 (2CH), 69.8 ($CH_2$), 51.9 ($CH_3$), 51.6 ($CH_3$), 49.3 (CH), 39.3 ($CH_2$), 37.2 ($CH_2$).

(S)-4-(4-(benzyloxy)phenyl)-3-(methylamino)butan-1-ol 30

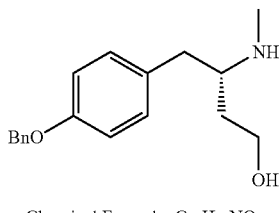

Chemical Formula: $C_{18}H_{23}NO_2$
Exact Mass: 285.17

The ester 29 (200 mg, 0.57 mmol) was dissolved in dry THF (3 mL). LiAlH4 (129 mg, 3.39 mmol) was added in few portions at 0° C. Then the mixture was heated at reflux overnight. Once the reaction was complete, the mixture was quenched by a sequential addition of water, 10% solution of NaOH, and water again. After one hour of stirring at 0° C. the white suspension was filtered through a pad of Celite and rinsed with DCM. The filtrate was evaporated under vacuum. The crude product was purified by automated flash chromatography (DCM to DCM/MeOH 94/6) affording a colorless oil which solidified upon standing (82 mg; 51%).

$^1$H NMR (400 MHz, MeOD) δ: 7.42-7.27 (m, 5H), 7.12 (d, J=8.4 Hz, 2H), 6.93 (d, J=8.4 Hz, 2H), 5.04 (s, 2H), 3.69-3.57 (m, 2H), 2.84-2.73 (m, 2H), 2.61 (dd, J=13.2, 7.2 Hz, 1H), 2.37 (s, 3H), 1.67-1.57 (m, 2H).

$^{13}$C NMR (100 MHz, MeOD) δ: 158.9 ($C_{quat.}$), 138.8 ($C_{quat.}$), 132.4 ($C_{quat.}$), 131.3 (2CH), 129.5 (2CH), 128.8

(CH), 128.5 (2CH), 116.1 (2CH), 71.0 (CH$_2$), 60.9 (CH$_2$), 60.7 (CH), 40.0 (CH$_2$), 35.9 (CH$_2$), 33.4 (CH$_3$).

tert-butyl (S)—N-(1-(4-(benzyloxy)phenyl)-4-hydroxybutan-2-yl)-N-methylglycinate 31

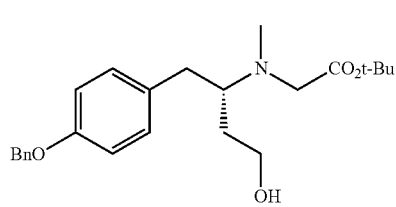

Chemical Formula: C$_{24}$H$_{33}$NO$_4$
Exact Mass: 399.24

Following the procedure outlined in FIG. 4 for the preparation of compound 23 from 22, the corresponding compound 31 was prepared from 30 (81 mg, 0.28 mmol). Compound 31 was obtained without further purification as a colorless oil (107 mg, 94%).

$^1$H NMR (400 MHz, CDCl$_3$) δ: 7.43-729 (m, 5H), 7.03 (d, J=8.0 Hz, 2H), 6.89 (d, J=8.0 Hz, 2H), 5.02 (s, 2H), 3.73-3.64 (m, 2H), 3.33 (d, J=16.2 Hz, 1H), 3.17 (d, J=16.2 Hz, 1H), 2.92-2.84 (m, 3H), 2.39 (br s, 3H), 2.26 (dd, J=12.8, 10.0 Hz, 1H), 1.74-1.64 (m, 1H), 1.48 (s, 9H).

(S)—N-(1-(4-(benzyloxy)phenyl)-4-hydroxybutan-2-yl)-N-methylglycine AC (PS-AD0179)

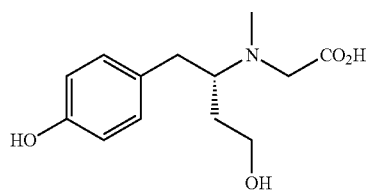

Chemical Formula: C$_{20}$H$_{25}$NO$_4$
Exact Mass: 343.18

Following the procedure for the preparation of compound C from 11C, compound AC was obtained from 31 (30 mg, 0.08 mmol) as a white solid (12 mg, 42%) after C-18 reverse phase chromatography (H$_2$O/MeOH, 90:10 to 30:70).

$^1$H NMR (400 MHz, MeOD) δ: 7.43-7.28 (m, 5H), 7.21 (d, J=8.2 Hz, 2H), 6.98 (d, J=8.1 Hz, 2H), 5.06 (s, 2H), 3.76-3.69 (m, 4H), 3.59 (br td, J=10.7, 2.3 Hz, 1H), 3.14 (dd, J=13.4, 3.8 Hz, 1H), 2.92 (s, 3H), 2.76 (dd, J=13.4, 10.7 Hz, 1H), 2.06-1.95 (m, 1H), 1.68 (br dd, J=15.6, 2.6 Hz, 1H).

$^{13}$C NMR (100 MHz, MeOD) δ: 169.7 (C$_{quat.}$), 159.8 (C$_{quat.}$), 138.7 (C$_{quat.}$), 131.5 (2CH), 129.5 (2CH), 129.3 (C$_{quat.}$), 128.9 (CH), 128.6 (2CH), 116.5 (2CH), 71.0 (CH$_2$), 69.4 (CH), 61.3 (CH$_2$), 57.7 (CH$_2$), 37.9 (CH$_3$), 34.8 (CH$_2$), 30.8 (CH$_2$).

Figure 6:
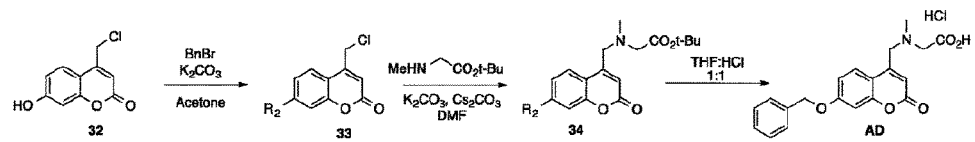
FIG. 6 shows a synthetic scheme for the synthesis of coumarin derivative AD.

For FIG. 6 (compound AD

4-Chloromethyl-7-hydroxycoumarin (32)

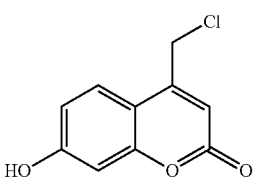

Chemical Formula: C$_{10}$H$_7$ClO$_3$
Exact Mass: 210.01

Prepared according to Carotti, A. et al., *J. Med. Chem.* 2009, 52, 6685-6706

4-Chloromethyl-7-benzyloxycoumarin (33)

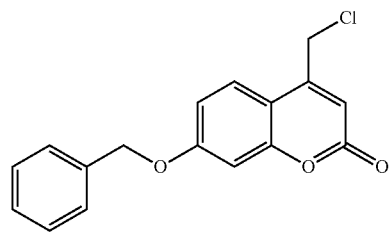

Chemical Formula: C$_7$H$_{13}$ClO$_3$
Exact Mass: 300.06

Prepared according to Caroni, A. et al., *J. Med. Chem.* 2009, 52, 6685-6706 tert-Butyl N-((7-(benzyloxy)-2-oxo-2H-chromen-4-yl)methyl)-N-methylglycinate (34)

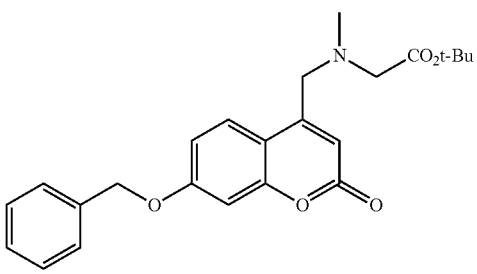

Chemical Formula: C$_{24}$H$_{27}$NO$_5$
Exact Mass: 409.19

Sarcosine tert-butylester hydrochloride (217 mg, 1.2 mmol) in DMF (2 mL) containing K$_2$CO$_3$ (207 mg, 1.5 mmol) was stirred for 5 minutes (the solution turned clear).

Compound 33 (300 mg, 1.0 mmol) was added, followed 5 min later by $Cs_2CO_3$ (488 mg, 1.5 mmol), and the mixture was stirred overnight at room temperature in the absence of light. The mixture was then diluted with water, extracted with DCM and concentrated in vacuo. The crude product mixture flash silica gel column chromatographed (Hexane/EtOAc 8:2 to 5:5), affording 34 as a yellow wax (141 mg, 35% yield).

$^1$H NMR (400 MHz, $CDCl_3$) δ: 7.90 (d, J=8.8 Hz, 1H), 7.44-7.32 (m, 5H), 6.92 (dd, J=8.8, 2.5 Hz, 1H), 6.88 (d, J=2.5 Hz, 1H), 6.34 (t, J=1.0 Hz, 1H), 5.13 (s, 2H), 3.82 (d, J=1.0 Hz, 2H), 3.27 (s, 2H), 2.42 (s, 3H), 1.49 (s, 9H).

$^{13}$C NMR (100 MHz, $CDCl_3$) δ: 170.2 ($C_{quat.}$), 161.8 ($C_{quat.}$), 161.7 ($C_{quat.}$), 155.7 ($C_{quat.}$), 152.8 ($C_{quat.}$), 136.1 ($C_{quat.}$), 128.9 (2CH), 128.5 (CH), 127.7 (2CH), 126.5 (CH), 113.1 (CH), 112.8 ($C_{quat.}$), 112.4 (CH), 102.1 (CH), 81.6 ($C_{quat.}$), 70.6 ($CH_2$), 59.1 ($CH_2$), 57.6 ($CH_2$), 42.4 ($CH_3$), 28.4 (3$CH_3$).

MS: 432.2 $[M+Na]^+$, 410.2 $[M+H]^+$

N-((7-(benzyloxy)-2-oxo-2H-chromen-4-yl)methyl)-N-methylglycine hydrochloride (R) (PS-RG0098)

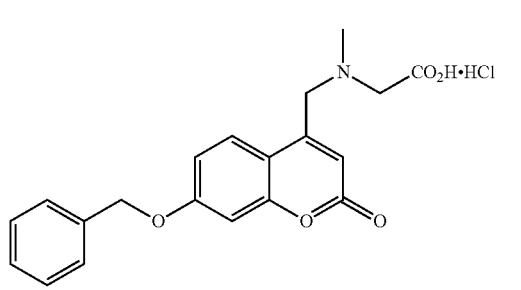

Chemical Formula:
Exact Mass:

Following the procedure for the preparation of compound C from 11C, compound AD was obtained from corresponding tert-butylester 34 (75 mg, 0.18 mmol) as a dark beige powder (46 mg, 64% yield) after trituration in DCM.

$^1$H NMR (400 MHz, MeOD) δ: 8.00 (d, J=8.9 Hz, 1H), 7.48-7.45 (m, 2H), 7.41-7.37 (m, 2H), 7.35-7.31 (m, 1H), 7.12 (dd, J=8.9, 2.5 Hz, 1H), 7.08 (d, J=2.5 Hz, 1H), 6.55 (s, 1H), 5.23 (s, 2H), 4.65 (br s, 2H), 4.31 (s, 2H), 3.00 (s, 3H).

$^{13}$C NMR (100 MHz, MeOD) δ: 168.7 ($C_{quat.}$), 164.4 ($C_{quat.}$), 161.8 ($C_{quat.}$), 157.4 ($C_{quat.}$), 145.7 ($C_{quat.}$), 137.7 ($C_{quat.}$), 129.8 (2CH), 129.5 (CH), 128.9 (2CH), 127.4 (CH), 117.9 (CH), 114.9 (CH), 112.7 ($C_{quat.}$), 103.7 (CH), 71.9 ($CH_2$), 57.9 ($CH_2$), 56.4 ($CH_2$), 42.8 ($CH_3$).

HRMS: m/z calculated for $C_{20}H_{20}NO_5^+$: 354.13360, found: 354.13342.

Further embodiments are described with reference to the following, non-limiting, examples.

EXAMPLES

Example 1—Synthesis of MAO-B Inhibitors with Limited BBB Permeability

In common with the biogenic amines dopamine and norepinephrine (MAO substrates), and different synthetic phenyethylamine type compounds (ex. amphetamine), the ability of deprenyl to cross the BBB is related to its lipophilic character/polar surface area.

To separate the desired peripheral MAO-B activity from CNS-based MAO activities, the inventors set out to design polar deprenyl analogues with reduced ability to penetrate the BBB, but which maintain selective affinity for MAO-B. Analysis of structural data for MAOA/MAOB in complex with different classes of inhibitors, suggests that polar modifications can be made to three regions of the molecule (FIG. 7): replacement of the acetylene motif (Zone 1), modification of the tertiary nitrogen (Zone 2), and functionalization of the aromatic ring (Zone 3).

Figure 8:
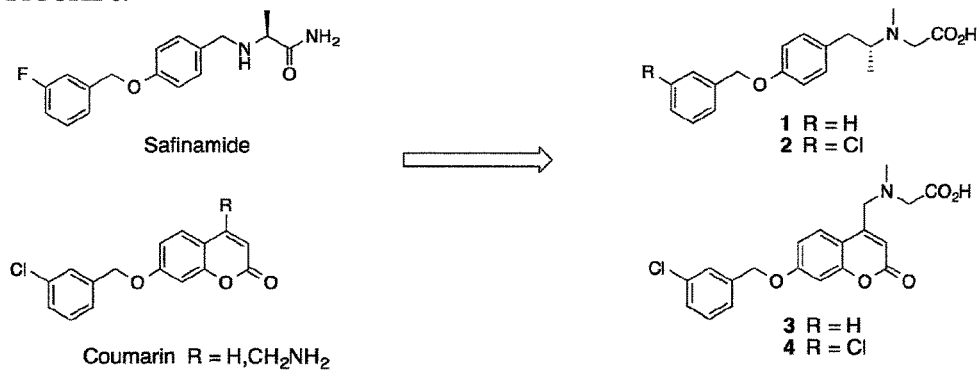
FIG. 8 shows molecules 1 to 4 as derived from Safinamide and Coumarin.

Considering these options, there was an initial focus on replacement of the acetylene group (which in deprenyl irreversibly reacts with the FAD co-factor) by a carboxylic acid function ($CO_2H$), as this motif could engage in formation of a stable salt-bridge type interaction with the FAD co-factor. However, in silico modeling of BBB-drug interactions (ADMET predictor; Simulations Plus™) predicted that this simple polar modification may be insufficient to completely block BBB penetration (TABLE 2). Fortunately, "larger" molecules also bearing a phenoxy or benzyloxy motif at C-4 of the aromatic ring (entries 4 & 5) are predicted to not cross the BBB. It is of significance that a significant increase in MAO-B selectivity is achieved by meta-H→Cl substitution in the benzyloxy substituent in safinamide and in the highly lipophilic coumarin-type MAO-B inhibitors. The prototype phenethylamine compounds 1 and 2, and the corresponding coumarin derivatives 3 and 4 were thus prepared and evaluated (FIG. 8). As anticipated, all four benzyloxy substituted molecules are potent MAO inhibitors. Further, the m-chloro substituent accentuates MAO-B selectivity, and these molecules show reduced ability to penetrate the BBB relative to deprenyl (see EXAMPLE 2). To develop novel polar in vivo active and selective MAOB inhibitors that act outside the CNS, the inventors continued the exploration of different structural modifications in zones 1 to 3 of deprenyl. Several potential modifications are already indicated in FIG. 8, and the predicted ability of these compounds to pass, or not, through the BBB is presented in TABLE 2. A number of different overlapping types of modifications may thus be suitable for reducing BBB permeability while maintaining MAO-B selectivity.

Figure 7:
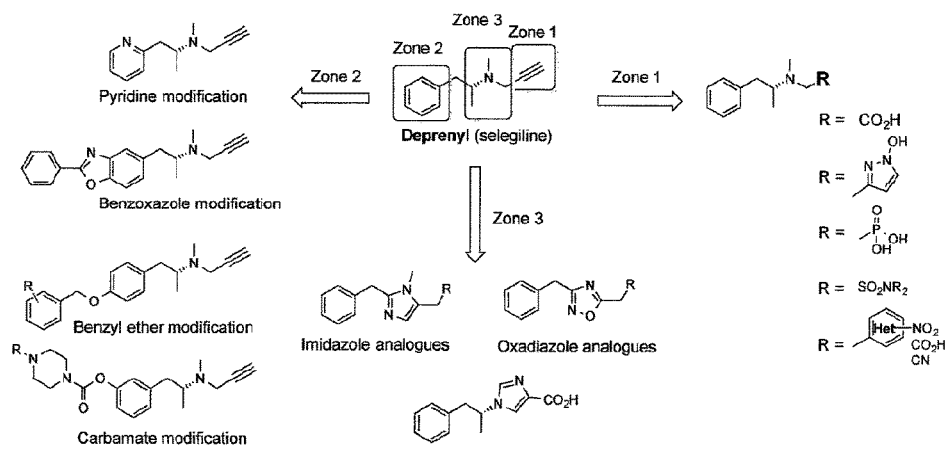
FIG. 7 shows a schematic of the three zones in deprenyl where modifications have been made to create new polar analogues that maintain affinity for MAO B, while losing or reducing the ability to cross the BBB.

TABLE 2 shows in silico calculations of blood brain barrier (BBB) permeability for deprenyl analogues. Box A corresponds to analogues modified in zone 1 (FIG. 7). Boxes B and C correspond to analogues modified in zones 1 and 2. Box D illustrates the evolution of deprenyl toward the coumarin system (compound 11). Box D corresponds to analogues modified in zone 3.

TABLE 2

| | Compound | BBB filter | LogBBB |
|---|---|---|---|
| | Deprenyl | High | +0.44 |
| 1. | | High | −1.052 |
| 2. | | High | −0.801 |
| 3. | | High | −1.082 |
| 4. | | Low | −1.124 |
| 5. | | Low | −xxxx |
| 6. | | xxx | xxxxx |
| 7. | | Low | −1.183 |
| 8a,b. | R = H / R = OBn | High / Low | −0.961 / −1.041 |

TABLE 2-continued

| Compound | | BBB filter | LogBBB |
|---|---|---|---|
| 9a,b. | R = H<br>R = OBn | High<br>Low | −0.334<br>−0.445 |
| 9. | | High | −1.190 |
| 10. | | Low | xxxx |
| 11. | | Low | xxxxx |
| 12. | R = H<br>R = OBn | High<br>Low | −1.287<br>−1.336 |
| 13. | | Low | −1.012 |

Modification 1 determining whether the $CO_2H$ modification in zone 1 is optimal by evaluating it relative to other polar motifs as alternatives to the acetylene function in deprenyl. Included are polar heterocycle motifs, such as N-hydroxypyrazole (Entry (9a,b; TABLE 2), which can potentially interact with both the FAD co-factor and the multiple aromatic residues that line the substrate cavity. The arrangement of these residues (Tyr60, 188, 398, 435, Phe343 and Trp388) in the substrate pocket (not shown) for the coumarin type MAO-B inhibitors.

Modification 2 replacement of the side chain methyl group, or the C-2 Ar—H, by an ester/amide or ester/amide bioisostere motif (Entries 10-12; TABLE 2) in order to capture the favourable binding interactions observed for the coumarin-based MAO-B inhibitors (see Entry 13; TABLE 2), and impart increased polar character/water solubility to the molecule.

Modification 3 incorporation of the tertiary nitrogen in deprenyl into a heterocyclic ring (ex. imidazole) so as to change its electronic (redox) properties (Entries 14-15; TABLE 2).

Modification 4 incorporation of polar substituents/motifs onto different positions on the phenyl ring and polar atom (C→N) exchange(s) in the phenyl ring of deprenyl. A great many options exist for these modifications (see FIG. 7 for selected examples). It is now understood that, in contrast to MAO-A, the binding/active site in MAO-B is divided into two distinct cavities (not shown): a "substrate" cavity close to the FAD co-factor, and an "entrance" cavity (or $I_2$-binding site) that connects to the enzyme surface. These two binding pockets are separated by two "gate" residues (Ile199, Tyr326), which form a constriction point. Each has different properties (composition, lipophilicity, shape, etc). MAO inhibitors are known that bind in either of these sites (cf. 2-BFI and rasagiline/deprenyl), or simultaneous in both (coumarin-based inhibitors and safinamide; not shown). As our polar deprenyl analogues are designed to bind in both pockets and to form strong contact with the FAD co-factor, MAO-B potency/selectivity will be determined by the overall structure of the molecule i.e. by the nature of the zone1/zone3 modifications in combination with the envisaged modifications to the phenyl ring (zone 2).

Example 2—Selective Inhibition of MAO-B

Figure 9:
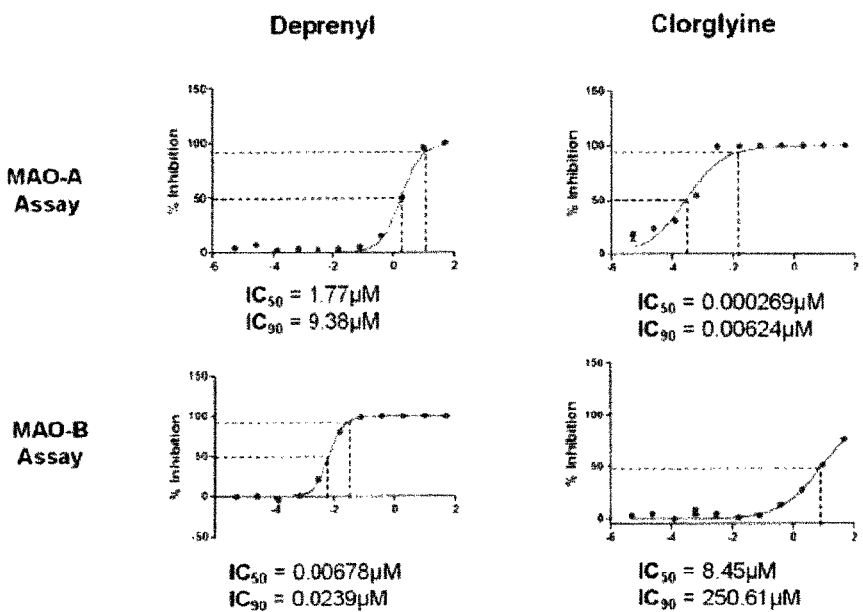
FIG. 9 shows activity and selectivity of deprenyl and clorgyline on MAO-A and MAO-B enzymatic activities. A cell-free Fluorescent Monoamine Oxidase A&B Detection Assay was run to evaluate enzymatic activity on recombinant human MAO-A and MAO-B. As expected, deprenyl, which is a selective MAO-B inhibitor, shows high inhibitory activity with a calculated $IC_{50}$ of 0.0068 μM on MAO-B enzyme. Clorgyline, which is a selective MAO-A inhibitor, displays high inhibitory activity with a calculated $IC_{50}$ of 0.00027 μM on MAO-A enzyme. The assay was repeated to confirm data.
Figure 10A:
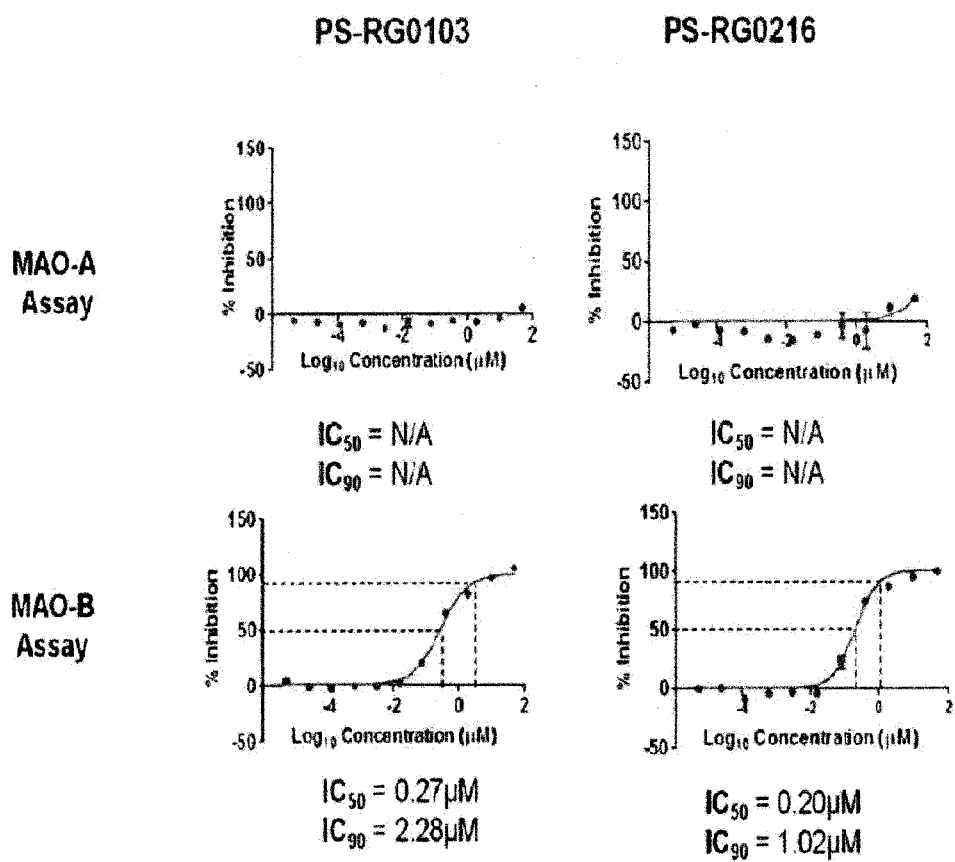
FIGS. 10A and B show activity and selectivity of de novo synthesized MAO-B inhibitors on MAO-A and MAO-B enzymatic activity. Cell-free Fluorescent Monoamine Oxidase A&B Detection Assay was run to evaluate enzymatic activity of the compounds PS-RG0103, PS-RG0216, PS-RG0245 and PS-AD0191 on recombinant human MAO-A and MAO-B. PS-RG0103, PS-RG0216, PS-RG0245 and PS-AD0191, our de novo synthesized MAO-B inhibitors, have $IC_{50}$ values of 0.27, 0.20, 0.21 and 0.30 μM on MAO-B, respectively. Both compounds PS-RG0103 and PS-RG0216 have no activity on MAO-A. Compounds PS-RG0245 and PS-AD0191 resulted in $IC_{50}$ of 17.2 and 54.6 μM on MAO-A, respectively. The assay was repeated to confirm data.

FIG. 9 shows the selective inhibition of MAO-A by clorgyline and selective inhibition of MAO-B by deprenyl. These results demonstrate the suitability of the assay for identification of selective MAO-B inhibitors. FIGS. 10A-B show the selective inhibition of MAO-B by a series of compounds of the present invention. Furthermore, TABLE 3 shows the MAO-A and MAO-B inhibitory activity for the series of compounds tested. These results show that the modification in Zone 1 is functional and that substitution of the benzyloxy group (RG0031A compared to RG0103 and RG0121) in Zone 2 can increase both the inhibitory activity and selectivity towards MAO-B. This may be combined with modifications in Zone 3, as the results obtained for RG0098, RG0122 and RG0123 showed that this zone can be subjected to modifications without knocking out the inhibitory activity.

TABLE 3

| Compound Code | IC50 MAO-A (µM) | IC90 MAO-A (µM) | IC50 MAO-B (µM) | IC90 MAO-B (µM) |
| --- | --- | --- | --- | --- |
| Deprenyl | 1.770 µM | 9.380 µM | 0.00678 µM | 0.0239 µM |
| Clorgyline | 0.000269 µM | 0.00624 µM | 8.450 µM | 250.610 µM |
| PS-AD0031 | Does not inhibit | Does not inhibit | Does not inhibit | Does not inhibit |
| PS-AD0064 | Does not inhibit | Does not inhibit | 1.271 µM | 25.823 µM |
| PS-AD0065 | Does not inhibit | Does not inhibit | 3.281 µM | 81.096 µM |
| PS-AD0065 B | Does not inhibit | Does not inhibit | 10.023 µM | 148.936 µM |
| PS-AD0068 | Does not inhibit | Does not inhibit | 20.045 µM | 505.825 µM |
| PS-AD0095 | Does not inhibit | Does not inhibit | 1.403 µM | 13.397 µM |
| PS-AD0179 | Does not inhibit | Does not inhibit | 7.816 µM | 166.725 µM |
| PS-AD0186 | Does not inhibit | Does not inhibit | 0.560 µM | 4.436 µM |
| PS-AD0191 | 54.576 µM | 423.643 µM | 0.302 µM | 1.026 µM |
| PS-AD0223 | Does not inhibit | Does not inhibit | Does not inhibit | Does not inhibit |
| PS-RG0008 | Does not inhibit | Does not inhibit | 69.183 µM | 331.131 µM |
| PS-RG0019 | Does not inhibit | Does not inhibit | Does not inhibit | Does not inhibit |
| PS-RG0020 | Does not inhibit | Does not inhibit | Does not inhibit | Does not inhibit |
| PS-RG0031A | Does not inhibit | Does not inhibit | 0.908 µM | 30.549 µM |
| PS-RG0058 | Does not inhibit | Does not inhibit | Does not inhibit | Does not inhibit |
| PS-RG0061 | 0.163 µM | 1.054 µM | 0.00458 µM | 0.0230 µM |
| PS-RG0064 | Does not inhibit | Does not inhibit | 7.328 µM | 251.768 µM |
| PS-RG0070 | 12.531 µM | 126.183 µM | 0.0107 µM | 0.0306 µM |
| PS-RG0080 | Does not inhibit | Does not inhibit | Does not inhibit | Does not inhibit |
| PS-RG0097 | Does not inhibit | Does not inhibit | Does not inhibit | Does not inhibit |
| PS-RG0098 | Does not inhibit | Does not inhibit | 0.799 µM | 4.102 µM |
| PS-RG0103 | Does not inhibit | Does not inhibit | 0.275 µM | 2.275 µM |
| PS-RG0121 | Does not inhibit | Does not inhibit | 0.6683 µM | 8.128 µM |
| PS-RG0122 | Does not inhibit | Does not inhibit | 1.432 µM | 19.099 µM |
| PS-RG0123 | Does not inhibit | Does not inhibit | 9.954 µM | 353.997 µM |
| PS-RG0128 | Does not inhibit | Does not inhibit | 5.370 µM | 170.216 µM |
| PS-RG0171 | Does not inhibit | Does not inhibit | 13.002 µM | 1083.927 µM |

TABLE 3-continued

| Compound Code | IC50 MAO-A (µM) | IC90 MAO-A (µM) | IC50 MAO-B (µM) | IC90 MAO-B (µM) |
|---|---|---|---|---|
| PS-RG0172 | Does not inhibit | Does not inhibit | 19.679 µM | 1836.538 µM |
| PS-RG0173 | Does not inhibit | Does not inhibit | 0.785 µM | 13.521 µM |
| PS-RG0174 | Does not inhibit | Does not inhibit | 0.794 µM | 6.699 µM |
| PS-RG0188 | Does not inhibit | Does not inhibit | 0.738 µM | 19.679 µM |
| PS-RG0200 | Does not inhibit | Does not inhibit | Does not inhibit | Does not inhibit |
| PS-RG0210 | Does not inhibit | Does not inhibit | 23.550 µM | 707.946 µM |
| PS-RG0216 | Does not inhibit | Does not inhibit | 0.203 µM | 1.021 µM |
| PS-RG0217 | Does not inhibit | Does not inhibit | 26.607 µM | 576.767 µM |
| PS-RG0218 | Does not inhibit | Does not inhibit | Does not inhibit | Does not inhibit |
| PS-RG0219 | Does not inhibit | Does not inhibit | Does not inhibit | Does not inhibit |
| PS-RG0221 | Does not inhibit | Does not inhibit | 6.761 µM | 101.625 µM |
| PS-RG0226 | 197.697 µM | 1261.828 µM | 0.505 µM | 3.420 µM |
| PS-RG0227 | 954.993 µM | 62950.618 µM | 11.455 µM | 843.335 µM |
| PS-RG0245 | 17.140 µM | 99.770 µM | 0.207 µM | 0.873 µM |
| PS-RG0246 | Does not inhibit | Does not inhibit | 360.579 µM | 10568.175 µM |
| PS-RG0247 | Does not inhibit | Does not inhibit | 19.320 µM | 619.441 µM |
| PS-RG0264 | 358.922 µM | 78523.563 µM | 2.218 µM | 50.466 µM |

Example 3—Selective MAO-B Inhibitors with Reduced Ability to Cross BBB are Useful as Therapeutics for Treatment of Disease The identification of selective MAO-B inhibitors with reduced ability to cross the BBB is accomplished by testing candidate compounds, such as those described in Examples 1 and 2, in a BBB permeability assay. Compounds with reduced ability to cross the BBB are then tested for their ability to improve epithelial barrier, for instance using an MDCK-1 in vitro cell model. Such compounds are then tested for their in vivo ability to ameliorate disease.

Test compounds that meet the criteria for selectivity and functional activity are then tested in single-dose pharmacokinetic studies using deprenyl as a negative control. Pharmacokinetic constants are calculated based on three mice per time-point and six time-points in total. Compounds are administered via IV injection and concentrations of compounds in plasma and brain determined using bioanalytical methods. Bioanalytical analysis is carried out first in plasma and brain, and potentially in target tissues of interest such as the gut. The efficacy of deprenyl and the de novo analog leads is assessed in a proof of concept efficacy study for their ability to ameliorate disease using up to 3 different doses of compound, routes, or schedules and compared to vehicle treated animals. Animals (n=8/group*4 groups=32 animals) are treated for the full duration of the study with the reference compound. Primary measures include daily body weight and daily assessment of relevant clinical observations. This demonstrates efficacy for an MAOB inhibitor following oral dosing in a murine model of disease where loss of epithelial barrier integrity is a critical parameter of the disease.

Example 4—MAO-B Inhibitors as Therapeutics for Treatment of Epithelial Barrier Disease Using a series of techniques including laser capture micro-dissection and global gene array analysis, Ekuni et al. identified that gene expression of MAO B, a pro-oxidative enzyme, was increased almost six-fold in periodontal epithelial cells in an in vivo rat model of chronic periodontitis (Ekuni et al 2009). Earlier studies have also reported an increase in MAOs in biopsies of inflamed periodontal tissues but neither the isotype nor location were described (Satyanarayana et al 1990). In cell culture studies, Putnins et al. has demonstrated that LPS significantly induces MAO B but not MAO A protein expression (Ekuni et al 2009). In addition, anecdotal reports suggest that clinically-approved MAO inhibitors appear to decrease mediators of inflammation and improve chronic conditions such as rheumatoid arthritis and Crohn's disease (Lieb 1983; Kast 1998; Nagatsu et al 2006; Sawada et al 2006; Williams 2008; Nair et al 1993).

In Vitro Data for Disruption and Protection of Mucosal Barrier Integrity:

MDCK-I cells cultured on Transwell™ membranes develop a significant barrier as measured by transepithelial electrical resistance (TEER); treatment with $H_2O_2$ significantly reduced TEER in a concentration-dependent manner and significantly increased AR protein secretion into the media. Amphiregulin (AR) is an EGFR binding ligand and may play a pivotal role in the previously described signaling axis (see FIGS. 15-17). Putnins et al. have demonstrated that co-treatment with the MAO B inhibitor deprenyl negated the $H_2O_2$ effect, increased TEER significantly above the control, and at all three time points reduced AR secretion to control levels or below. Deprenyl co-treatment also rescues LPS reduction of TEER in three barrier cell lines: (i) oral [porcine ligament epithelial (PLE)] (ii) GI [intestinal epithelial cell (IEC)] and (iii) classical [Madin-Darby canine kidney (MDCK-1)].

Putnins et al. have also examined the effect of MAO A, B, and AB inhibitors on TEER and AR secretion. The MAO A/B inhibitor (phenelzine) and MAO B inhibitors (deprenyl and pargyline) increased TEER and reduced AR expression but the MAO A inhibitors (moclobemide and clorgyline) generally reduced TEER, induced barrier loss, and increased AR protein secretion. At low doses, moclobemide treatment resulted in a small increase in the barrier integrity and a reduction in AR was observed, possibly reflecting weak MAO B activity (Willliams 2008; Nair et al 1993). The MAO A/B inhibitor (phenelzine) was also effective; however, the lack of activity of the MAO A selective inhibitors suggests that it is the MAO B inhibition that is responsible for the beneficial effects. Furthermore, the MAO A inhibitory activity limits its potential use because of the severe side-effects associated with MAO A inhibition, e.g. hypertensive crisis.

Preliminary In Vivo Data for Disruption and Protection of Mucosal Barrier Integrity:

Periodontitis is a chronic inflammatory response in the oral mucosa to a primarily LPS-rich Gram-negative bacterial biofilm that is present on teeth. In cell culture, *Porphyromonas gingivalis*, a Gram-negative periodontal pathogen, significantly reduced TEER (Groeger et al 2010). Using an in vivo rat periodontal disease model that demonstrates epithelial proliferation and alveolar bone loss that is consistent with disease Putnins et al. discovered that claudin-1 was significantly reduced with disease onset, and, in cell culture, chronic LPS treatment reduced TEER and claudin-1 protein expression (Fujita et al 2012). Early in vivo proof-of-concept studies utilized the non-selective, MAO A/B inhibitor phenelzine and demonstrated that when the agent was co-applied topically with LPS histological indicators of periodontal disease were reduced (summarized in Ekuni et al 2009). Daily treatment with LPS induced MAO B protein expression and $H_2O_2$ generation in the disease-associated epithelium and increased histological signs of disease. Furthermore, phenelzine treatment reduced local epithelial cell proliferation and migration along the root surface, alveolar bone loss as well as polymorphonuclear (PMN) infiltration and systemic $H_2O_2$. Preliminary examinations following deprenyl treatment in conjunction with seven-day *C. rodentium* infections, indicate that TJ protein localization at the cell periphery was intact and the hyperplastic phenotype was not apparent, despite significant colonization of the bacteria in the colons of the animals Deprenyl itself did not influence bacterial growth rates. Thus, in the two animal models discussed (periodontal and *C. rodentium* diarrheal disease), the inventors have demonstrated the use of MAO inhibitors for the maintenance of barrier integrity. Combined, these data support the concept of limiting development of barrier protection agents to the use of MAO B selective inhibitors.

FIG. 11 shows a comparison of in vitro BBB permeability of deprenyl, cetirizine and de novo synthesized MAO-B inhibitors in wildtype Madin-Darby canine cells (MDCK-WT) to test CNS permeability of compounds PS-RG0103, PS-RG0216, PS-RG0245 and PS-AD0191. Known CNS permeable and impermeable compounds, deprenyl and cetirizine, respectively, were also tested for comparison. Deprenyl shows high permeability with a calculated apparent permeability ($P_{app}$) of 44.0±2.5 ($\times 10^{-6}$ cm/s). Cetirizine, an H1-antagonist anti-histamine with low sedative effects due to its diminished potential to cross the blood brain barrier[1], has a low $P_{app}$ value of 1.7±1.3 ($\times 10^{-6}$ cm/s). For comparison, PS-RG0103, PS-RG0216, PS-RG0245 and PS-AD0191, our de novo synthesized MAO-B inhibitors, also have low $P_{app}$ values of 2.2±0.2, 1.2±0.1, 3.6±0.2 and 7.9±1.4 ($\times 10^{-6}$ cm/s), respectively. FIGS. 12A-C show stability assay in mouse and human liver microsomes was run on compounds deprenyl, PS-RG0103 and PS-RG0216. (A) Deprenyl, a known selective irreversible MAO-B inhibitor, showed less than 2.5% and 15% in mouse and human microsomes remaining after 60 minutes at room temperature, respectively. (B) Compounds PS-RG0103 and (C) PS-RG0216 showed stability for 60 minutes, resulting in 69% and 74% compound remaining in mouse microsome, respectively and 93% and 91% remaining human microsome, respectively.

FIG. 13 shows mouse hepatocyte stability assay was performed on compounds deprenyl, PS-RG0103 and PS-RG0216. Deprenyl, a known MAO-B inhibitor, resulted in less than 2.5% remaining after 60 minutes at room temperature. Compounds PS-RG0103 and PS-RG0216 showed stability at 101% and 100%, respectively. FIG. 14 shows MAO B protein expression preferentially induced in disease sites from patients with Ulcerative Colitis (UC). Punch biopsies were taken from a diseased site and an adjacent non-diseased (control) site of the bowel in patients with ulcerative colitis. The biopsies were flash frozen and embedded in O.C.T. compound in a cryo-mold using a pre-cooled isopentane/liquid nitrogen bath.

FIGS. 15A-C show deprenyl reduces LPS-induced barrier loss in three epithelial cell lines. Porcine ligament epithelial (PLE), rat intestinal epithelial (IEC-6) and Madin Darby canine kidney (MDCK-I) cell lines cultured in Transwell™ chambers and treated with LPS±deprenyl (D). PLE, IEC-6, and MDCK were challenged at 72 hours (T) with LPS (L)±deprenyl. MDCK-I cultures were treated with a concentration range of LPS and 40 µM deprenyl. In each case, TEER was measured every 48 hours after treatment. Statistically significant differences were identified. Specifically, in all three cell lines, LPS significantly reduced the barrier (TEER) (p<0.01) [#s 2, 4, and 6] and LPS+deprenyl significantly induced TEER above control (CTL) (p<0.01) [#s 1, 3, and 5].

FIG. 16 shows MAO A/B, MAO B and MAO A class inhibitors uniquely impact MDCK-I cell TEER. Transwell cultures were treated at 72 hours (T) post-cell plating. Analysis of 144-hour barrier (TEER) using one-way ANOVA with Tukey post-hoc testing found a significant decrease ER with LPS (p<0.01). TEER was increased over control (CTL) (p<0.01) for 5 and 40 µm phenelzine, 5 and 40 µm deprenyl and pargyline, and 5 µm moclobemide. However, 5 and 40 µm clorgyline significantly reduced the barrier (p<0.01).

FIG. 17 shows the effect of deprenyl and novel MAO B inhibitors on transepithelial electrical resistance (TEER) in MDCK (NBL-2) cells. (A). MDCK (NBL-2) cells were seeded at 42000 cells/cm$^2$ on 24-well Polyester Transwell inserts in MEM α medium (#12561-056, Gibco™) containing 10% FBS. TEER was measured using a Millicell® ERS-2 voltohmmeter (Millipore™) starting on day 2 after seeding, followed by a change of media. On day 3 TEER was measured and cells were treated with 10 µM deprenyl, RG0103, RG0216, RG0245 or vehicle ($H_2O$) control in complete media (arrow). On days 6, 7, 8, 9, 10 and 13 TEER was measured. Only on days 6 and 8 media including the aforementioned treatments was changed. Data represent the mean±standard deviation (n=4). (B).

FIG. 18 shows the effect of deprenyl and novel MAO B inhibitors on transepithelial electrical resistance (TEER) in Caco-2 cells. On days 5, 7, 9, 11 and 13 TEER was measured followed by a media change. On day 14 cells were treated with 20 μM deprenyl, RG0103, RG0216, RG0245, AD0191 or vehicle (H$_2$O) control in complete media (arrow). On days 16, 19, 21 and 23 TEER was measured and media was changed including the aforementioned treatments.

FIG. 19 shows attenuation of IL-8 protein expression in LPS- and TNFα-treated human epithelial colorectal adenocarcinoma cells (Caco-2) by deprenyl and RG0216. The left panel shows absolute concentrations of IL-8 protein in supernatants of cells treated with control (media only), 1 μg/mL LPS or 50 ng/mL TNFα. While the right panel shows absolute IL-8 concentrations induced or attenuated by 1 μg/mL LPS or 50 ng/mL TNFα±deprenyl or RG0216. Values were determined by subtracting supernatant cytokine concentrations of control from supernatant cytokine concentrations of treated cells.

FIGS. 20A-F show attenuation of IL-8 (A & B), (C & D) and TNFα protein expression in LPS-treated human intestinal microvascular endothelial cells (HIMEC) by deprenyl and novel MAO B inhibitors. The left panel shows absolute concentrations of IL-8, IL-6 and TNFα protein in supernatants of cells treated with control (media only) or increasing concentrations of LPS. The right panel shows absolute IL-8, IL-6 or TNFα concentrations induced or attenuated by 1000 ng/mL LPS±the novel MAO B inhibitors. Values were determined by subtracting supernatant cytokine concentrations of control from supernatant cytokine concentrations of treated cells.

Figure 21A:
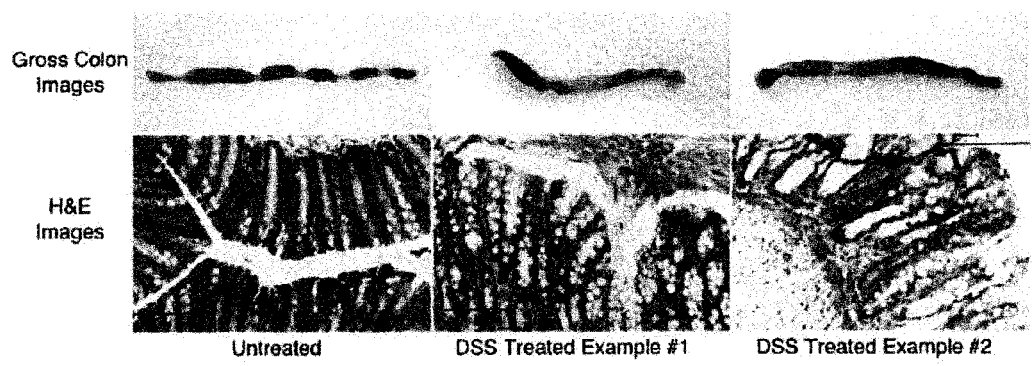
Figure 21B:
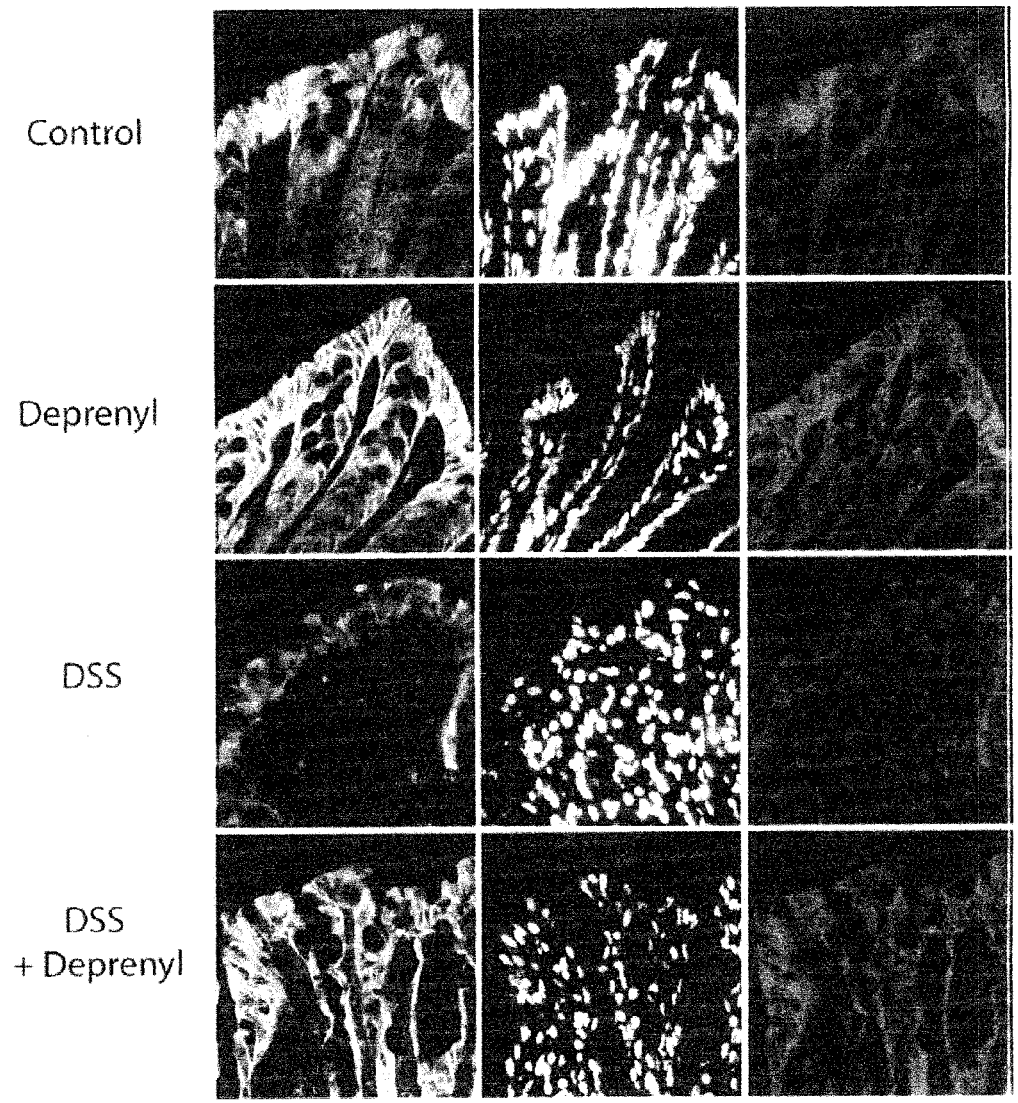

FIGS. 21A and B show a 3% DSS induced colitis and protects epithelial cell-cell claudin-3 localization. Control, deprenyl±DSS treated C57BL/6 mice were treated with 3% DSS in the drinking water and animals sacrificed on day 7. (A). In DSS-treated mice the gross colon images were associated with looser stool and H&E stained sections demonstrated deeper crypts and disorganized epithelium. (B). Control mice demonstrate classical claudin-3 localization that is severely disrupted in DSS-treated animals. In contrast, claudin-3 was better localized to epithelial cell-cell contacts in DSS+deprenyl-treated animals.

FIGS. 22A and B show the effect of deprenyl on DSS-induced colitis in C57BL/6 mice. Daily body weight was measured and calculated by dividing body weight on the specific day by the body weight at day −2. Values are expressed as percent change from day −2 (B).

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention.

REFERENCES

Ekuni D, Firth J D, Nayer T, Tomofuji T, Sanbe T, Irie K, Yamamoto T, Oka T, Liu Z, Vielkind J, Putnins E E. (2009) Lipopolysaccharide-induced epithelial monoamine oxidase mediates alveolar bone loss in a rat chronic wound model. Am J Pathol 175(4):1398-1409.

Lengyel J, Magyar K, Hollósi I, Bartók T, Báthori M, Kalász H, Füst S. (1997) Urinary excretion of deprenyl metabolites. J Chromatogr A 762(1-2):321-326.

Nakashima K. (2005) High-performance liquid chromatographic analysis of drugs of abuse in biologic samples. J Health Sci 51(3):272-277.

Umeda K, Ikenouchi J, Katahira-Tayama S, Furuse K, Sasaki H, Nakayama M, Matsui T, Tsukita S, Furuse M, Tsukita S. (2006) ZO-1 and ZO-2 independently determine where claudins are polymerized in tight-junction strand formation. Cell 126:741-754.

Van Itallie C M, Holmes J, Bridges A, Gookin J L, Coccaro M R, Proctor W, Colegio O R, Anderson J M. (2008) The density of small tight junction pores varies among cell types and is increased by expression of claudin-2. J Cell Sci 121:298-305.

Satyanarayana, M. and Rajeswari, K. R., Biogenic amines in human gingiva in healthy and inflamed states. Indian J Dent Res, 1990. 2 (2-3): p. 170-3.

Lieb, J., Remission of rheumatoid arthritis and other disorders of immunity in patients taking monoamine oxidase inhibitors. Int J Immunopharmacol, 1983. 5 (4): p. 353-7.

Kast, R. E., Crohn's disease remission with phenelzine treatment. Gastroenterology, 1998. 115 (4): p. 1034-5.

Nagatsu, T. and Sawada, M., Molecular mechanism of the relation of monoamine oxidase B and its inhibitors to Parkinson's disease: possible implications of glial cells. J Neural Transm Suppl, 2006 (71): p. 53-65.

Sawada, M., et al., Role of cytokines in inflammatory process in Parkinson's disease. J Neural Transm Suppl, 2006 (70): p. 373-81.

Williams, D. A., Antidepressants. Foye's Principles of Medicinal Chemistry, ed. Lemke, T. L., et al. Vol. 6th edition. 2008, Philadelphia: Lippincott Williams & Wilkins.

Nair, N. P., et al., Biochemistry and pharmacology of reversible inhibitors of MAO-A agents: focus on moclobemide. J Psychiatry Neurosci, 1993. 18 (5): p. 214-25.

Groeger, S., et al., Effects of *Porphyromonas gingivalis* infection on human gingival epithelial barrier function in vitro. Eur J Oral Sci, 2010. 118 (6): p. 582-9.

Fujita, T., et al., Loss of claudin-1 in lipopolysaccharide-treated periodontal epithelium. J Periodontal Res, 2012. 47 (2): p. 222-7.

What is claimed is:
1. A compound of Formula II:

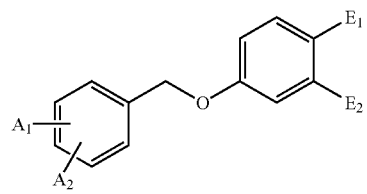

wherein:
A$_1$ is selected from H, F, Cl, Br, I, CN, OMe, NO$_2$, and CO$_2$H;
A$_2$ is selected from H, F, Cl, Br, I, CN, OMe, NO$_2$, and CO$_2$H;

$E_1$ is

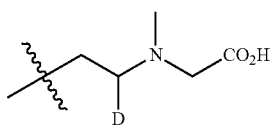 [SMILES: *CC([2H])N(C)CC(=O)O]

and $E_2$ is H; or $E_1$ and $E_2$ form a ring having the structure

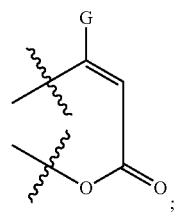

wherein:

D is H, Me, $CH_2Cl$, $CH_2F$, $CH_2Br$, $CH_2I$, $CH_2CN$, $CH_2CH_2OH$, $CH_2OCH_2$-phenyl, $CH_2OH$, or $CO_2Me$; and G is $CH_2N(Me)CH_2CO_2H$.

2. The compound of claim 1, wherein $A_1$ is selected from H, F, Cl, Br, CN, OMe, $NO_2$, and $CO_2H$;

$A_2$ is selected from H, F, Cl, Br, CN, OMe, $NO_2$, and $CO_2H$; and

D is H, Me, $CH_2Cl$, $CH_2CN$, $CH_2CH_2OH$, $CH_2OCH_2$-phenyl, $CH_2OH$, or $CO_2Me$.

3. The compound of claim 1, wherein $A_1$ is selected from H, F, Cl, Br, CN, OMe, $NO_2$, and $CO_2H$;

$A_2$ is selected from H, F, Cl, Br, CN, OMe, $NO_2$, and $CO_2H$; and

D is Me, $CH_2Cl$, $CH_2CN$, $CH_2CH_2OH$, $CH_2OCH_2$-phenyl, $CH_2OH$, or $CO_2Me$.

4. The compound of claim 1, wherein $A_1$ is selected from H, F, Cl, Br, OMe, and $NO_2$;

$A_2$ is selected from H, F, Cl, Br, OMe, and $NO_2$; and

D is Me, $CH_2Cl$, $CH_2CN$, $CH_2OH$, or $CO_2Me$.

5. The compound of claim 1, wherein $A_1$ is H, F, Cl, Br or OMe;

$A_2$ is from H, F, Cl, Br or OMe; and

D is Me, $CH_2Cl$ or $CH_2OH$.

6. The compound of claim 1, wherein the compound is selected from:

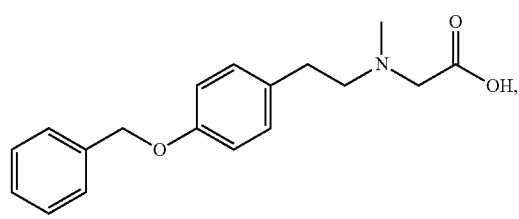

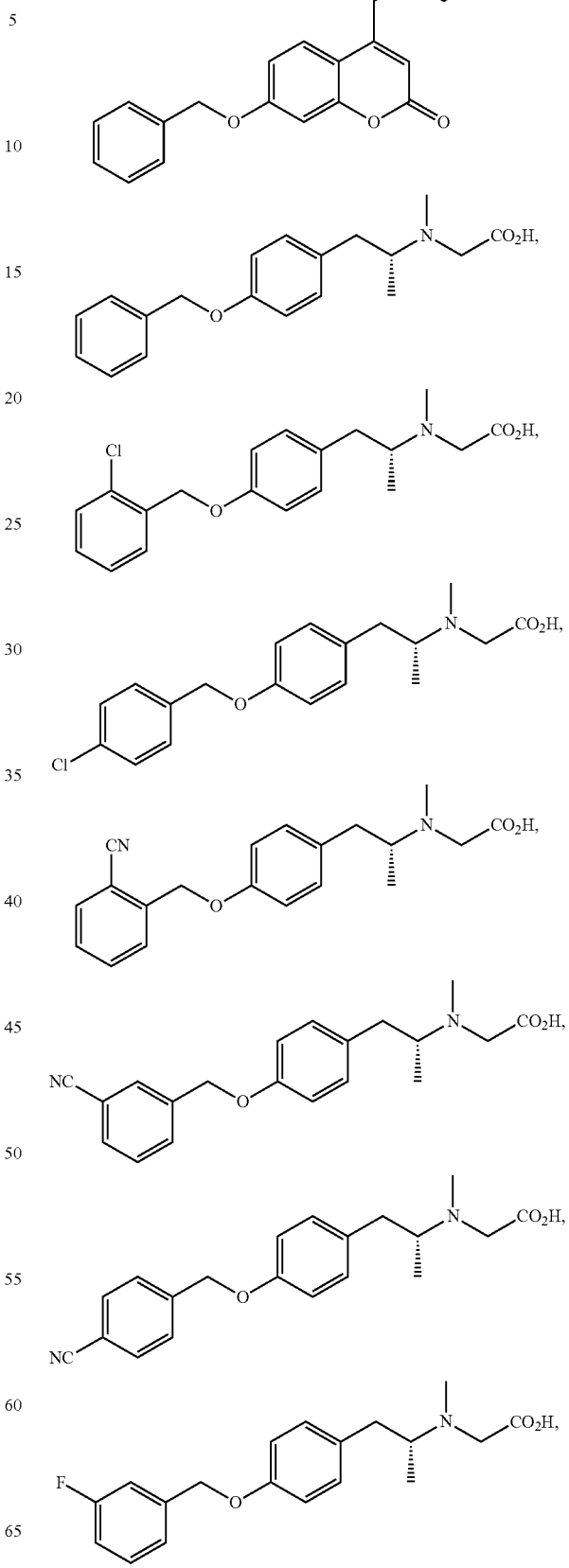

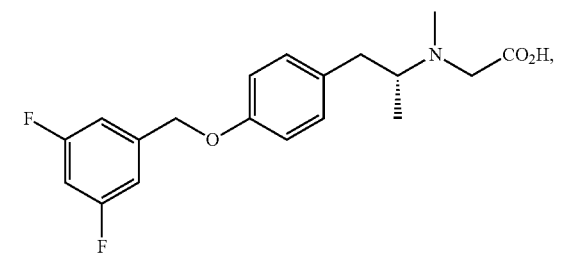
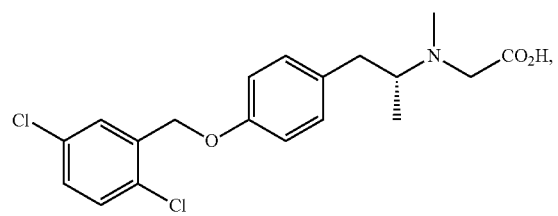
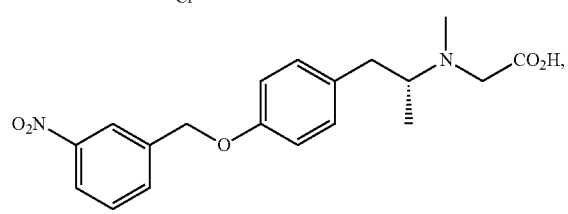
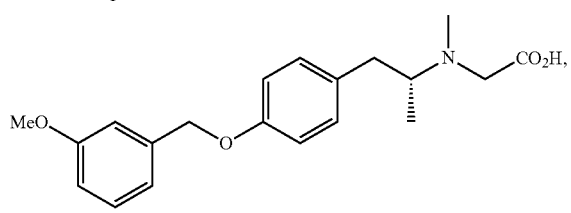
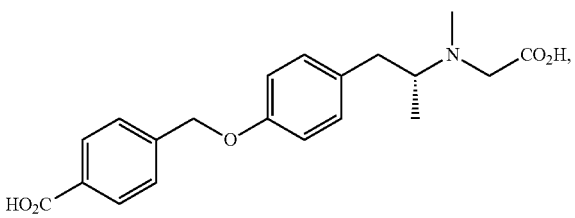
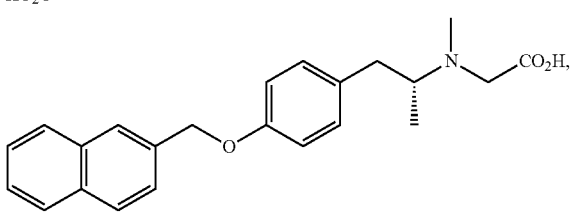
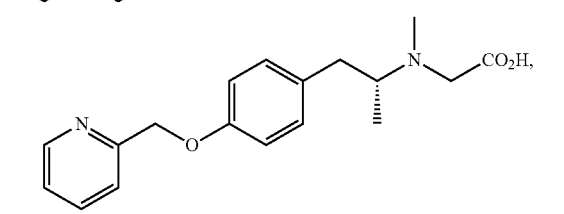
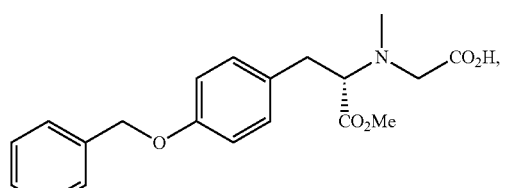
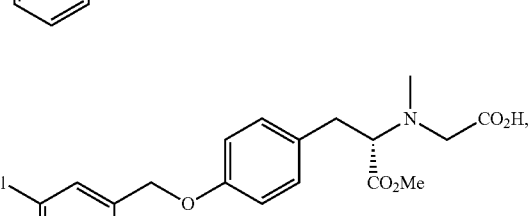
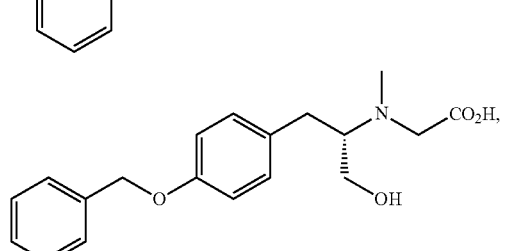
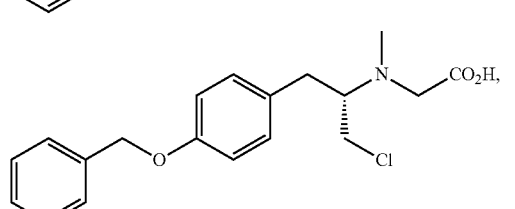
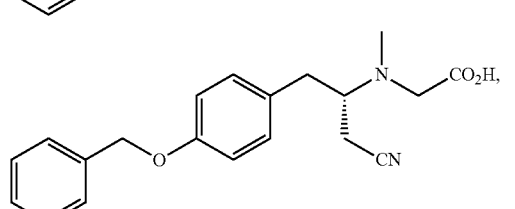
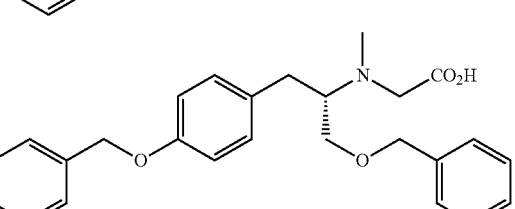
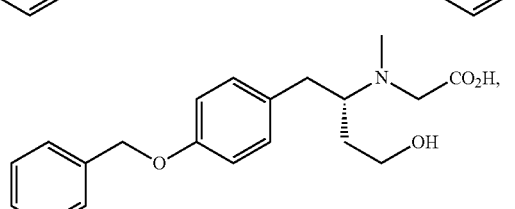
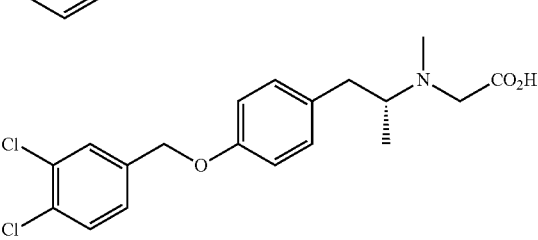

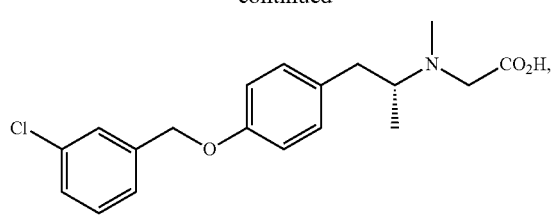
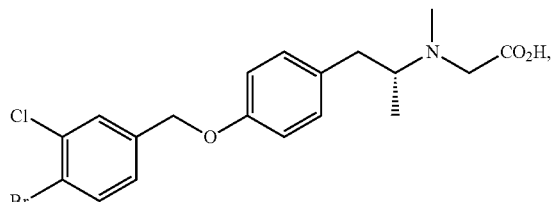
and
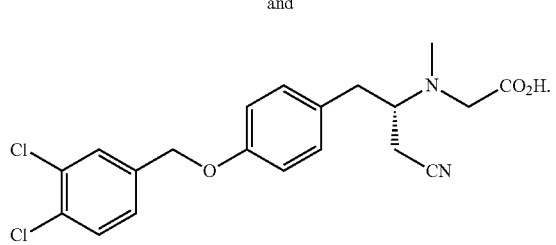
7. The compound of claim 1, wherein the compound is selected from:
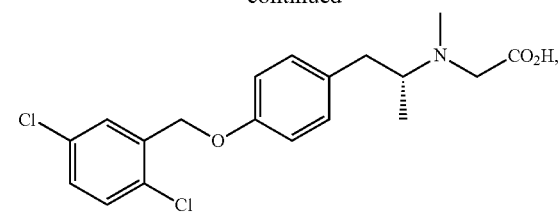
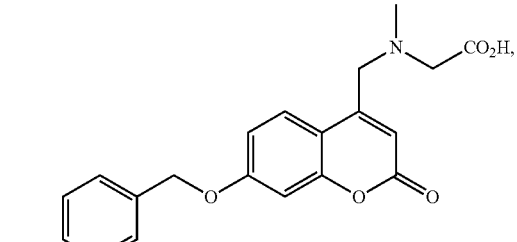
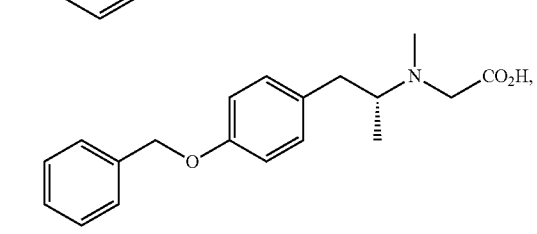
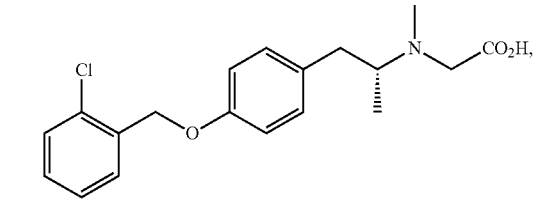
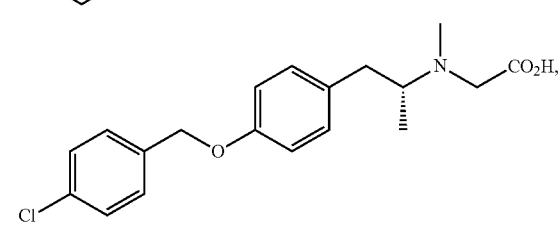
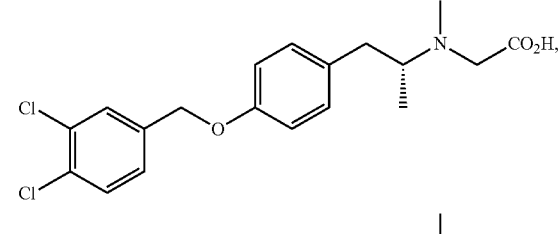
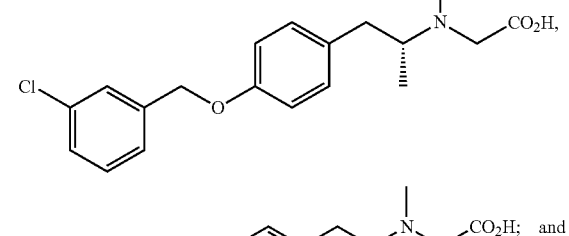
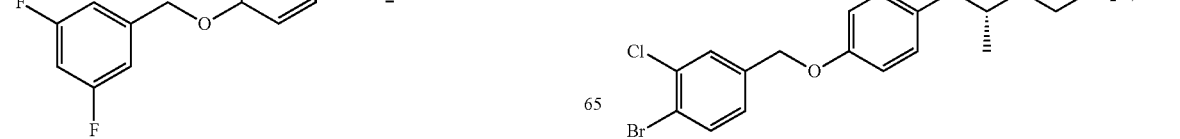

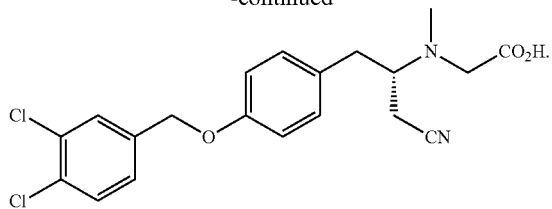

8. The compound of claim 1, wherein the compound is selected from:

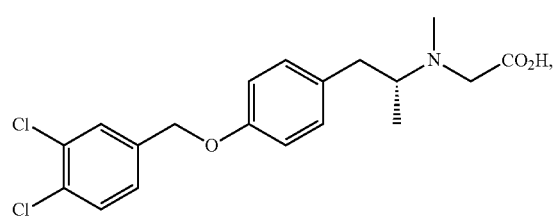

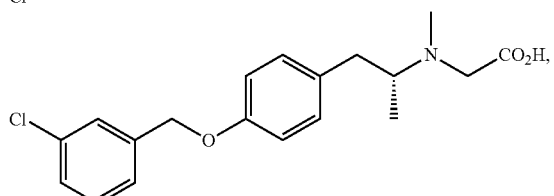

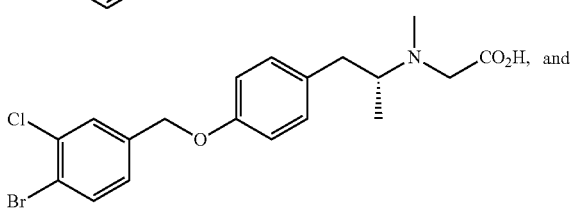

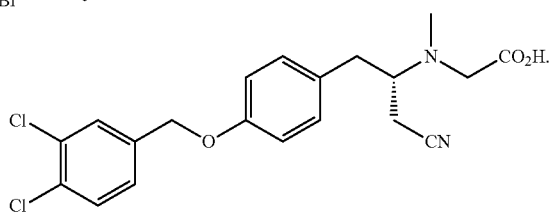

9. The compound of claim 1, wherein the compound is

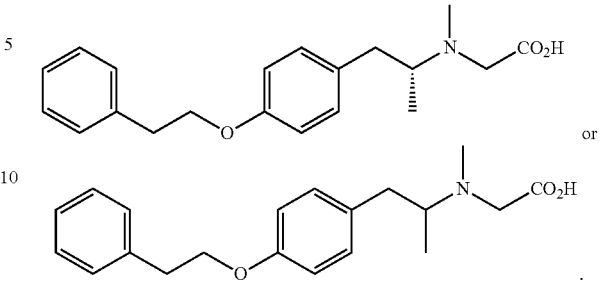

10. A method of treating ulcerative colitis, Crohn's disease, periodontitis, obesity, septicemia, diarrheal disease caused by a pathogenic bacterium, or rheumatoid arthritis, the method comprising administering an MAO-B selective inhibitor of claim 1 to a subject in need thereof.

11. The method of claim 10, wherein the disease is septicemia, Crohn's disease, ulcerative colitis, periodontitis, diarrheal disease caused by a pathogenic bacterium, or asthma.

12. The method of claim 10, wherein the disease is obesity.

13. The method of claim 10, wherein the disease is rheumatoid arthritis.

14. A method of treating ulcerative colitis, Crohn's disease, periodontitis, obesity, septicemia, diarrheal disease caused by a pathogenic bacterium or rheumatoid arthritis, the method comprising administering an MAO-B selective inhibitor having a reduced ability to cross the blood brain barrier to a subject in need thereof wherein the MAO-B selective inhibitor having a reduced ability to cross the blood brain barrier is a compound of claim 1.

15. A commercial package comprising: (a) a compound of claim 1; and (b) instructions for use of the compound in the treatment of ulcerative colitis, Crohn's disease, periodontitis, obesity, septicemia, diarrheal disease caused by a pathogenic bacterium or rheumatoid arthritis.

16. A pharmaceutical composition, the composition comprising: (a) a compound of claim 1; and (b) a pharmaceutically acceptable carrier.

* * * * *

UNITED STATES PATENT AND TRADEMARK OFFICE
CERTIFICATE OF CORRECTION

PATENT NO. : 10,196,345 B2
APPLICATION NO. : 14/915474
DATED : February 5, 2019
INVENTOR(S) : Edward Ewald Putnins et al.

Page 1 of 1

It is certified that error appears in the above-identified patent and that said Letters Patent is hereby corrected as shown below:

In the Specification

Column 39:
Line 45, "lines Animal" should read -- lines. Animal --.

Column 46:
Line 21, "(5mL) H2O" should read -- (5mL) – H2O --.

Column 52:
Line 18, "133.6 (201)," should read -- 133.6 (2CH), --.

Column 59:
Lines 5-6, "10.7 Hz, 11-1)," should read -- 10.7Hz, 1H), --.

Column 62:
Line 41, "dry THE" should read -- dry THF --.

Column 65:
Line 67, "J 8.4 Hz," should read -- J = 8.4Hz, --.

Column 70:
Line 48, "(20 mL)" should read -- (2.0mL) --.

Column 86:
Line 47, "decrease ER" should read -- decrease in TER --.

Signed and Sealed this
Twenty-third Day of July, 2019

Andrei Iancu
*Director of the United States Patent and Trademark Office*